US007091014B1

(12) United States Patent
Aristidou et al.

(10) Patent No.: US 7,091,014 B1
(45) Date of Patent: Aug. 15, 2006

(54) TRANSFORMED MICROORGANISMS WITH IMPROVED PROPERTIES

(75) Inventors: Aristos Aristidou, Espoo (FI); John Londesborough, Helsinki (FI); Merja Penttilä, Helsinki (FI); Peter Richard, Helsinki (FI); Laura Ruohonen, Helsinki (FI); Hans Söderlund, Espoo (FI); Anita Teleman, Djursholmen (SE); Mervi Toivari, Espoo (FI)

(73) Assignee: Valtion Teknillinen Tutkimuskeskus, Espoo (FI)

( * ) Notice: Subject to any disclaimer, the term of this patent is extended or adjusted under 35 U.S.C. 154(b) by 0 days.

(21) Appl. No.: 09/423,554

(22) PCT Filed: Mar. 11, 1999

(86) PCT No.: PCT/FI99/00185

§ 371 (c)(1),
(2), (4) Date: Nov. 10, 1999

(87) PCT Pub. No.: WO99/46363

PCT Pub. Date: Sep. 16, 1999

(30) Foreign Application Priority Data

Mar. 11, 1998 (FI) ...................................... 980551

(51) Int. Cl.
*C12P 7/06* (2006.01)
*C12N 1/14* (2006.01)
(52) U.S. Cl. ................ 435/161; 435/254.2; 435/254.21
(58) Field of Classification Search ................ 435/161, 435/254.2, 254.21, 189, 254.11
See application file for complete search history.

(56) References Cited

U.S. PATENT DOCUMENTS 4,511,656 A * 4/1985 Gong ........................... 435/161
5,424,202 A * 6/1995 Ingram et al. ............... 435/161
5,487,989 A * 1/1996 Fowler et al. ............... 435/161

FOREIGN PATENT DOCUMENTS

EP       0733712       9/1996
WO       WO 9742307    11/1997

OTHER PUBLICATIONS

Jeffries T. W. et al, Strain selection, taxonomy, and genetics of xylose-fermenting yeasts, Enzyme Microb. Technol., 1994, 922-932.*
Da Silva L. et al. Effects of potassium on the ethanol production rate of Saccharomyces cerevisiae carrying the plasmid pCYG4 related with ammonia assimilation, Applied Biochemistry and Biotechnology, 1992, 37, 1-10-abstract.*
Elington J. M. et al, Decreasing acetic acid accumulation by a glycerol overproducing strain of Saccharomyces cerevisiae by deleting the ALD6 aldehyde, Yeast, 2002, 19, 295-301-abstract.*
Valdi H. et al. Improved ethanol production by glycerol 3-phosphate dehydrogenase mutants of Saccharomyces cerevisiae, Applied Microbiology and Biotechnology (1998) 50, 434-439.*
Nissen et al. Optimization of Ethanol Production in Saccharomyces cerevisiae by metabolic engineering of he Ammonium Assimilation, Metabolic Engineering 2000, 2, 69-77.*
Microbiology, vol. 142, 1996, Nina Meinander et al, p. 165-p. 172.
Yeast, vol. 13, 1997, s. 783-793 Sumio, Michnick, Jean-Louis Roustan, Fabienne Remize, Pierre Barre and Sylvie Dequin.
Appln. Microbiol Biotechnol, vol. 49, No. 1, 1998, s. 24-30.
J. Hallborn et al., Microbiol. Biotechnol 1994, vol. 42, pp. 326-333.
A. Marx, Berichte des Forschungszentrums Julich (Juel-3459), 1997, pp. 1-111.
S. Suye, Recent Res. Devel. in Fermentation and Bioeng., 1998, pp. 55-64.
Baggio et al., (Abstract) Journal of Bacteriology (Dec. 1996) 178 (24) 7212-20.
Schaap et al., (Abstract) Molecular and General Genetics (Feb. 25, 1996) 250 (3) 339-47.
Zhang et al., (Abstract) Journal of Bacteriology (Jan. 1996) 178 (2) 490-5.
Samuelson et al., (Abstract) Archives of Medical Research (1992) 23 (2) 31-3.
Cannio et al., (Abstract) Journal of Bacteriology (Jan. 1996) 178 (1) 301-5.
Li et al., (Abstract) Journal of Bacteriology (Jul. 1997) 179 (13) 4433-7.
Kim et al., (Abstract) Plant Molecular Biology (Dec. 1994) 26 (6) 1833-41.
Addis et al., (Abstract) Microbial Pathogenesis (Jul. 1997) 23 (1) 55-61.
Ansell et al, (Abstract) EMBO Journal (May 1, 1997) 16 (9) 2179-87.
Valverde et al., (Abstract) Journal of Bacteriology (Jul. 1997) 179 (14) 4513-22.
Tamoi et al., (Abstract ) Biochemical Journal (Jun. 1, 1996) 316 (Pt 2) 685-90.
Protein Sequence of D-xylose 1-dehydrogenase, Gene 162 (1), 93-97 (1995).

(Continued)

*Primary Examiner*—Rebecca E. Prouty
*Assistant Examiner*—M Walicka
(74) *Attorney, Agent, or Firm*—Birch, Stewart, Kolasch & Birch, LLP

(57) ABSTRACT

The present invention relates to genetic engineering of production microorganisms used in biotechnology to improve their properties so that they produce useful products more efficiently. The microorganisms express at least one enzyme that causes the functional coupling of the oxidation and reduction of substrates by two pyridine nucleotide-linked dehydrogenase reactions with different specificities for the NAD/NADH and NADP/NADPH coenzyme couples and so facilitates the transfer of electrons between the two coenzyme couples through the said substrates. In particular the invention relates to increasing the yields of products such as ethanol or amino acids from carbon and nitrogen sources such as biomass comprising hexoes, pentoses or their polymers.

9 Claims, 16 Drawing Sheets

OTHER PUBLICATIONS

Protein Sequence of Orotate reductase, Curr. Genet. 30 (2), 159-165 (1996).

Isas et al., (Abstract) Journal of Biological Chemistry (Sep. 8, 1995) 270 (36) 21258-63.

CA, 125:5202, corresponding to Biochemistry, (1996), 35(24), p. 7873-7878.

CA, 124:340999, corresponding to Environ.Biotechnol., (Pap. Int Symp.) (1996) (meeting date 1994).

Chemical Abstracts vol. 119, p. 488-89, 4708K, corresponding to Appl. Microbiol. Biotechol. 1993, 38(6), p. 776-783.

Biosis, 97:452608, corresponding to Applied Microbiology and Biotechnology, 48(2), p. 218-224, 1997.

Chemical Abstracts vol. 121, p. 802, 33237c, corresponding to Appl. Microbiol. Biotechnol, 1994, 41(1), p. 8-12.

\* cited by examiner

Fig. 2/1

```
                 201                                                              250
Aspergillus  ME  .......... HIFRRPKGLF ISISDRGH.. .......... .VRSIVDNWP ENHVKAVVVT DGERILGLGD
Human        ME  .......... DIYRYPEGCY LDIDHNDLSY IKQQLSEFGK SDSVEYIIIT DSEGILGIGD
Spombe       ME  .......... HRFRKPEGVF LDITEPDS.. .......... IECRLATYGG DKDVDYIVVS DSEGILGIGD
Scerevisiae  ME  .......... .......... .......... .......... .......... .......... ..........
Trichoderma  ME  .......... .......... .......... .......... .......... .......... ..........

251                                                              300
AspergillusME    .......... LGVYGMGIPV GKLCLYTACA GIRPDRCLPV .......... RGTNNEE LNDKLVLGD
HumanME          .......... QGVGGVLISV AKGHLMTLCA GLDPNRFLPI CIDVGTDNIA LLKDPF MGL
SpombeME         .......... QGIGGVRIAI SKLALMTLCG GIHPGRVLPV VLDVGTNNET HRKNHQ MGL
ScerevisiaeME    .......... .......... .......... .......... CLDVGTNKK EARDEL MGN
Trichoderma      .......... .......... .......... .......... .......... .......... ..........

301                                                              350
Aspergillus  ME  RQRRAQGEEY DKEVDKEVRM AGRGFEMPIS TCSEDIFGLQN AKRIEDRYRS
Human        ME  YQKRDTQEY DLIEEMKA ITDRYGRNTL IQEDFGNHN AFRFLRKYRE
Spombe       ME  RKDRVRGEQY SHLDNVIKA IREVFE.EAF IHFIHCLAN AKRIEDHYRP
Scerevisiae  ME  KFSRIRGKQM DDELEKEIKA VKKVYP.SAV LHEEDEGVKN ARRLEKYRY
Trichoderma  ME  .......... .......... .......... .......... ..........

351                                                              400
Aspergillus  ME  QLPC...... KYCTFNDDIQ GTAAVALAGL LAAQKVISKP ISEHKILFLG AGEAALGIAN
Human        ME  DIACFNDDIQ GTGAVALAAI IGALHVTKSP LTEQRIMIFG AGTAGVGIAN
Spombe       ME  ELPSFNDDIQ GTGAVVMASL IAALKHTNRD LKDTRVLIYG AGSAGLGIAD
Scerevisiae  ME  .......... .......... .......... .......... ..........
Trichoderma  ME  .......... .......... .......... .......... ..........
```

Fig. 2/2

SEQUENCE LISTING

```
<160> NUMBER OF SEQ ID NOS: 14

<210> SEQ ID NO 1
<211> LENGTH: 71
<212> TYPE: PRT
<213> ORGANISM: Aspergillus nidulans

<400> SEQUENCE: 1

Arg Gly Thr Asn Asn Glu Glu Leu Leu Asn Asp Lys Leu Tyr Leu Gly
  1               5                  10                  15

Leu Arg Gln Arg Arg Ala Gln Gly Glu Glu Tyr Asp Lys Phe Val Asp
             20                  25                  30

Lys Phe Val Arg Met Ala Gly Arg Gly Phe Pro Met Pro Ile Ser Thr
         35                  40                  45
```

```
Cys Ser Glu Asp Phe Gly Leu Gln Asn Ala Lys Arg Ile Leu Asp Arg
        50                  55                  60

Tyr Arg Ser Gln Leu Pro Cys
 65                  70
```

<210> SEQ ID NO 2
<211> LENGTH: 156
<212> TYPE: PRT
<213> ORGANISM: Trichoderma reesei

<400> SEQUENCE: 2

```
Ala Gly Ala His Arg Gly Gly Arg Ser Arg Thr Ser Gly Ser Pro
 1               5                  10                  15

Gly Cys Arg Asn Ser Ala Arg Gly Met Asn Ser Ile Leu Arg Thr Thr
                20                  25                  30

Ser Ser Arg Leu Ser Lys Ser Ser Asn Ile His Cys Thr Ser Thr Leu
            35                  40                  45

Arg Tyr Ser Pro Gln Arg Ser Ser Pro Leu Cys Cys Lys Pro Arg
        50                  55                  60

Ser Ser Ser Ser Leu Thr Met Ser Ser Ser Lys Pro Thr Lys Phe Ser
 65                  70                  75                  80

His Leu Pro Leu Ser Thr Thr Gly Pro Leu Glu Cys Ala Leu Thr Gly
                85                  90                  95

Thr Ala Leu Leu Asn Ser Pro Ile Phe Asn Lys Gly Ser Ala Phe Pro
                100                 105                 110

Leu Ser Glu Arg Arg Gln Phe Asn Leu Thr Gly Leu Leu Pro Ala Asn
            115                 120                 125

Glu Gln Thr Leu Asp Asn Gln Val Lys Arg Ala Tyr Gln Gln Tyr Gln
130                 135                 140

Ser Arg Gly Asp Asp Trp Pro Arg Thr Val Pro Asp
145                 150                 155
```

<210> SEQ ID NO 3
<211> LENGTH: 584
<212> TYPE: PRT
<213> ORGANISM: Homo sapiens

<400> SEQUENCE: 3

```
Met Leu Ser Arg Leu Arg Val Val Ser Thr Thr Cys Thr Leu Ala Cys
 1               5                  10                  15

Arg His Leu His Ile Lys Glu Lys Gly Lys Pro Leu Met Leu Asn Pro
                20                  25                  30

Arg Thr Asn Lys Gly Met Ala Phe Thr Leu Gln Glu Arg Gln Met Leu
            35                  40                  45

Gly Leu Gln Gly Leu Leu Pro Pro Lys Ile Glu Thr Gln Asp Ile Gln
        50                  55                  60

Ala Leu Arg Phe His Arg Asn Leu Lys Lys Met Thr Ser Pro Leu Glu
 65                  70                  75                  80

Lys Tyr Ile Tyr Ile Met Gly Ile Gln Glu Arg Asn Glu Lys Leu Phe
                85                  90                  95

Tyr Arg Ile Leu Gln Asp Asp Ile Glu Ser Leu Met Pro Ile Val Tyr
                100                 105                 110

Thr Pro Thr Val Gly Leu Ala Cys Ser Gln Tyr Gly His Ile Phe Arg
            115                 120                 125

Arg Pro Lys Gly Leu Phe Ile Ser Ile Ser Asp Arg Gly His Val Arg
130                 135                 140
```

-continued

```
Ser Ile Val Asp Asn Trp Pro Glu Asn His Val Lys Ala Val Val
145                 150                 155                 160

Thr Asp Gly Glu Arg Ile Leu Gly Leu Gly Asp Leu Gly Val Tyr Gly
                165                 170                 175

Met Gly Ile Pro Val Gly Lys Leu Cys Leu Tyr Thr Ala Cys Ala Gly
            180                 185                 190

Ile Arg Pro Asp Arg Cys Leu Pro Val Cys Ile Asp Val Gly Thr Asp
        195                 200                 205

Asn Ile Ala Leu Leu Lys Asp Pro Phe Tyr Met Gly Leu Tyr Gln Lys
    210                 215                 220

Arg Asp Arg Thr Gln Gln Tyr Asp Asp Leu Ile Asp Glu Phe Met Lys
225                 230                 235                 240

Ala Ile Thr Asp Arg Tyr Gly Arg Asn Thr Leu Ile Gln Phe Glu Asp
                245                 250                 255

Phe Gly Asn His Asn Ala Phe Arg Phe Leu Arg Lys Tyr Arg Glu Lys
            260                 265                 270

Tyr Cys Thr Phe Asn Asp Asp Ile Gln Gly Thr Ala Ala Val Ala Leu
        275                 280                 285

Ala Gly Leu Leu Ala Ala Gln Lys Val Ile Ser Lys Pro Ile Ser Glu
    290                 295                 300

His Lys Ile Leu Phe Leu Gly Ala Gly Glu Ala Ala Leu Gly Ile Ala
305                 310                 315                 320

Asn Leu Ile Val Met Ser Met Val Glu Asn Gly Leu Ser Glu Gln Glu
                325                 330                 335

Ala Gln Lys Lys Ile Trp Met Phe Asp Lys Tyr Gly Leu Leu Val Lys
            340                 345                 350

Gly Arg Lys Ala Lys Ile Asp Ser Tyr Gln Glu Pro Phe Thr His Ser
        355                 360                 365

Ala Pro Glu Ser Ile Pro Asp Thr Phe Glu Asp Ala Val Asn Ile Leu
    370                 375                 380

Lys Pro Ser Thr Ile Ile Gly Val Ala Gly Ala Gly Arg Leu Phe Thr
385                 390                 395                 400

Pro Asp Val Ile Arg Ala Met Ala Ser Ile Asn Glu Arg Pro Val Ile
                405                 410                 415

Phe Ala Leu Ser Asn Pro Thr Ala Gln Ala Glu Cys Thr Ala Glu Glu
            420                 425                 430

Ala Tyr Thr Leu Thr Glu Gly Arg Cys Leu Phe Ala Ser Gly Ser Pro
        435                 440                 445

Phe Gly Pro Val Lys Leu Thr Asp Gly Arg Val Phe Thr Pro Gly Gln
    450                 455                 460

Gly Asn Asn Val Tyr Ile Phe Pro Gly Val Ala Leu Ala Val Ile Leu
465                 470                 475                 480

Cys Asn Thr Arg His Ile Ser Asp Ser Val Phe Leu Glu Ala Ala Lys
                485                 490                 495

Ala Leu Thr Ser Gln Leu Thr Asp Glu Glu Leu Ala Gln Gly Arg Leu
            500                 505                 510

Tyr Pro Pro Leu Ala Asn Ile Gln Glu Val Ser Ile Asn Ile Ala Ile
        515                 520                 525

Lys Val Thr Glu Tyr Leu Tyr Ala Asn Lys Met Ala Phe Arg Tyr Pro
    530                 535                 540

Glu Pro Glu Asp Lys Ala Lys Tyr Val Lys Glu Arg Thr Trp Arg Ser
545                 550                 555                 560
```

Glu Tyr Asp Ser Leu Leu Pro Asp Val Tyr Glu Trp Pro Glu Ser Ala
            565                 570                 575
Ser Ser Pro Pro Val Ile Thr Glu
            580

<210> SEQ ID NO 4
<211> LENGTH: 565
<212> TYPE: PRT
<213> ORGANISM: Schizosaccharomyces pombe

<400> SEQUENCE: 4

Met Pro Ala Gly Thr Lys Glu Gln Ile Glu Cys Pro Leu Lys Gly Val
 1               5                  10                  15

Thr Leu Leu Asn Ser Pro Arg Tyr Asn Lys Asp Thr Ala Phe Thr Pro
            20                  25                  30

Glu Glu Arg Gln Lys Phe Glu Ile Ser Ser Arg Leu Pro Pro Ile Val
         35                  40                  45

Glu Thr Leu Gln Gln Val Asp Arg Cys Tyr Asp Gln Tyr Lys Ala
      50                  55                  60

Ile Gly Asp Glu Pro Leu Gln Lys Asn Leu Tyr Leu Ser Gln Leu Ser
 65                  70                  75                  80

Val Thr Asn Gln Thr Leu Phe Tyr Ala Leu Ile Ser Gln His Leu Ile
                85                  90                  95

Glu Met Ile Pro Ile Ile Tyr Thr Pro Thr Glu Gly Asp Ala Ile Lys
            100                 105                 110

Gln Phe Ser Asp Ile Tyr Arg Tyr Pro Glu Gly Cys Tyr Leu Asp Ile
        115                 120                 125

Asp His Asn Asp Leu Ser Tyr Ile Lys Gln Gln Leu Ser Glu Phe Gly
    130                 135                 140

Lys Ser Asp Ser Val Glu Tyr Ile Ile Thr Asp Ser Glu Gly Ile
145                 150                 155                 160

Leu Gly Ile Gly Asp Gln Gly Val Gly Gly Val Leu Ile Ser Val Ala
                165                 170                 175

Lys Gly His Leu Met Thr Leu Cys Ala Gly Leu Asp Pro Asn Arg Phe
            180                 185                 190

Leu Pro Ile Val Leu Asp Val Gly Thr Asn Asn Glu Thr His Arg Lys
        195                 200                 205

Asn His Gln Tyr Met Gly Leu Arg Lys Asp Arg Val Arg Gly Glu Gln
    210                 215                 220

Tyr Asp Ser Phe Leu Asp Asn Val Ile Lys Ala Ile Arg Glu Val Phe
225                 230                 235                 240

Pro Glu Ala Phe Ile His Phe Glu Asp Phe Gly Leu Ala Asn Ala Lys
                245                 250                 255

Arg Ile Leu Asp His Tyr Arg Pro Asp Ile Ala Cys Phe Asn Asp Asp
            260                 265                 270

Ile Gln Gly Thr Gly Ala Val Ala Leu Ala Ala Ile Gly Ala Leu
        275                 280                 285

His Val Thr Lys Ser Pro Leu Thr Glu Gln Arg Ile Met Ile Phe Gly
    290                 295                 300

Ala Gly Thr Ala Gly Val Gly Ile Ala Asn Gln Ile Val Ala Gly Met
305                 310                 315                 320

Val Thr Asp Gly Leu Ser Leu Asp Lys Ala Arg Gly Asn Leu Phe Met
                325                 330                 335

Ile Asp Arg Cys Gly Leu Leu Leu Glu Arg His Ala Lys Ile Ala Thr
            340                 345                 350

-continued

Asp Gly Gln Lys Pro Phe Leu Lys Asp Ser Asp Phe Lys Glu Val
        355                 360                 365

Pro Ser Gly Asp Ile Asn Leu Glu Ser Ala Ile Ala Leu Val Lys Pro
    370                 375                 380

Thr Ile Leu Leu Gly Cys Ser Gly Gln Pro Gly Lys Phe Thr Glu Lys
385                 390                 395                 400

Ala Ile Arg Glu Met Ser Lys His Val Glu Arg Pro Ile Ile Phe Pro
                405                 410                 415

Ile Ser Asn Pro Thr Thr Leu Met Glu Ala Lys Pro Asp Gln Ile Asp
                420                 425                 430

Lys Trp Ser Asp Gly Lys Ala Leu Ile Ala Thr Gly Ser Pro Leu Pro
            435                 440                 445

Pro Leu Asn Arg Asn Gly Lys Lys Tyr Val Ile Ser Gln Cys Asn Asn
    450                 455                 460

Ala Leu Leu Tyr Pro Ala Leu Gly Val Ala Cys Val Leu Ser Arg Cys
465                 470                 475                 480

Lys Leu Leu Ser Asp Gly Met Leu Lys Ala Ala Ser Asp Ala Leu Ala
                485                 490                 495

Thr Val Pro Arg Ser Leu Phe Ala Ala Asp Glu Ala Leu Leu Pro Asp
            500                 505                 510

Leu Asn Asn Ala Arg Glu Ile Ser Arg His Ile Val Phe Ala Val Leu
        515                 520                 525

Lys Gln Ala Val Ser Glu Gly Met Ser Thr Val Asp Leu Pro Lys Asp
    530                 535                 540

Asp Ala Lys Leu Lys Glu Trp Ile Ile Glu Arg Glu Trp Asn Pro Glu
545                 550                 555                 560

Tyr Lys Pro Phe Val
            565

<210> SEQ ID NO 5
<211> LENGTH: 669
<212> TYPE: PRT
<213> ORGANISM: Saccharomyces cerevisiae

<400> SEQUENCE: 5

Met Leu Arg Thr Arg Leu Ser Val Ser Val Ala Ala Arg Ser Gln Leu
1               5                   10                  15

Thr Arg Ser Leu Thr Ala Ser Arg Thr Ala Pro Leu Arg Arg Trp Pro
            20                  25                  30

Ile Gln Gln Ser Arg Leu Tyr Ser Ser Asn Thr Arg Ser His Lys Ala
        35                  40                  45

Thr Thr Thr Arg Glu Asn Thr Phe Gln Lys Pro Tyr Ser Asp Glu Glu
    50                  55                  60

Val Thr Lys Thr Pro Val Gly Ser Arg Ala Arg Lys Ile Phe Glu Ala
65                  70                  75                  80

Pro His Pro His Ala Thr Arg Leu Thr Val Glu Gly Ala Ile Glu Cys
                85                  90                  95

Pro Leu Glu Ser Phe Gln Leu Leu Asn Ser Pro Leu Phe Asn Lys Gly
            100                 105                 110

Ser Ala Phe Thr Gln Glu Glu Arg Glu Ala Phe Asn Leu Glu Ala Leu
        115                 120                 125

Leu Pro Pro Gln Val Asn Thr Leu Asp Glu Gln Leu Glu Arg Ser Tyr
    130                 135                 140

Lys Gln Leu Cys Tyr Leu Lys Thr Pro Leu Ala Lys Asn Asp Phe Met
145                 150                 155                 160

```
Thr Ser Leu Arg Val Gln Asn Lys Val Leu Tyr Phe Ala Leu Ile Arg
                165                 170                 175

Arg His Ile Lys Glu Leu Val Pro Ile Ile Tyr Pro Thr Glu Gly
            180                 185                 190

Asp Ala Ile Ala Ala Tyr Ser His Arg Phe Arg Lys Pro Glu Gly Val
            195                 200                 205

Phe Leu Asp Ile Thr Glu Pro Asp Ser Ile Glu Cys Arg Leu Ala Thr
    210                 215                 220

Tyr Gly Gly Asp Lys Asp Val Asp Tyr Ile Val Val Ser Asp Ser Glu
225                 230                 235                 240

Gly Ile Leu Gly Ile Gly Asp Gln Gly Ile Gly Gly Val Arg Ile Ala
                245                 250                 255

Ile Ser Lys Leu Ala Leu Met Thr Leu Cys Gly Gly Ile His Pro Gly
            260                 265                 270

Arg Val Leu Pro Val Cys Leu Asp Val Gly Thr Asn Asn Lys Lys Leu
        275                 280                 285

Ala Arg Asp Glu Leu Tyr Met Gly Asn Lys Phe Ser Arg Ile Arg Gly
    290                 295                 300

Lys Gln Tyr Asp Asp Phe Leu Glu Lys Phe Ile Lys Ala Val Lys Lys
305                 310                 315                 320

Val Tyr Pro Ser Ala Val Leu His Phe Glu Asp Phe Gly Val Lys Asn
                325                 330                 335

Ala Arg Arg Leu Leu Glu Lys Tyr Arg Tyr Glu Leu Pro Ser Phe Asn
            340                 345                 350

Asp Asp Ile Gln Gly Thr Gly Ala Val Val Met Ala Ser Leu Ile Ala
        355                 360                 365

Ala Leu Lys His Thr Asn Arg Asp Leu Lys Asp Thr Arg Val Leu Ile
    370                 375                 380

Tyr Gly Ala Gly Ser Ala Gly Leu Gly Ile Ala Asp Gln Ile Val Asn
385                 390                 395                 400

His Met Val Thr His Gly Val Asp Lys Glu Glu Ala Arg Lys Lys Ile
                405                 410                 415

Phe Leu Met Asp Arg Arg Gly Leu Ile Leu Gln Ser Tyr Glu Ala Asn
            420                 425                 430

Ser Thr Pro Ala Gln His Val Tyr Ala Lys Ser Asp Ala Glu Trp Ala
        435                 440                 445

Gly Ile Asn Thr Arg Ser Leu His Asp Val Val Glu Asn Val Lys Pro
    450                 455                 460

Thr Cys Leu Val Gly Cys Ser Thr Gln Ala Gly Ala Phe Thr Gln Asp
465                 470                 475                 480

Val Val Glu Glu Met His Lys His Asn Pro Arg Pro Ile Ile Phe Pro
                485                 490                 495

Leu Ser Asn Pro Thr Arg Leu His Glu Ala Val Pro Ala Asp Leu Met
            500                 505                 510

Lys Trp Thr Asn Asn Asn Ala Leu Val Ala Thr Gly Ser Pro Phe Pro
        515                 520                 525

Pro Val Asp Gly Tyr Arg Ile Ser Glu Asn Asn Cys Tyr Ser Phe
    530                 535                 540

Pro Gly Ile Gly Leu Gly Ala Val Leu Ser Arg Ala Thr Thr Ile Thr
545                 550                 555                 560

Asp Lys Met Ile Ser Ala Ala Val Asp Gln Leu Ala Glu Leu Ser Pro
                565                 570                 575
```

```
Leu Arg Glu Gly Asp Ser Arg Pro Gly Leu Leu Pro Gly Leu Asp Thr
            580                 585                 590

Ile Thr Asn Thr Ser Ala Arg Leu Ala Thr Ala Val Ile Leu Gln Ala
        595                 600                 605

Leu Glu Glu Gly Thr Ala Arg Ile Glu Gln Gln Val Pro Gly Gly
    610                 615                 620

Ala Pro Gly Glu Thr Val Lys Val Pro Arg Asp Phe Asp Glu Cys Leu
625                 630                 635                 640

Gln Trp Val Lys Ala Gln Met Trp Glu Pro Val Tyr Arg Pro Met Ile
                645                 650                 655

Lys Val Gln His Asp Pro Ser Val His Thr Asn Gln Leu
            660                 665

<210> SEQ ID NO 6
<211> LENGTH: 28
<212> TYPE: DNA
<213> ORGANISM: Artificial Sequence
<220> FEATURE:
<223> OTHER INFORMATION: Description of Artificial Sequence:Primer

<400> SEQUENCE: 6
ccagtgatat cgaggatgag attagtac                                       28

<210> SEQ ID NO 7
<211> LENGTH: 28
<212> TYPE: DNA
<213> ORGANISM: Artificial Sequence
<220> FEATURE:
<223> OTHER INFORMATION: Description of Artificial Sequence:Primer

<400> SEQUENCE: 7
ccagtgatat ctgtacttgt cagggcat                                       28

<210> SEQ ID NO 8
<211> LENGTH: 35
<212> TYPE: DNA
<213> ORGANISM: Artificial Sequence
<220> FEATURE:
<223> OTHER INFORMATION: Description of Artificial Sequence:Primer

<400> SEQUENCE: 8
catgctaagc ttctagaatg cttagaacca gacta                               35

<210> SEQ ID NO 9
<211> LENGTH: 35
<212> TYPE: DNA
<213> ORGANISM: Artificial Sequence
<220> FEATURE:
<223> OTHER INFORMATION: Description of Artificial Sequence:Primer

<400> SEQUENCE: 9
gatgctaagc ttctagatgg ttatgcttcg tctac                               35

<210> SEQ ID NO 10
<211> LENGTH: 17
<212> TYPE: PRT
<213> ORGANISM: Aspergillus nidulans

<400> SEQUENCE: 10

Phe Asn Asp Asp Ile Gln Gly Thr Gly Ala Val Val Met Ala Ser Leu
 1               5                  10                  15

Ile
```

```
<210> SEQ ID NO 11
<211> LENGTH: 17
<212> TYPE: DNA
<213> ORGANISM: Artificial Sequence
<220> FEATURE:
<223> OTHER INFORMATION: Description of Artificial Sequence:Primer
<220> FEATURE:
<221> NAME/KEY: modified_base
<222> LOCATION: (1)..(17)
<223> OTHER INFORMATION: Any N = Inosine

<400> SEQUENCE: 11
gaygtnggna cnaayaa                                                  17

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence:Primer
<220> FEATURE:
<221> NAME/KEY: modified_base
<222> LOCATION: (1)..(23)
<223> OTHER INFORMATION: N = Inosine

<400> SEQUENCE: 12
gtnccytgda trtcrtcrtt raa                                           23

<210> SEQ ID NO 13
<211> LENGTH: 28
<212> TYPE: DNA
<213> ORGANISM: Artificial Sequence
<220> FEATURE:
<223> OTHER INFORMATION: Description of Artificial Sequence:Primer

<400> SEQUENCE: 13
gaggatccat aggagcgcat gttggacc                                      28

<210> SEQ ID NO 14
<211> LENGTH: 27
<212> TYPE: DNA
<213> ORGANISM: Artificial Sequence
<220> FEATURE:
<223> OTHER INFORMATION: Description of Artificial Sequence:Primer

<400> SEQUENCE: 14
caggatcctc tgttagggat ttactcc                                       27
```

TRANSFORMED MICROORGANISMS WITH IMPROVED PROPERTIES

This application is the national phase under 35 U.S.C. § 371 of PCT International Application No. PCT/FI99/00185 which has an International filing date of Mar. 11, 1999, which designated the United States of America.

FIELD OF THE INVENTION

The present invention relates to genetic engineering of production microorganisms used in biotechnology to improve their properties so that they produce useful products more efficiently. In particular the invention relates to increasing the productivities of biotechnological processes and the yields of their products such as ethanol or amino acids from carbon and nitrogen sources such as biomass comprising hexoses, pentoses or their polymers.

BACKGROUND OF THE INVENTION

The efficiency of many biotechnological processes is limited by the need of production organisms to balance their metabolic redox reactions. In particular, for each of the pyridine nucleotide couples (NAD/NADH and NADP/NADPH) the total rate of oxidation must be equal to the total rate of reduction: otherwise, the couple will be completely converted into one form (e.g. all in the NAD form or all in the NADH form), and reactions requiring the other form will become infinitely slow, causing the whole metabolic network of reactions be distorted in an undesirable way (i.e., no longer provide the desired product).

For example, although the yeasts *Saccharomyces cerevisiae* and *Schizosaccharomyces pombe* are very efficient at converting hexoses into ethanol and have many advantages for this process (such as tolerance of high ethanol concentrations and other stresses) they are unable to ferment xylose to ethanol. Xylose is a major component of plants, and the inability to convert it to ethanol decreases the efficiency with which renewable biomass, such as agricultural wastes, can be utilized. However, these yeasts can utilize xylulose. Some yeasts (e.g. *Pichia stipitis*) can convert xylose to ethanol, although not very efficiently, and contain the enzymes xylose reductase (XR) and xylitol dehydrogenase (XDH). These enzymes catalyse the sequential reduction of xylose to xylitol and oxidation of xylitol to xylulose. Transformed *S. cerevisiae* strains have been constructed containing heterologous XR and XDH, which so possess a pathway to convert xylose into the fermentable xylulose (Kötter and Ciriacy [1993]; Tantirungkij et al. [1994]; Walfridsson et al. [1995]). Although these strains could use xylose for growth and xylitol formation, they did not produce much ethanol. All known XDH enzymes are specific for NAD, whereas all known XR enzymes are either specific for NADPH or have a preference for NADPH. It is believed (Bruinenberg et al. [1983]; Bruinenberg [1986]) that conversion of xylose to xylulose by this pathway therefore results in the cellular pool of NADPH being converted to NADP and that of NAD being converted to NADH, after which further metabolism of xylose is greatly hindered. The NADH can be reoxidised under aerobic conditions, but this demands critical control of oxygen levels to maintain fermentative metabolism and ethanol production. In contrast, bacteria that ferment xylose to ethanol efficiently contain xylose isomerase and convert xylose directly into xylulose without oxidation-reduction reactions. Attempts to create yeast that can efficiently convert xylose to ethanol have focused on finding or engineering XR or XDH enzymes with altered coenzyme specificity (Metzger and Hollenberg [1995]) or on expressing xylose isomerase gene in yeast. However, all reported attempts (see, e.g., Amore et al. [1989]; Ho et al. [1983]; Sarthy et al. [1987]; Walfridsson et al. [1996]) to construct good xylose-fermenting strains by expressing bacterial xylose isomerase genes in yeasts have failed.

As a second example, a major biotechnological process is the fermentation of hexose sugars to ethanol by yeast. The glycolytic pathway from glucose to ethanol is redox neutral, i.e. the amount of NAD reduced in the formation of a certain amount of pyruvate from glucose is exactly the same as the amount of NADH oxidised in the formation of ethanol from the same amount of pyruvate, and NADP(H) is not directly involved in the process. However, yeast growth is not a redox neutral process; the formation of 100 g dry yeast matter from glucose and ammonia is accompanied by the net production of 1.3 moles of NADH and 0.9 moles of NADP (Oura [1972]). This excess NADH is produced mainly by energy yielding catabolism, whereas the excess NADP is produced mainly by biosynthetic pathways (see Oura [1972]). Like other organisms, yeast has distinct pyridine nucleotide systems (NAD(H) and NADP(H)) that have evolved to facilitate these two aspects of metabolism. The excess NADH produced by fermenting yeast is reoxidised to NAD mainly by glycerol-3-phosphate dehydrogenase, resulting in the production of glycerol. In distillery fermentations this represents a wasteful diversion of 3–5% of the carbon source (Oura [1977]). Attempts to decrease the proportion of glycerol to ethanol produced during fermentations have met with little or no success. For example, Björkqvist et al. (1997) deleted each and both of the genes encoding glycerol-3-phosphate dehydrogenase. However, yeasts lacking this enzyme were not only unable to grow under anaerobic conditions, but they also stopped making ethanol.

A third example is the biotechnological production of amino acids. Amino acids have extensive applications in the food, animal feed, medical and chemical industries. Fermentation processes have been developed to produce most amino acids occuring in proteins. The metabolic routes to amino acids first convert a carbon source such as glucose into intermediates such as 3-phosphoglycerate, pyruvate, oxaloacetate or 2-oxoglutarate that are more oxidised than glucose. Their formation produces NADH. Most amino acids are more reduced than the intermediates, but the reactions leading to them from the intermediates almost invariably produce NADP. Apart from the histidine pathway, which is a net NADPH producer, and the pathways to glutamine, glutamate, tyrosine and phenylalanine, which neither consume nor produce NADPH, biosyntheses of all the other 15 amino acids from glucose produce between 1 and 8 moles of NADP per mole of amino acid and simultaneously produce NADH (Neidhardt et al. [1990]). Other reactions are then required to oxidise the NADH and reduce the NADP in order to achieve metabolic balance. This becomes a major factor with production organisms such as Corynebacteria modified and/or selected to produce huge amounts of amino acids on a commercial scale. To dispose of excess NADH, amino acid fermentations are operated under aerobic conditions, and oxygen is consumed in large amounts. To ensure maximum product formation, it is essential continuously to supply adequate amounts of oxygen, typically in the form of oxygen-enriched air (Hirose [1986]). Oxygen deficiencies, e.g., in high cell density fermentations or in cases where oxygen supplementation is uneconomical, typically result in lower product yields and productivities, as part of the carbon source is converted to compounds such as succinate, lactate or both to get rid of excess NADH.

Other examples include the enhanced biosynthesis of nucleotides, lipids and secondary metabolites by modified microorganisms selected or engineered to produce these compounds on the industrial scale. During these processes the microorganisms generally produce NADH and a central metabolic intermediate (such as pyruvate) that is more oxidised than the carbon source and reduce this intermediate to the desired product using NADPH. Once again, the microorganisms need to oxidise the excess NADH and reduce the excess NADP, and the yields on carbon source are decreased by the additional metabolic transformations of the carbon source required to achieve redox balance.

In all these examples, excess NADH is reoxidised either by respiration, requiring efficient aeration, or by the formation of unwanted side products, such as glycerol. Aeration on large industrial scales is expensive, and difficult to control exactly. In some processes, such as the fermentation of xylose to ethanol, reduction of excess NADP causes also problems. Important biochemical reactions regenerating NADPH are the oxidative branch of the pentose phosphate pathway (PPP), i.e. the successive reactions of glucose-6-phosphate dehydrogenase and 6 phosphogluconate dehydrogenase, and NADP-linked isocitrate dehydrogenase. Both reactions produce $CO_2$. In industrial scale operations, this represents both a direct loss of carbon source and an environmental pollution. Furthermore, $CO_2$ also acidifies culture media, necessitating the use of larger amounts of neutralising agents to control fermentation pH, and has a significant impact on cell physiology in general and amino acid production in particular. For example, $CO_2$ inhibits enzymes in methionine and purine biosynthesis and has been reported to inhibit product formation in several fermentation processes including production of isoleucine, inosine, fumarate, penicillin and other antibiotics and yeast biomass (Hirose [1986]).

A general method to alleviate these problems without using aeration, which is expensive and difficult to control at optimal levels, would be very beneficial. Potential benefits include increased yields on carbon source, decreased energy consumption, significant decreases in $CO_2$ production and increased specific productivity, which is particularly important in processes using immobilised microorganisms.

In the major routes of carbon and nitrogen metabolism it is a general rule that most catabolic pathways use the NAD/NADH coenzyme couple in the oxidation-reduction steps, whereas anabolic, synthetic reactions more frequently use the NADP/NADPH couple. Although the redox potentials (E'o) of these two couples are both close to −0.32 (Kaplan [1960]), the ratios of the reduced and oxidised forms of the two couples are maintained at very different levels in living cells. For example, in aerobic S. cerevisiae, NADH/NAD=0.9 and NADPH/NADP=3.2 (Sáez and Lagunas [1976]).

Most pyridine nucleotide dehydrogenases have a marked, often nearly absolute, specificity for one or the other pyridine nucleotide. Some dehydrogenases with the same substrate occur as both NAD- and NADP-specific enzymes. Usually only one of the enzymes is present under certain conditions, or the enzymes are expressed in different cell compartments. Good examples are glutamate dehydrogenases which are subject to complicated control mechanisms usually resulting in only one of the enzymes being dominant under any growth condition (e.g. Courchesne and Magasanik [1988]; Coschi-gano et al. [1991]; Miller and Magasanik [1991]; ter Schure et al. [1995]; Dang et al. [1996]; Avendano et al. [1997]). S. cerevisiae contains NAD- and NADP-linked isocitrate dehydrogenases: the cytosol (which is thought of as a single compartment) contains only NADP-linked enzyme and there is another NADP-linked enzyme in the peroxisomes whereas mitochondria (where the matrix, cristae and intermembrane space form three sub-compartments) contains both NAD- and NADP-linked enzymes (Minard et al. [1998]). Cells are therefore able to maintain NADH/NAD ratios much lower than the NADPH/NADP ratios, because reactions that transfer reducing equivalents between the two systems (and so would tend to equilibrate them) are restricted. Some bacterial and animal cells contain NAD(P) transhydrogenases (EC 1.6.1.1. and 1.6.1.2). Transhydrogenases are often membrane-bound enzymes with several subunits which are linked to energy production rather than to equilibration of the pyridine nucleotide systems. For the purposes of this patent application, the term "dehydrogenases" does not include the transhydrogenases EC 1.6.1.1 and 1.6.1.2. Many production organisms used in biotechnology, such as S. cerevisiae and Corynebacteria do not contain NAD(P) transhydrogenases, and so they appear to be unable to convert NADH plus NADP directly into NAD plus NADPH and vice versa.

The existence of two pyridine nucleotide systems and the absence of unregulated processes that would equilibrate them, suggests that the efficient growth and reproduction of presently evolved living organisms requires two distinct systems. The reason may be that a high NADPH/NADP ratio is required to drive biosynthetic reactions, whereas a lower NADH/NAD ratio is better suited for the generation of energy by pathways such as glycolysis and the tricarboxylic acid cycle (Metzler [1977]).

Boles et al. (1993) studied a mutant S. cerevisiae that lacked phosphoglucoisomerase, the enzyme that interconverts glucose-6-phosphate (Glc6P) and fructose-6-phosphate (Fru6P). This strain (a pgi1—deletion mutant) is unable to grow on any hexose or pentose, though it can grow on certain mixtures of fructose and glucose (e.g. 2% fructose plus 0.1% glucose). The authors found that transformation of the mutant with a genomic library prepared from the mutant itself resulted in certain transformants that were able to grow on glucose alone, although 3- to 4-times slower than wild type, and contained plasmids comprising the GDH2 gene. This gene encodes an NAD-linked glutamate dehydrogenase. The authors argued that the simultaneous presence of substantial activities of both NADP- and NAD-linked glutamate dehydrogenases enabled the pgi1—deletion mutant to grow on glucose by metabolising it through the PPP and converting the resulting NADPH into NADH, which could then be re-oxidised by functional mitochondria. Thus, these mutants were proposed to convert NAD plus NADPH into NADH plus NADP, which is the opposite transformation to that required of industrial production microorganisms (see above). Furthermore, their ability to survive on glucose was strictly dependent on the presence of functional mitochondria and oxygen and they were unable to ferment sugars into ethanol (Boles et al. [1993]).

SUMMARY OF THE INVENTION

According to the present invention a microorganism such as a fungus or a bacterium is transformed with at least one recombinant DNA molecule encoding or otherwise causing the expression of at least one enzyme that causes the functional coupling of the oxidation and reduction of substrates by two pyridine nucleotide-linked dehydrogenase reactions with different specificities for the NAD/NADH and NADP/NADPH coenzyme couples and so facilitates the transfer of electrons between the two coenzyme couples through the said substrates. The enzyme or enzymes can thus be one or more members of a pair of pyridine nucleotide-linked dehydrogenases that have at least one common substrate but different pyridine nucleotide specificities. Biotechnological processes in which a net oxidation of one pyridine nucleotide coenzyme couple occurs together with a net reduction of the other are carried out more efficiently by the transformed microorganism according to the invention than by the corresponding non-transformed microorganism, and the aeration of such processes can be decreased and made more flexible. These processes include the fermentation of carbohydrate to ethanol by growing microorganisms, the fermentation of xylose to useful products and the commercial production of amino acids, nucleotides, lipids and secondary metabolites by microorganisms.

Preferable microorganisms for the purposes of this invention are yeasts, filamentous fungi and bacteria. Preferable yeasts belong to the genus *Saccharomyces*, and are especially strains of the species *Saccharomyces cerevisiae*; the genus *Schizosaccharomyces*, and are especially strains of the species *Schizosaccharomyces pombe*; and the genus *Pichia*, and are especially strains of the species *Pichia stipitis*, as well as *Candida* spp. or *Pachysolen* spp. Useful filamentous fungi include e.g. *Trichoderma, Aspergillus, Neurospora, Fusarium, Paecilomyces* and *Penicillium*. Particularly suitable bacterial genera include Corynebacteria, especially the strains *Corynebacterium glutamicum*, as well as Brevibacteria, such as *Brevibacterium flavum* and *B. lactofermentum*.

BRIEF DESCRIPTION OF THE DRAWINGS

FIG. 2. Alignment of the amino acid sequence deduced from a partial sequence of the gene encoding the malic enzyme of *Aspergillus nidulans* (SEQ ID NO: 1) with some known malic enzymes. The database numbers (SwissProt) for the known malic enzymes are: P23368 (human malic enzyme (SEQ ID NO: 3)), P40375 (*S. pombe* malic enzyme (SEQ ID NO: 4)), P36013 (*S. cerevisiae* malic enzyme (SEQ ID NO: 5)). Partial sequence of the gene encoding the malic enzyme of *Trichoderma reesei* (SEQ ID NO:2) was at VTT, Biotechnology and Food Research. Amino acids identical at least in three of the sequences are shadowed in grey.

DETAILED DESCRIPTION OF THE INVENTION

Figure 1:
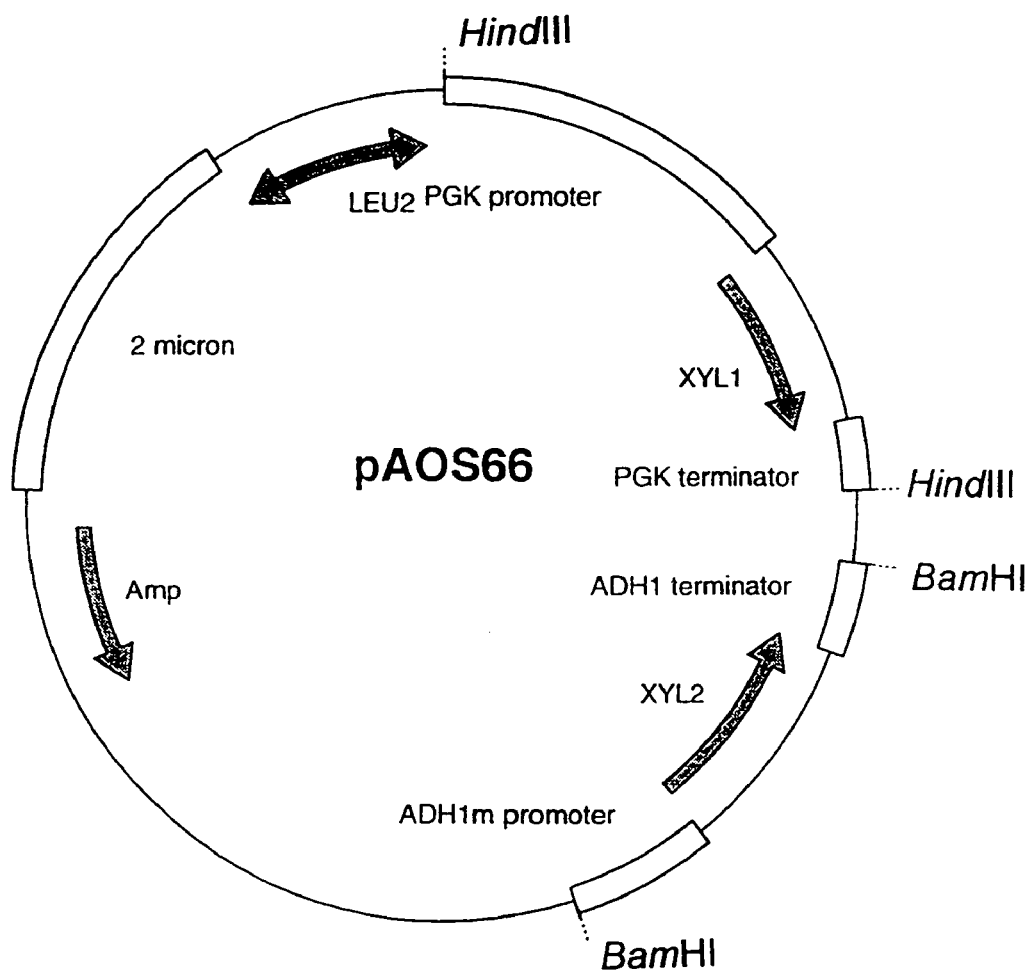
FIG. 1. The genetic map of pAOS66 with the relevant genes, expression cassettes and restriction sites indicated.

The central teaching of the present invention is a method to enhance biotechnological processes by transforming production microorganisms with genes for enzymes that tend to equilibrate the two pyridine nucleotide systems that coexist in living cells. Surprisingly, although cells have evolved two distinct pyridine nucleotide systems, which are maintained at distinct redox potentials, and such equilibration reactions are apparently prohibited in naturally evolved cells, it is now disclosed that these reactions promote the metabolic pathways desired for product formation by the engineered or selected microorganisms used in many biotechnological processes, and thereby benefit those processes.

In its first embodiment the present invention provides a microorganism which is transformed with at least one recombinant DNA molecule encoding or otherwise causing the expression of at least one of a pair of dehydrogenases with opposite coenzyme specificities for NAD/NADH and NADP/NADPH but at least one common substrate (S in equations (1) and (2)) in such a way that both members of the pair are simultaneously expressed in the same subcellular compartment, preferably the cytosol. This results in a functional coupling of the dehydrogenases catalysing reactions (1) and (2). It is not a necessary part of the invention, but neither is it excluded, that the two dehydrogenases should physically associate within the transformed cell. The functional coupling allows the following reactions to occur, which tend to equilibrate the NAD/NADH and NADP/NADPH coenzyme couples:

(1)

Simultaneous operation of reactions (1) and (2) might be expected to proceed until the NAD/NADH and NADP/

NADPH ratios are almost identical, because the redox potentials of the two couples are very similar. However, the inventors show here that when production microorganisms are transformed in this way, the efficiency with which raw material is converted into useful products and the yields of products on biomass are substantially increased.

It is to be noted that the tendency to equilibrate the two pyridine nucleotide couples brought about by reactions (1) and (2) (and also by reactions (3) to (5), (6) to (8) and (11) to (12) below) is caused by transfer of electrons through the substrates of pyridine nucleotide-linked dehydrogenases ($SH_2$ in reactions (1) and (2) and reactions (3) to (5), malate in reactions (6) to (8) and glutamate in reactions (11) and (12)). This distinguishes the present invention from systems in which electrons are transferred from NAD(P)H to NAD(P) by so-called transhydrogenases (e.g., EC 1.6.1.1 and 1.6.1.2). Kojima et al. (1996: EP 0 733 712 A1) have described a system in which transhydrogenase may be utilised in certain bacteria as a means of converting NADH generated through the TCA cycle into NADPH.

Several pairs of dehydrogenases are known which share common substrates but have different pyridine nucleotide specificities. For example, there are both NAD- and NADP-linked forms of glutamate dehydrogenase (EC 1.4.1.2 and 1.4.1.4), isocitrate dehydrogenase (EC 1.1.1.41 and 1.1.1.42), aldehyde dehydrogenase (EC 1.2.13 and 1.2.1.4), alcohol dehydrogenase (EC 1.1.1.1 and 1.1.1.2), malate dehydrogenase (EC 1.1.137 and 1.1.1.82), glycerol-3-phosphate dehydrogenase (EC 1.1.1.8 and 1.1.1.94), xylose-1 dehydrogenase (EC 1.1.1.175 and 1.1.1.179), glyceraldehyde-3-phosphate dehydrogenase (EC 1.2.1.12 and 1.2.1.13), orotate reductase (EC 13.1.14 and 13.1.15) and ferredoxin reductase (EC1.18.1.2 and 1.18.13) but any appropriate pair of dehydrogenases may be used. Many dehydrogenases are known (see for example Enzyme Nomenclature 1992, Academic Press Inc.) and their properties can be found from the literature or determined by simple spectrophotometric assays (see, e.g. Bergmeyer [1974]). Besides naturally occuring enzymes with the desired pyridine nucleotide specificities, the invention also includes the use of genetically engineered enzymes with altered pyridine nucleotide specificities. As an example of cofactor specificity changes, see e.g. Chen et al. (1994) and Chen et al. (1997).

The catalytic activities responsible for reactions (1) and (2) may occur in the same polymeric protein or even in a single polypeptide chain or be combined into such a polymeric protein or single polypeptide chain, for example by genetic engineering. The invention may also be realised by overexpressing a dehydrogenase that operates effectively with both pyridine nucleotide systems. Dehydrogenases that accept both pyridine nucleotides are known and include isozymes of glutamate dehydrogenase (EC 1.4.1.3), aldehyde dehydrogenase (EC 1.2.1.5) and alcohol dehydrogenase (EC 1.1.1.71). Little is known about how their activities are regulated in vivo so that they do not disturb the concentrations of pyridine nucleotides.

In its second embodiment the invention provides a microorganism which is transformed with at least one recombinant DNA molecule encoding or otherwise causing the expression of at least one enzyme that catalyses at least one step of a cyclic series of reactions in which NADP is reduced to NADPH and NADH is oxidised to NAD, or vice versa. Reactions (3) to (5) show one such cycle:

  (3)

  (4)

  (5)

In the direction written, reactions (3) to (5) convert NADP plus NADH to NADPH plus NAD, and in the opposite direction they carry out the opposite transformation. The enzymes catalysing reactions (3) and (5) are again a pair of dehydrogenases with a common substrate ($SH_2$) but opposite coenzyme specificities, as in the first embodiment of the invention, but now the reaction products (S and Z) are different. For the purposes of this invention, reaction (4) can be a series of steps instead of a single step, provided only that S is converted into Z without a net change in NAD or NADP. Thus, this series of reactions also tends to equilibrate the NAD/NADH and NADP/NADPH couples in the same way as reactions (1) and (2), except that this is now coupled to the transformation of X Y. Thus, at equilibrium it is not necessarily the case that the NAD/NADH and NADP/NADPH ratios will be nearly equal: instead they will also depend on the equilibrium between X and Y. An example of this embodiment of the invention is provided by malic enzyme, pyruvate carboxylase and malate dehydrogenase, which catalyse the following reactions:

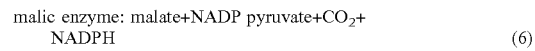  (6)

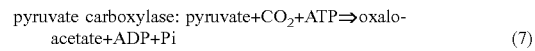  (7)

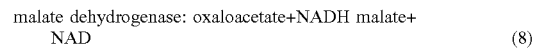  (8)

In reactions (6) to (8), pyruvate+$CO_2$ correspond to S in reactions (3) to (5), oxaloacetate corresponds to Z and ATP and ADP+Pi, respectively, correspond to X and Y.

In reactions (3) to (5) the reduced substrate, $SH_2$, is common to the two dehydrogenases. The invention can also be practised by transforming a microorganism with one or more enzymes to create a cyclic series of reactions (3') to (5') in which the oxidised form of the substrate is common to the two dehydrogenases:

  (3')

  (4')

  (5')

Once again, for the purposes of this invention the reaction (4') can be a series of steps instead of a single step, provided only that $SH_2$ is converted into $ZH_2$ without a net change in NAD or NADP.

Further, it is now an obvious extension of the invention to combine the cyclic schemes (3) to (5) and (3') to (5') so that neither the oxidised nor the reduced forms of the substrates are common to the two dehydrogenases, but the oxidised forms of the substrates of the dehydrogenases can be interconverted by reactions with no net redox change and so can the reduced forms:

  (3")

  (4")

  (5")

Thus, in its most general form the invention consists of transforming a micro-organism with a gene causing expression of at least one enzyme catalysing one of the reactions (3") to (5") so that all these reactions can occur in the same cell compartment. When the reactions occur from left to right as written above, reducing equivalents are transferred from NADH through $ZH_2$ and $SH_2$ to NADP, reducing it to NADPH. When the reactions occur from right to left, NADH is formed at the expense of NADPH.

Also in this embodiment of the invention, it is envisaged that a genetically engineered enzyme with changed coenzyme specificities can be used.

In the first specific aspect of the invention, the host microorganism carries an XR enzyme which preferentially uses NADPH, and an XDH enzyme which preferentially uses NAD. The host microorganism can convert xylose into xylulose by these enzymes, but as described above, this process is inefficient and yields of ethanol on xylose are low or zero. An example of this aspect of the invention is provided in Example 8. An engineered strain of S. cerevisiae carrying genes for XR and XDH, and xylulokinase (XK), is transformed with a multicopy plasmid carrying the gene GDH2 encoding the NAD-dependent glutamate dehydrogenase from S. cerevisiae, and a marker gene. Transformants are selected by means of the marker gene. The transformants ferment xylose to ethanol more efficiently than the non-transformed host yeast, in particular with a higher yield of ethanol on xylose, or less $CO_2$ production or both. Depending on the chosen process conditions, the improved efficiency can also be realised in other ways, such as an increased volume productivity or enhanced specific rate. Enhanced specific rate is especially significant in processes utilizing immobilised microorganisms, where there is an upper limit to the amount of biomass that can be held by the carrier material. The increased efficiency may be explained by the following sequence of reactions:

 xylose+NADPH⇒xylitol+NADP (9)

 xylitol+NAD⇒xylulose+NADH (10)

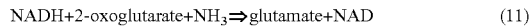 NADH+2-oxoglutarate+NH₃⇒glutamate+NAD (11)

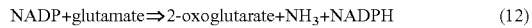 NADP+glutamate⇒2-oxoglutarate+NH₃+NADPH (12)

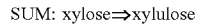 SUM: xylose⇒xylulose

Thus, the redox imbalance is avoided, and a smooth conversion of xylose to xylulose can take place. The flux through decarboxylation reactions, such as G6PDH and isocitrate dehydrogenase to regenerate NADPH is decreased, with decreased $CO_2$ production, and the fermentation occurs efficiently, and without aeration. Rather surprisingly, xylitol production was also increased by about 25% in the strain transformed according to the invention with GDH2 by comparison to the control strain. This increase in xylitol is discussed below.

In this example, the host microorganism had already been transformed with genes encoding XR, XDH and XK. It is not a requirement of the invention that the host organism is itself a transformant. It is remarkable that the invention causes a substantial increase in ethanol yields with the host microorganism of Example 8, because the XR in this host is the enzyme from P. stipitis, which is able to work with NAD(H) although it has a preference for NADP(H) (Verduyn et al. [1985]). Thus, this aspect of the invention is realised even with an XR that can use NADH. A more substantial effect can occur when the host organism contains an XR with higher specificity for NADP(H), such as when the S. cerevisiae open reading frame XHR 104 w encoding XR activity is highly expressed. Furthermore, it has been claimed that transformation of yeasts with an gene encoding XK improves the efficiency with which they ferment xylose to ethanol (Ho and Tsao, WO 95/13362). It is notable that the present invention causes an improved fermentation of xylose to ethanol even when the host organism contains elevated levels of XK. However, the invention provides improved fermentation of xylose to ethanol also in host organisms that have not been transformed with a gene encoding XK. It is now known that yeasts such as S. cerevisiae and Schiz. pombe contain homologous genes encoding XDH, XK and (S. cerevisiae) XR. The ability of a host yeast that does not contain any heterologous gene for XR, XDH or XK to ferment xylose to ethanol can also be usefully enhanced by transformation according to the present invention.

Various enzymes, including isomerases and epimerases, are known that interconvert the different pentose sugars and different pentose phosphates. It will be understood by a person skilled in the art that the present invention provides a general method to improve the efficiency of ethanol production, not only from xylose but also from other pentoses.

It will be understood by a person skilled in the art that similar beneficial effects can be obtained by using other pairs of dehydrogenases according to the first embodiment of the invention described above. For example, instead of transforming S. cerevisiae with GDH2 so that both NAD- and NADP-linked glutamate dehydrogenases are adequately expressed in the cytosol, the same effect can be achieved by transforming the yeast with one or both members of another pair of dehydrogenases that share the same substrates but use different pyridine nucleotides, provided that both of the enzymes are reversible, or at least that they catalyse the reactions in the directions shown in equations (11) and (12). For example, most NAD-linked isocitrate dehydrogenases are allosteric enzymes that cannot catalyse the reductive carboxylation of 2-oxoglutarate (corresponding to reaction (11)), but only the oxidative decarboxylation of isocitrate, and would therefore be unsuitable for this aspect of the present invention. However, several other pairs of dehydrogenases can be used, including alcohol and aldehyde dehydrogenases. Appropriate information can be obtained from the literature or readily determined by testing with simple spectrophotometric assays. The activities of dehydrogenases can be easily measured in both directions, provided that they are reversible, by following the appearance or disappearance of NAD(P)H in the presence of the appropriate substrates to determine whether candidate enzymes catalyse the reactions required to relieve the coenzyme imbalance.

According to the second embodiment of the present invention, similar beneficial effects can be obtained by transforming S. cerevisiae with a recombinant DNA molecule encoding an NAD(P)-linked malic enzyme. S. cerevisiae already contains pyruvate carboxylase and malate dehydrogenase. The yeast can now catalyse the reactions (6) to (8) as shown above, resulting in the conversion of NADP plus NADH into NADPH plus NAD. Example 14 illustrates the beneficial effects of this transformation. Compared to the control strain, the strain overexpressing the gene for malic enzyme exhibited a 55% greater specific rate of xylose utilization and 20% and 25% greater specific rates of ethanol and xylitol formation.

The increased rates of xylitol formation observed in Examples 8 and 14 by strains constructed according to the first and second embodiments of the invention were unexpected, because these particular strains contained also heterologous XDH and XK. XDH and XK are known to assist the conversion of xylose to ethanol, so these strains were a good test to show that the present invention can further improve xylose fermentation to ethanol under realistic conditions. XDH and XK are expected to facilitate the conversion of xylose-derived xylitol to xylulose-5-phosphate, so it is significant that even in the presence of these two enzymes, transformation according to the present invention increased xylose uptake by more than it increased ethanol production, the difference appearing as an increase in xylitol production. Xylitol is an attractive product, either by itself or together with ethanol. Transformation according to the invention of strains that do not contain heterologous XDH and XK is expected to provide at least as good improvements in xylitol production as those achieved in Examples 8 and 14.

Yeasts and other microorganisms produce other pentitols, in particular arabitol and ribitol, as well as xylitol. These can be produced from other natural pentoses (e.g. arabinose) that occur in raw materials, or by metabolic intercoversions of pentitols that often proceed through dehydrogenase reactions with differing coenzyme specifity (see, e.g., Chiang & Knight [1960]). In either case, similar redox balance problems occur as those described above, and improved productivities and yields can be obtained by practise of the present invention.

It will be understood by a person familiar with the art that because it exploits fundamental biochemical principles the present invention has very broad application and can be practised in other microorganisms as well as S. cerevisiae. Example 18 illustrates that transformation of Schiz. pombe with the gene encoding malic enzyme according to the invention improves the efficiency of the fermentation of xylose to ethanol. Volumetric and specific productivities were significantly enhanced also with this microorganism, and importantly it was able to maintain its biomass and metabolic capacity under the process conditions, whereas the biomass of the control strain decreased relatively rapidly.

In another specific aspect of the invention, the host microorganism ferments hexose sugars to ethanol. Because the microorganism grows during the fermentation it produces excesses of both NADH and NADP (Oura, [1972]). With the non-transformed microorganism, ethanol production is accompanied by glycerol production, which is required to reoxidise the excess NADH, and by the production of more than one mole of $CO_2$ per mole of ethanol, which is required to reduce the excess NADP. These reactions decrease the yield of ethanol on fermentable carbohydrate. With the transformed microorganism, the yield of ethanol on fermentable carbohydrate is increased compared to that of the non-transformed microorganism. Illustrations of this aspect of the invention are provided in Examples 9 and 13.

In Example 9 the yeast S. cerevisiae is transformed with a multicopy plasmid comprising the gene GDH2 encoding the NAD-dependent glutamate dehydrogenase from S. cerevisiae and a marker gene. The transformants are selected by means of the marker gene. The transformants ferment glucose to ethanol with improved efficiency, in particular an improved yield of ethanol on fermentable carbohydrates and with decreased production of some unwanted side products, including $CO_2$. Depending on the chosen process conditions, the improved efficiency can also be realised in other ways, such as an increased volume productivity or increased specific rate. This may be explained by the following sequence of reactions that converts substantial parts of the excess NADH and NADP into NAD and NADPH without unwanted consumption of fermentable sugars:

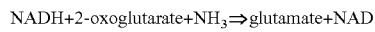

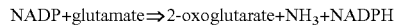

In Example 13, S. cerevisiae is transformed with a gene encoding malic enzyme according to the second embodiment of the invention. Significant advantages are achieved, including again decreased production of (undesired) biomass and increased specific rate of ethanol production.

It will be understood by a person skilled in the art that similar beneficial effects on hexose fermentation to ethanol can be obtained by using other pairs of dehydrogenases according to the first embodiment of the invention disclosed above or by using other appropriate enzymes according to the second embodiment of the invention and that the invention can be practised with other microorganisms as well as S. cerevisiae.

It is a significant part of the invention that the same transformation that increases the efficiency of xylose fermentation to ethanol (Examples 8, 14 and 18) also increases the efficiency of hexose fermentation to ethanol (Examples 9 and 13). Thus, the invention simultaneously provides improved utilization of both glucose and xylose, which are major sugars derived from many renewable biomasses, such as agricultural and forest materials and urban waste.

For industrial production of ethanol, the present invention is preferably practised using an industrial strain, e.g. a distiller's or brewer's yeast, or a wine yeast, or a strain of Schiz pombe used for rum production. Methods to transform industrial yeasts, which are often polyploid and lack auxotrophic markers are well known. An early review of such methods was made by Knowles and Tubb (1987). The industrial strain transformed according to the invention is then used for example in the same industrial fermentation process as the non-transformed strain and provides the advantages disclosed above, such as increased yield, increased productivity and decreased undesirable side-products. Compared to the non-transformed strain, the transformed strain can also be used advantageously for the economic fermentation of a wider range of raw materials, such as raw materials with high levels of pentoses, pentose polymers or both.

In a third specific aspect of the invention a microorganism that overproduces an amino acid such as alanine, valine, leucine, isoleucine, serine, threonine, lysine, arginine, tryptophan, cysteine, methionine or proline is transformed with at least one recombinant DNA molecule encoding at least one of a pair of dehydrogenases with opposite pyridine nucleotide specificities (i.e., according to the first embodiment of the invention), or with at least one recombinant DNA molecule encoding at least one enzyme that catalyses at least one step of a cyclic series of reactions in which NADP is reduced to NADPH and NADH is oxidised to NAD according to reactions (3) to (5), (3') to (5') or (3") to (5") (i.e. according to the second embodiment of the invention). The transformed microorganism can produce the desired amino acid with improved efficiency, in particular with increased yield on carbon source, with increased productivity, with a decreased requirement for aeration, with decreased production of carbon dioxide or with several of these benefits.

For example, lysine is presently produced by microbial fermentation processes that are mainly based on various Corynebacteria, such as Corynebacterium glutamicum and Brevibacterium flavum. Genetic techniques for these bacteria are well developed (see, e.g., Follettie et al. [1991]; Follettie & Sinskey [1986]; Jetten et al. [1994]; Jetten & Sinskey [1995]) and DNA vectors are available for the transformation of these production organisms efficiently by either multicopy plasmids or chromosomal integration. For example, available vectors include pAJ655, pAJ1844 and pCG11 for use with C. glutamicum, Brevibacterium spp., and Escherichia coli or the pAJ440 plasmid vector for use in Bacillus subtilis, Brevibacterium spp., and C. glutamicum, or the pMS2 plasmid vector for use in *Rhodococcus* spp., *Corynebacterium* spp., and *E. coli*. The effects of transformation of lysine-producing strains according to the present invention can be realised in strains such as ATCC 31269, ATCC 21253, ATCC 21800, ATCC 21801 or ATCC 21086 or in other strains that overproduce lysine or other amino acids and are used industrially.

This aspect of the invention is illustrated in Examples 19 to 23. *Corynebacterium glutamicum* was transformed with a gene from *Peptostreptococcus asaccharolyticus* encoding an NAD-dependent glutamate dehydrogenase. The transformed *Corynebacterium glutamicum* shows NAD-linked glutamate dehydrogenase activity, and this organism naturally possesses NADP-linked glutamate dehydrogenase activity. The transformed organism therefore possesses a dehydrogenase pair according to the first embodiment of the invention that can convert NADP plus NADH into NAD plus NADPH. Unlike some bacteria, *Corynebacterium glutamicum* does not contain NADP/NADH transhydrogenase, so the sequential operation of the two glutamate dehydrogenases provides the bacterium with the novel means to equilibrate the NAD/NADH amd NADP/NADPH coenzyme couples. It is well known that the synthesis of lysine (and most other amino acids) produces NADP, and when lysine is overproduced in large amounts the requirement for reduction of NADP to NADPH can limit amino acid production. It is also known under the cultivation conditions used in Example 23, production of lysine does not begin while threonine is still present in the medium and that yields are relatively low until the bacteria stops growing (Vallino, J. J. [1991]; see especially pages 207 to 213). Surprisingly, *Corynebacterium glutamicum* transformed according to the invention already produced large amounts of lysine while threonine was still present and before the bacterium had reached even 25% of the expected biomass yield. These examples disclose that the present invention can be practiced with advantage also in bacteria as well as fungi and for improving the production of amino acids as well as non-nitrogenous compounds such as ethanol and xylitol.

For the industrial production of amino acids, a bacterial strain that overproduces one or more amino acids is transformed according to the invention. The transformed strain can be used in the same industrial processes as the parent non-transformed strain. For example, raw materials can be used that comprise any of a variety of sugars or organic acids such as citric, succinic or fumaric acid as carbon source and ammonia, ammonium salts or inexpensive protein hydrolysates as nitrogen source. Trace organic (e.g. thiamine) and inorganic (e.g. iron and manganese salts) materials can be added in the same way as for the original process with the parent non-transformed strain. Compared to the non-transformed strain, the strain transformed according to the present invention provides the advantages disclosed above, such as increased yield, increased productivity, decreased oxygen requirement.

An NAD-linked glutamate dehydrogenase can also be introduced to *Corynebacterium glutamicum* (and other *Corynebacteria* spp.) by any method well known in the art. For example, the gene from *Peptostreptococcus* asaccharolyticus has been transferred to C glutamicum under a Tac promoter by Marx et al. (1999). Significantly, these workers used a strain of *Corynebacterium glutamicum* from which the gene coding for NADP-linked glutamate dehydrogenase was first deleted, whereas the present invention teaches the simultaneous presence of NADP-linked and NAD-linked glutamate dehydrogenases. The invention can also be practised by transforming bacterial strains that overproduce other amino acids than lysine with this or another gene encoding NAD-linked glutamate dehydrogenase or with the gene for some other enzyme that causes the functional coupling of two dehydrogenases with different specificities for the pyridine nucleotide couples.

Polyhydroxyalkanoates (PHAs) are commercially produced to make biodegradable plastics, but prices are too high for widespread use except where this is enforced by legislation (e.g. in Germany). It is therefore desirable to improve the efficiency of the microbial processes producing PHAs. In the biosynthesis of PHAs, glucose is metabolised to acetyl-CoA, producing 2 NADH molecules/acetylCoA molecule, and the acetylCoA is then condensed to acetoacetylCoA which is reduced by NADPH to 3-hydroxybutyrylCoA. Synthesis of each molecule of 3-hydroxybutyrylCoA therefore produces 4 molecules of NADH and requires 1 molecule of NADPH. The 3-hydroxybutyrylCoA is then polymerised to polyhydroxybutyrate (PHB) or copolymerised with other acylCoAs such as propionylCoA to form mixed PHAs. The requirement for one NADPH molecule and production of 4 NADH molecules per monomer unit means that microorganisms synthesising PHAs need to divert part of their carbon flux through reactions such as glucose-6-phosphate dehydrogenase or isocitrate dehydrogenase in order to generate NADPH, with consequent excess production of $CO_2$ and waste of carbon source, as explained above. At the same time, NADH must be reoxidised, causing either further carbon losses or increased oxygen demand or both. This waste can be decreased by transforming the production microorganism according to the present invention, so providing it with a novel mechanism that converts part of the excess NADH produced into the NADPH required (for reviews, see e.g. Anderson and Dawes [1990]; Poirier et al. [1995]).

In this aspect of the invention, a microorganism that produces one or more PHAs is transformed according to the first or second embodiments, and the transformed microorganism is used to ferment glucose in the presence or absence of organic acids such as propionic or valeric acids. Compared to the non-transformed parent organism, the organism transformed according to the invention provides the advantages disclosed above, such as producing increased yields of PHA on glucose, increased productivities and decreased formation of unwanted sideproducts, such as $CO_2$. Example 24 illustrates how this can be done. In this example the production microorganism is a recombinant strain *Saccharomyces cerevisiae* transformed with the PHB synthase and reductase genes from *Alcaligenes eutrophus*. However, it is not necessary that a recombinant yeast is used. Any microorganism producing PHAs can be used, e.g. *Alcaligenes eutrophus* or *Pseudomonas oleovarans*, or engineered bacterial strains that over-produce PHAs. The microorganism transformed according to the present invention is then used to ferment glucose with or without organic acids under essentially the same process conditions as used for the non-transformed parent organism.

Figure 8:
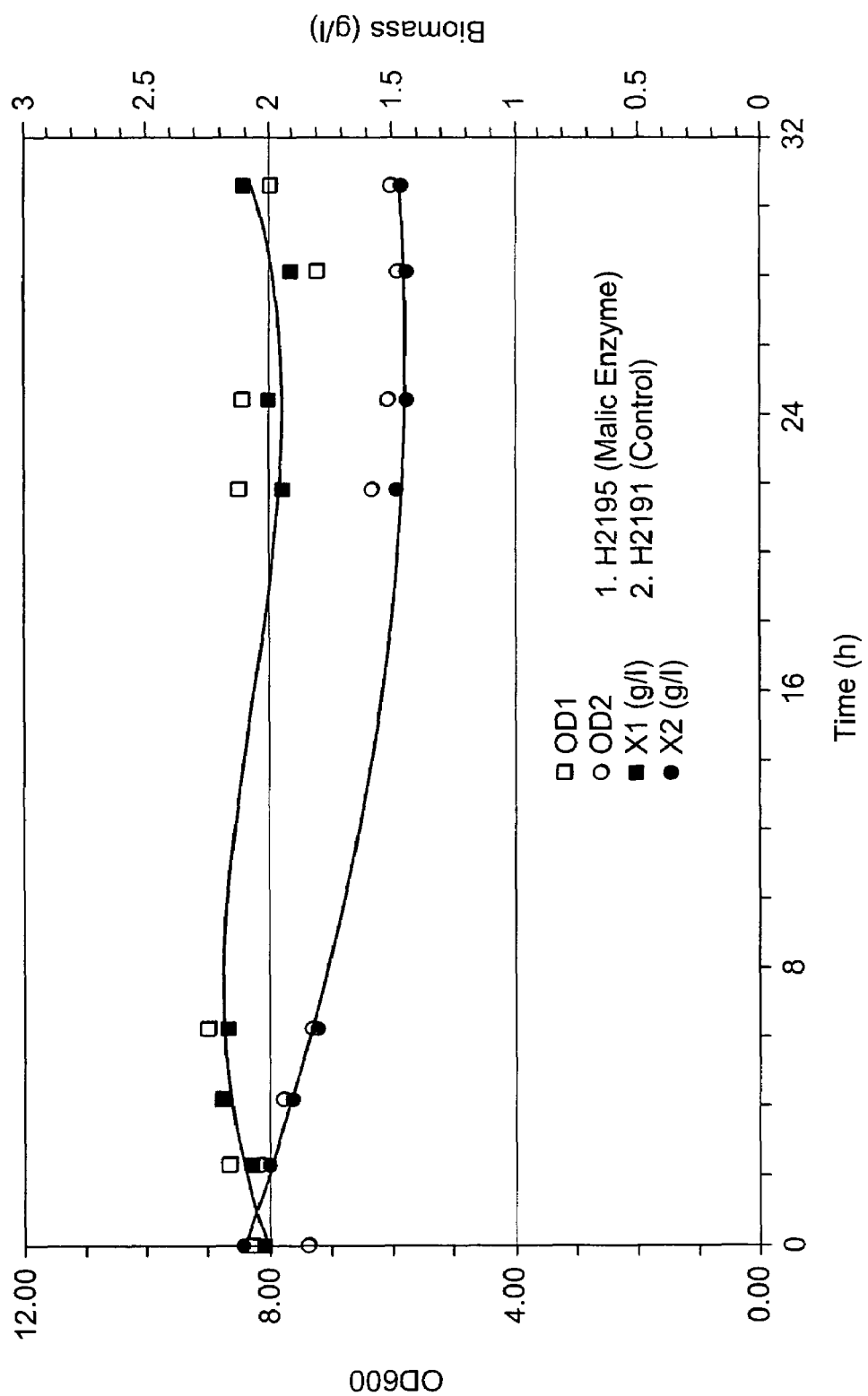
FIG. 8. Biomass profiles for xylose batch fermentations of *Saccharomyces cerevisiae* recombinant strain expressing MAE1 (H2195) and control strain (H2191)

In another aspect of the invention a production microorganism is transformed according to the invention and under the conditions of a biotechnological process, the transformed microorganism maintains a higher level of the metabolic capacity required for the said process than does the corresponding non-transformed microorganism. Example 14 illustrates this aspect. *S. cerevisiae* transformed according to the invention with a gene expressing malic enzyme is used to ferment xylose to ethanol under anaerobic conditions, which are advantageous because they prevent a decrease caused by oxidative processes in the yield of ethanol. Under these process conditions the biomass of the control strain decreases with time during operation of the process with a corresponding loss of its metabolic capacity to convert substrate (xylose) into product (ethanol). In practice this would lead to inconvenient and expensive process requirements such as repeated addition of more production organism. However, the organism transformed according to the invention is able to maintain its biomass and the metabolic capacity required by the process (FIG. 8). Presumably this is because the transformed organism is able to obtain sufficient energy from the biotransformation of the process (in the case of Example 14, the conversion of xylose to ethanol) to maintain its own integrity and metabolic capacity, whereas the non-transformed organism cannot. Under the conditions of Example 14, with a unicellular production microorganism and a homogenous liquid medium, it was easy to demonstrate the decrease in biomass of the control microorganism and the maintenance of the biomass of the organism transformed according to the invention.

However, it is clear to a person familiar with the art first that in many processes, e.g., those employing inhomogenous media or filamentous fungi or both, it can be very difficult to demonstrate the maintenance of biomass, and second that the significant parameter is not the biomass itself but its metabolic capacity to convert the substrate of the process into the product. In this connection metabolic capacity means the total ability of the production organism present in a process (e.g. per unit volume of a fermentor) to perform a particular set of biotransformations, namely those required by the particular biotechnological process, and it can be measured by measuring the rate of conversion of process substrate into process product under standard conditions.

Other aspects of the invention include the transformation of production microorganisms that have been developed to overproduce nucleotides, lipids or secondary metabolites of various types on an industrial scale. After transformation according to the above described embodiments of this invention, these microorganisms will provide increased yields of the desired commercial products, or increased specific production rates, decreased formation of undesirable side products (such as $CO_2$ or excess biomass) or several of these advantages simultaneously.

These examples disclose how the efficiency of biotechnological processes can be improved by transforming production microorganisms with at least one recombinant DNA molecule encoding enzymes that facilitate oxidation-reduction reactions between the NAD(H) and NADP(H) coenzyme systems. The invention can be realised by transforming the host with a single gene (e.g. GDH2 in Example 3; MAE1 in Example 12) and using enzymes that are naturally expressed in the host under the specific production conditions to complete the reaction schemes (i.e. reactions (1)+(2) or (3)+(4)+(5) above). However, the invention can also be realised by transforming the host with more than one DNA-molecule so that both reactions (1) and (2) or two or more of the reactions (3), (4) and (5) (or (3'), (4') and (5'), or (3"), (4") and (5")) are performed by enzymes expressed from transformed genes.

Besides GDH2 and a gene encoding malic enzyme, genes encoding other enzymes can be advantageous. Suitable enzymes (examples are given above) are known and their genes have been cloned and can be found in data banks and obtained by PCR methods well known in the art (Examples 6 and 7 and 10 confirm how readily this can be done for genes from both yeast and filamentous fungi). A person skilled in the arts of microbial physiology and metabolism can plan a metabolic scheme corresponding to reactions (1) and (2), or (3) to (5), (3') to (5') or (3") to (5"). Many such schemes require well known enzymes. Data banks (e.g. Swissprot) can also be searched to find the requisite enzyme or enzymes. Thus, for example, the following accession numbers provide amino acid or nucleotide sequences corresponding to NADP-linked dehydrogenases: P00369, P31026, P00370, P50216, P08200, P14941, P75214, P27800, Q58820, P15719, P46919, P28861, L05667, U26463, YPL061w, P18819, M88600, X75327 and P55804. These sequences can be used to clone the corresponding genes, e.g., by PCR with sequence specific primers.

Other suitable enzyme activites can be found by carrying out appropriate enzyme assays (see, e.g., Bergmeyer [1974], but other suitable assay systems can be readily designed by a person skilled in the art) on extracts prepared from suitable organisms, including bacteria, fungi and higher plants and animals. The responsible protein can then be purified by standard methods, and antibodies prepared against it or amino acid sequence data obtained from it. The gene encoding the protein can then be cloned by standard methods such as using antibodies to screen expression libraries or oligonucleotides designed from the amino acid sequences to act as primers in PCR cloning or hybridization probes to screen gene banks.

Suitable new enzyme activities and their genes can also be found by exploiting data bank information in other ways that are familiar and routine to people skilled in the art. For example, alignment of several sequences encoding malic enzymes reveals a so called "malic enzyme signature", which allows the preparation of oligonucleotide mixtures that can be used, for instance, in PCR cloning of genes encoding malic enzymes in other organisms, as is described in Example 7 for the malic enzyme of *Aspergillus nidulans*.

It is well known to a man skilled in the art that during the cloning of genes by PCR, point mutations can occur and be perpetuated by the amplification technique. Small sequence differences between the same genes in different strains of the same organism can also occur naturally. Many of these changes have no significant effect on the function of the encoded protein and are therefore called neutral mutations. For example, two point mutations in the gene encoding malic enzyme were observed in Example 10, but did not significantly affect the activity of the encoded malic enzyme. Such neutral mutations can also be introduced deliberately. Our invention encompasses the use of such neutral variants of genes as well as the natural genes.

According to the present invention, the host organism is transformed in such a way that the reactions (1) and (2) in the first embodiment of the invention or the reactions (3) to (5) (or (3') to (5') or (3") to (5")) in the second embodiment occur simultaneously preferably in the same subcellular compartment, preferably the cytosol. The restriction that the reactions occur in the same compartment is not absolute because reactions (4") can include transport or shuttle reactions moving metabolic intermediates between subcellular compartments. The invention teaches that the transforming gene can be modified if necessary to cause expression in the appropriate compartment and under the physiological conditions prevailing during the desired production process. So called "signal" or "targeting" sequences are known that usually encode relatively short N-terminal or C-terminal amino acid sequences that direct proteins to specific compartments such as mitochondria, peroxisomes or periplasmic space (McAlister-Henn et al. [1995]). These sequences can be readily removed or added to genes by standard techniques of genetic engineering to cause the desired enzymes to be expressed in the desired compartment. Malic enzyme expressed from the complete MAE1 gene (as in Examples 13, 14 and 18) is an example of an enzyme with a mitochondrial targeting sequence (Boles et al. [1998]), so that at least some of its activity is expected to be located inside mitochondria. When the gene is strongly expressed, as in Examples 13 and 14 it is likely that a part of the enzyme remains in the cytosol, where also the yeast malate dehydrogenase and pyruvate carboxylase are found. If it is desired to express the malic enzyme (or some other enzyme with a mitochondrial targeting sequence) only in the cytosol, then the targeting sequence can be removed by truncating the gene appropriately. In addition, enzymes subject to catabolite inactivation can be modified to slow or prevent this regulatory circuit (Minard and McAlister-Henn [1992]).

The present invention can also be practised by transforming a microorganism with a recombinant DNA molecule so that the natural promoter of a host gene encoding a suitable enzyme that catalyses one of the reactions (3") to (4") is replaced by another promoter that can cause stronger expression or expression under different physiological conditions than the said natural promoter. It is not necessary that the transforming DNA molecule contains a nucleotide sequence encoding a complete functional enzyme. For example, the beneficial effect can be obtained by transforming the host S. cerevisiae with a DNA molecule that only replaces through recombination in vivo the natural promoter of the host's GDH2 with a promoter such as PGK or ADH, so that the host's NAD-dependent glutamate dehydrogenase is constitutively expressed. When the host is transformed with a gene from another organism, it is desirable to use a promoter derived from the host.

For many production fungi and bacteria suitable promoters are known. Examples include the promoter of the S. cerevisiae PGK, ACT, ENO1, GAPDH, MET genes, such as ME725 and ADH promoters, and modified versions thereof (e.g. Ruohonen et al. [1995]; Beier and Young [1982]). It is envisaged in the invention that, in the case of S. cerevisiae for example, use of these promoters can be advantageous even when the transformed gene or genes are obtained from yeast. They can be advantageous especially when the genes are to be integrated into the host's genome, because these promoters are known to cause adequate expression over a range of physiological conditions. For example, the so called middle length ADH1 promoter causes efficient expression in S. cerevisiae under both fermentative and gluconeogenic growth conditions. However, adequate expression of the transformed gene or genes can also be obtained with the genes' natural promoters, for example, by transformation with a multicopy plasmid, as disclosed in Examples 3 to 5. Efficient expression under desired physiologoical conditions can also be obtained by modifications of the promoter in question or by modifications of the transacting regulatory mechanisms (negative or positive) involved in the expression of the particular gene.

When foreign genes are transformed into an organism, it is desirable to transform with a DNA sequence without introns, obtained for example from cDNA or by artificial synthesis.

Any method known in the art for introducing or transforming genes into the host is suitable for this invention and various types of vectors can be used, including autonomously replicating plasmid vectors or artificial chromosomes. Methods described in the art to integrate single or multiple copies of transforming genes into chromosomes in functional, expressible forms are also suitable for this invention. Examples of such methods for yeast, filamentous fungi and Corynebacteria, and other microorganisms have been described. An appropriate marker gene can be included in the transforming vector so that transformants can be easily selected. Co-transformation with a second vector containing a selectable marker gene can also be used. A wide range of marker genes is known. Transformants can also be selected by expression of a desired phenotype, such as enhanced ability to grow on xylose under anaerobic conditions (see Example 8).

It is envisaged in the invention that it can be advantageous in some cases to cause expression of the transformed genes only under specific culture conditions. For example, it can be useful first to grow the organism to a certain cell density, and then cause expression of the transforming gene. Promoters are known that can be induced by changes in temperature or pH, by particular carbon or nitrogen sources or by the presence or absence in the medium of certain organic or inorganic substances, such as phosphate or copper. Examples of yeast promoters that have been used for such inducible expression include GAL1, GAL10, CUP1 and PHO5.

The present invention is further illustrated by the following Examples which describe construction of the production strains of the invention, as well as their use in the above indicated specific aspects of the invention. If not otherwise indicated, all biotechnological procedures are carried out using methods conventional in the art.

EXAMPLE 1

Construction of the Integrant Strain with the XYL1 and XYL2 Genes of *Pichia Stipitis* Encoding Xylose Reductase and Xylitol Dehydrogenase The pMA91 (Mellor et al. [1983]) based yeast expression vector pAOS66 (FIG. 1) containing the XYL1 under the PGK1 promoter and the XYL2 under the modified ADH1 promoter (Ruohonen et al. [1995]) was digested with HindIII to isolate the 2.8 kb expression cassette carrying the XYL1 gene between the promoter and terminator of PGK1 and with BamHI to isolate the 2.2 kb expression cassette carrying the XYL2 gene between the modified ADH1 promoter and ADH1 terminator. Plasmid B955 (Toikkanen et al. [1998]) was used to construct the integration cassette. B955 is the Bluescript SK bacterial cloning vector (Stratagene) carrying two fragments of the URA3 gene (encoding orotidine-5'-P decarboxylase, Rose et al. [1984]); base pairs 71–450 and 781–1135 from the encoding region of the gene at SacI-XbaI sites and XhoI-Asp718 sites, respectively, of the polylinker region. The remaining polylinker sites HindIII and BamHI in the cloning vector were used for introducing the XYL1 and XYL2 expression cassettes between the two URA3 fragments by sticky-end ligations. The resulting construction (5' URA3 71–450 bp-XYL2 expression cassette 3'-5'-XYL1 expression cassette 5'-3'-URA3 781–1135 3') was released from Bluescript SK by SacI-NsiI digestion and isolated from an agarose gel. One μg of the fragment was used to transform the yeast strain CEN.PK2 (VW-1B) (MATα leu2-3,112 ura3-52 trpl-289 his3-Δ1 MAL2-8$^c$ SUC2) (Boles et al. [1996]) by the LiAc transformation procedure (Hill et al. [1991], Gietz et al. [1992]). The strain CEN.PK2 (VW-1B) is called "strain H1346" by us, and it has a VTT strain collection number VTT C-98304.

The integration strategy is based on the toxicity of 5-FOA (5-fluoro-orotic acid) to the yeast cells (Boeke et al. [1984]). Wild type cells convert 5-FOA to 5-FUMP (5-fluoro-uridine monophosphate), a potent inhibitor of thymidylate synthetase. Thus only ura3 (and ura5) mutants can grow in the presence of 5-FOA, as long as uracil is provided for the mutant strain. Integration of the above described fragment into the URA3 locus disrupts the wild type gene and the strain becomes uracil auxotrophic, allowing it to grow on 5-FOA plates.

The correct, functional integration was verified by Southern blotting, by measuring the XR and XDH activities in cell extracts and by showing that the integrant strain only grew on xylose in shake flask cultivations, in contrast to the non-transformed CEN.PK2 (VW-1B) strain. The integrant strain was named as H1469.

EXAMPLE 2

Cloning of *Saccharomyces Cerevisiae* Xylulokinase Gene (SGD no. YGR 194C)

The xylulokinase gene (XK) was amplified from total DNA of wild type yeast strain by X PCR, using forward primer 5' CCA GTG ATA TCG AGG ATG AGA TTA GTA C 3' (SEQ ID NO:6) and reverse primer 5' CCA GTG ATA TCT GTA CIT GTC AGG GCA T 3' (SEQ ID NO:7). Both primers contain an EcoRV restriction site at the 5' end. PCR reaction conditions were: 94° C. 3' hot start; 94° C. 1', 55° C. 1', 72° C. 2', 30 cycles, 72° C. 10' final extension. The PCR product was digested with EcoRV and purified from an agarose gel. The XK fragment was ligated into the vector B609 (Bluescribe M13; Stratagene, with the modified ADH1 promoter and ADH1 terminator) which had been treated with Klenow enzyme to make blunt ends. Orientation of the fragment was checked with BglII and EcoRI enzymes. A clone with the right orientation was digested with BamHI and the fragment was purified from an agarose gel. The BamHI fragment was cloned to BamHI site of YEplac195 yeast expression vector (Gietz and Sugino [1988]).

EXAMPLE 3

Cotransformation of the Integrant Strain H1469 with the Genes Encoding Xylulokinase (XK) and NAD-Dependent Glutamate Dehydrogenase (NAD-GDH) on Two Separate Multicopy Expression Vectors Two yeast expression vectors, the above described YEplac195 carrying the gene encoding the xylulokinase and YEplac181 carrying the gene GDH2 encoding the NAD-dependent glutamate dehydrogenase (Boles et al. [1993]) were cotransformed into H1469 integrant strain. YEplac195 vector was selected for by omitting uracil and YEplac181 by omitting leucine from the growth medium. Plasmid rescue from the yeast transformants verified the integrity of the two expression plasmids. The strain carrying both XK and NAD-GDH encoding genes was named as H1803 (VTT C-98302). A control strain carrying the gene encoding XK and YEplac181 control plasmid without GDH2 was named as H1805 (VTT C-98303).

EXAMPLE 4

Transformation of the Integrant Strain H1469 with the Gene Encoding NAD-Dependent Glutamate Dehydrogenase on a Multicopy Expression Vector The above described plasmid YEplac181 carrying the gene GDH2 encoding the NAD-dependent glutamate dehydrogenase was transformed into the integrant strain H1469. Selection of the transformants was as mentioned above. Plasmid rescue from the yeast transformants verified the integrity of the expression plasmid. The strain carrying the gene encoding NAD-GDH was named as H1795 (VTT C-98300). A control strain carrying the YEplac181 control plasmid was named as H1797 (VTT C-98301).

EXAMPLE 5

Transformation of the Yeast Strain H1346 (CEN.PK2 (VW-1B)) with the Gene Encoding NAD-Dependent Glutamate Dehydrogenase on a Multicopy Expression Vector The above described plasmid YEplac181 carrying the gene GDH2 encoding the NAD-dependent glutamate dehydrogenase was transformed into the CEN.PK2 (VW-1B) (=H1346) strain. Selection of the transformants was as mentioned above. Plasmid rescue from the yeast transformants verified the integrity of the expression plasmid. The strain carrying the gene encoding NAD-GDH was named as H1791 (VTT C-98298). A control strain carrying the YEplac181 control plasmid was named as H1793 (VTT C-98299).

EXAMPLE 6

Cloning of the Open Reading Frame YKL029C Encoding the Malic Enzyme Homologue from *Saccharomyces Cerevisiae*

The malic enzyme has been characterized from *S. cerevisiae* (Fuck et at. [1973]). Analysis of the yeast genome revealed one open reading frame (ORF YKL029C) with homology to the gene encoding malic enzyme from *Schizosaccharomyces pombe* (Viljoen et al. [1994]). The *S. cerevisiae* ORF YKL029C was amplified from the yeast chromosomal DNA by PCR using forward primer 5' CAT GCT AAG CIT CTA GAA TGC TrA GAA CCA GAC TA 3' (SEQ ID NO: 8) and reverse primer 5' GAT GCT AAG CIT CTA GAT GGT TAT GCT TCG TCT AC 3' (SEQ ID NO:9). Both primers contain HindIII and BglII restriction sites at the 5' end. PCR reaction conditions were: 94° C. 3' hot start; 94° C. 1', 40° C. 1', 72° C. 2', 30 cycles, 72° C. 10' final extension. The DNA fragment obtained was of expected size. The PCR fragment was digested with the appropriate restriction enzyme (BglII) to allow its cloning between the promoter and the terminator of PGK1 in the yeast expression vector pMA91.

EXAMPLE 7

Cloning of the Gene Encoding the Malic Enzyme from the Filamentous Fungus *Aspergillus Nidulans*

So far all the genes encoding the malic enzymes cloned from different organisms contain a DNA sequence coding for the "malic enzyme signature". It is a highly conserved, unique amino acid sequence (FNDDIQGTGAVNAS) (SEQ ID NO: 10) is particular protein (Prosite: PDOC00294). The signature allows specific degenerated primers to be planned for cloning of any particular gene encoding a malic enzyme.

Figure 2:
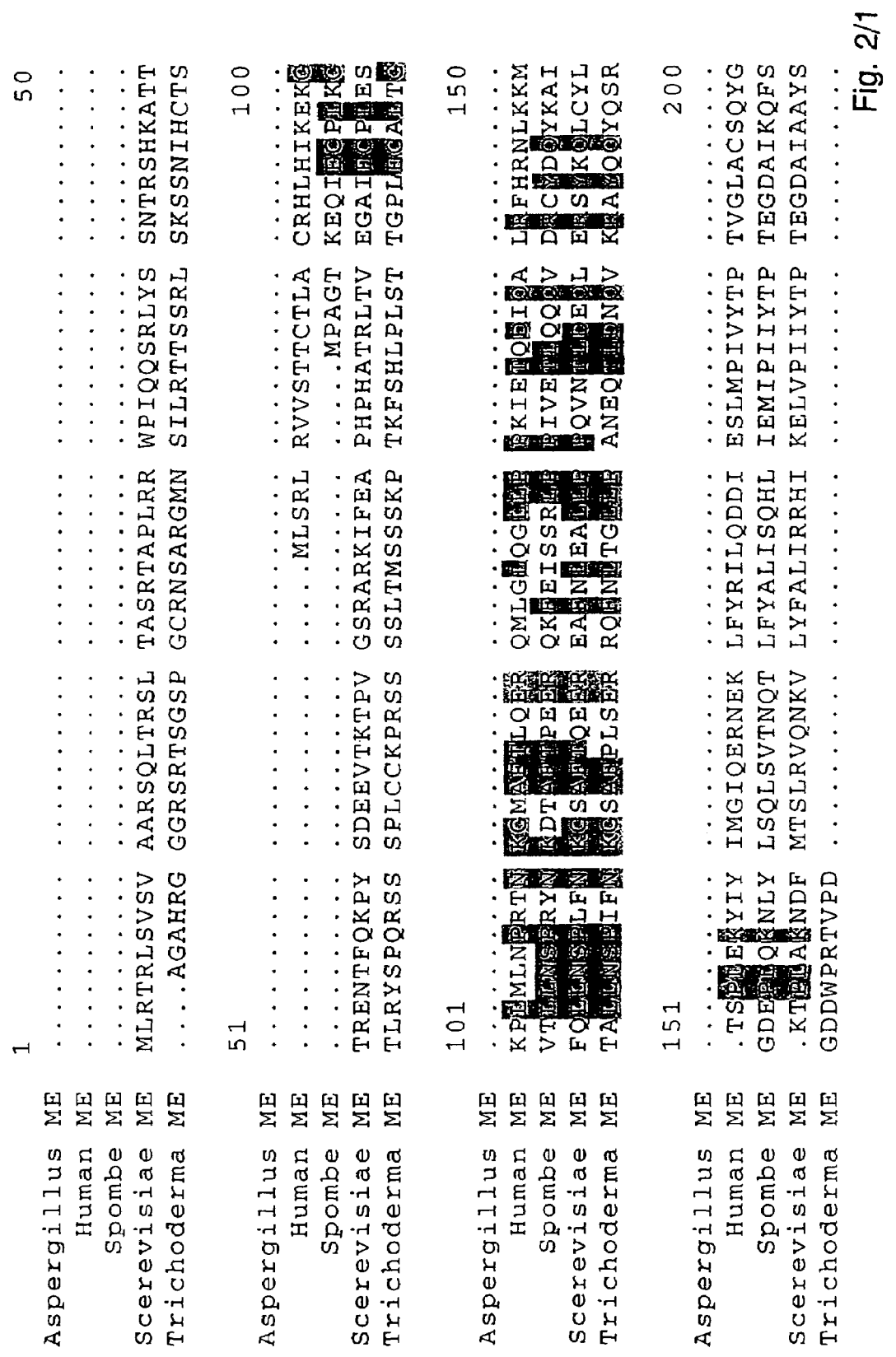

Degenerate primers were designed using the malic enzyme signature (region D) for the 3' end primer and a second homologous region of the protein, the region C for the 5' end primer (Viljoen et al. [1994]. The forward primer was 5' GA(T/C) GTI GGI ACI AA(T/C) AA 3' (SEQ ID NO:11), and the reverse primer was 5' GTI CC(T/C) TG(A/G/T) AT(A/G) TC(A/G) TC(A/G) TT(A/G) AA 3' (SEQ ID NO: 12). PCR reaction conditions were 94° C. 3' hot start; 94° C. 1', 37° C. 1', 72° C. 2', 7 cycles, 94° C. 1', 40° C. 1', 72° C. 2', 25 cycles, 72° C. 10' final extension Chromosomal DNA of Aspergillus nidulans was used as the template in the PCR reaction. A fragment of expected size was obtained (0.24 kb) and FIG. 2 shows the alignment of the PCR product with some known malic enzymes. A partial amino acid sequence of A. nidulans malic enzyme is given in SEQ ID NO: 1 partial sequence obtained allows the design of further primers, and can itself be used for probing by Southern hybridisation to clone the whole malic enzyme from any DNA bank (e.g. cDNA, chromosomal, lambda). The gene encoding the malic enzyme from Trichoderma reesei, another filamentous fungus can also be cloned. A partial amino acid sequence thereof is included in FIG. 2, and given also in SEQ ID NO: 2

EXAMPLE 8

Ethanol Production from Xylose

Part 1. Shake Flask Cultivations

The strains H1803 and H1805 (see Example 3) were cultivated in the growth medium which was modified SC-URA-LEU (synthetic complete media, uracil and leucine omitted, Sherman et al. [1983]) and Yeast Nitrogen Base without Amino Acids (Difco) and the carbon sources D-glucose (20 g/l) or D-xylose (20 g/l). Cells were pre-grown in shake flasks in a medium containing glucose as a carbon source. Cells were collected by centrifugation and resuspended in a volume of 100 ml media containing xylose as a carbon source. Cells were kept at 30° C. in 100 ml Erlenmeyer flasks gently stirred with a magnetic rod. Anaerobiosis was achieved by using an airlock.

After two days' incubation with xylose the strain with elevated levels of NAD-GDH had produced 2.35 g ethanol/g dry weight, and the control strain produced 1.47 g ethanol/g dry weight. The amount of ethanol was measured enzymatically with the aid of an automated analyser (Cobas-Mira).

Glutamate dehydrogenase activity was measured in a crude yeast cell extract, which was obtained by vortexing 500 mg of fresh cells in 500 µl of 100 mM Na-phosphate, pH 7.0 and 1 g glass beads (diameter 0.4 mm) for 15 minutes. The mixture was then centrifuged in a table top centrifuge and the supernatant assayed. 200 µl of a buffer containing 200 µM NAD(P)H and 100 mM Na-phosphate, pH 7.4 were mixed with 10 µl of the 20 fold diluted crude yeast extract. To start the reaction α-ketoglutarate (final concentration 10 mM) and ammonium chloride (final concentration 20 mM) were added. The rate of decreasing absorbance at 340 nm was measured and the activity was calculated from this. It is related to the protein content of the yeast extract as measured by a BIORAD protein assay. The NADP-GDH activity was measured using NADPH as a substrate and the NAD-GDH activity was measured with NADH as a substrate. The NAD-GDH activity was estimated 4–5 nkat/mg in the overexpression strain, and 0.04 nkat/mg in the control without GDH2 overexpressed. The NADP-GDH activity was about 2 nkat/mg. All assays were performed in a Cobas-Mira automated analyser.

Part 2. Fermentor Cultivations

Anaerobic xylose fermentation to ethanol was conducted in 1.8 liter Chemap CMF Fermentor (Switzerland) by genetically engineered strains of Saccharomyces cerevisiae, designated as H1803 and H1805. Both strains are derived from S. cerevisiae CEN.PK2 (VW-1B) (Boles et al. [1996]), and express xylose reductase (XR) and xylitol dehydrogenase (XDH) by chromosomal integration of the corresponding genes from Pichia stipitis. In addition, both strains overexpress the native xylulokinase (XK) from a multicopy plasmid (YEplac195+XK. Strain H1803 contains an additional plasmid that expresses the NAD-glutamate dehydrogenase (NAD-GDH) from S. cerevisiae (YEplac181+GDH2), whereas strain H1805 contains only the cloning vector (YEplac181) and serves as a control strain. Omitting uracil (URA) from the growth media can minimize plasmid segregation for the YEplac195 vector, and leucine (LEU) for YEplac181.

The seed cultures of strains H1803 and H1805 were routinely maintained on plates that were renewed every 2–3 weeks. The pre-inoculum was prepared by transferring a single colony into a 250 ml Erlenmeyer flask that contained 50 ml of modified synthetic complete medium without uracil and leucine (SC-URA-LEU)+20 g/l of glucose (Sherman et al. [1983]). For each strain three identical flasks were prepared. The cells were grown overnight on a rotary shaker at 150 rpm and 30° C., and the content of each flask was then transferred completely into a 3 l baffled flask that contained 500 ml of SC-URA-LEU plus 50 g/l of glucose and grown aerobically at 150 rpm and 30° C. until glucose was exhausted ($OD_{600}$: 20–25).

Cells from the above cultivation (six flasks) were harvested by a 10 minute centrifugation at 4,500 rpm and 4° C., washed by a 0.1 M $PO_4^{2-}$ buffer (pH=5.5) and resuspended in the same buffer each to a final volume of 30 ml and subsequently transferred to the fermentor. The fermentation medium contained SC-URA-LEU+10% xylose. The fermentor temperature was maintained at 30° C., the pH was controlled at 5.5 by addition of 2 M NaOH, and the agitation was constant at 300 rpm.

The cultivation was carried out under anaerobic conditions by flashing the headspace of the fermentor with nitrogen at a constant flow rate of 0.2 vvm. The offgas was connected via a multi-port valve to a Balzers quadrupole mass spectrometer (Sweden) for online analysis. Liquid samples were withdrawn from the fermentor at time intervals to measure growth, substrate consumption, and the formation of extracellular products. For selected samples the activities of the NADP- and NAD-glutamate dehydrogenases were also measured by standard enzymatic techniques. Growth was monitored by measuring both the absorbance at 600 nm, as well as the dry cell weight (DCW) by filtration and subsequent drying to constant weight. Xylose, ethanol, xylitol, glycerol and acetate present in the fermentor broth were separated on an HPX-87H column (55° C.), with 5 mM $H_2SO_4$ as eluent (0.6 ml/min), and quantified by refractive index (RI) detection. The amounts of ethanol, glycerol, xylitol and acetate were independently verified by appropriate enzymatic assays with the aid of an automated analyser (Cobas-Mira).

Figure 3:
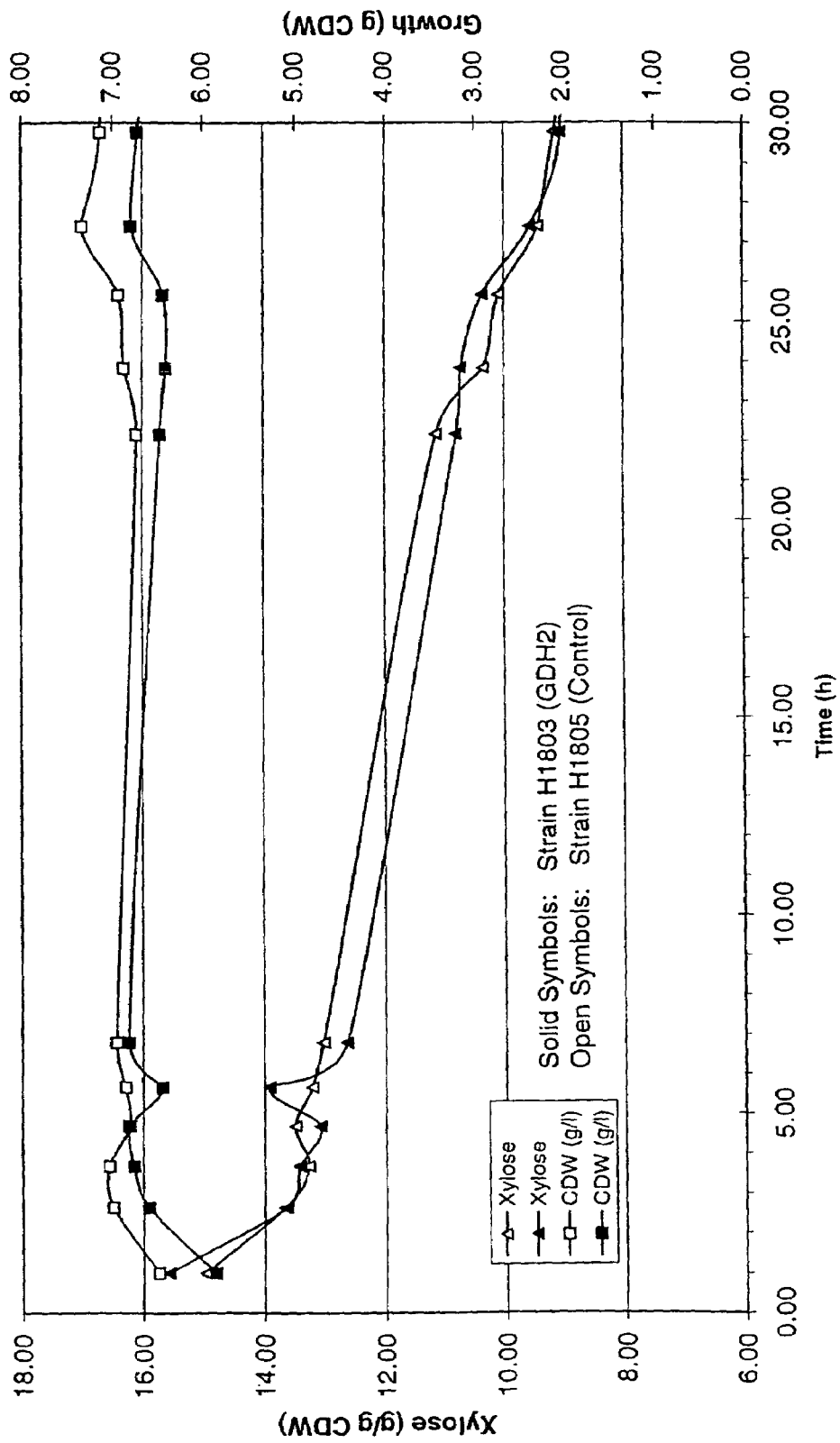
FIG. 3. Xylose fermentations with *Saccharomyces cerevisiae* recombinant strain expressing GDH2 (H1803, solid symbols) and control strain (H1805, open symbols): comparison of growth and xylose utilization rates.
Figure 4:
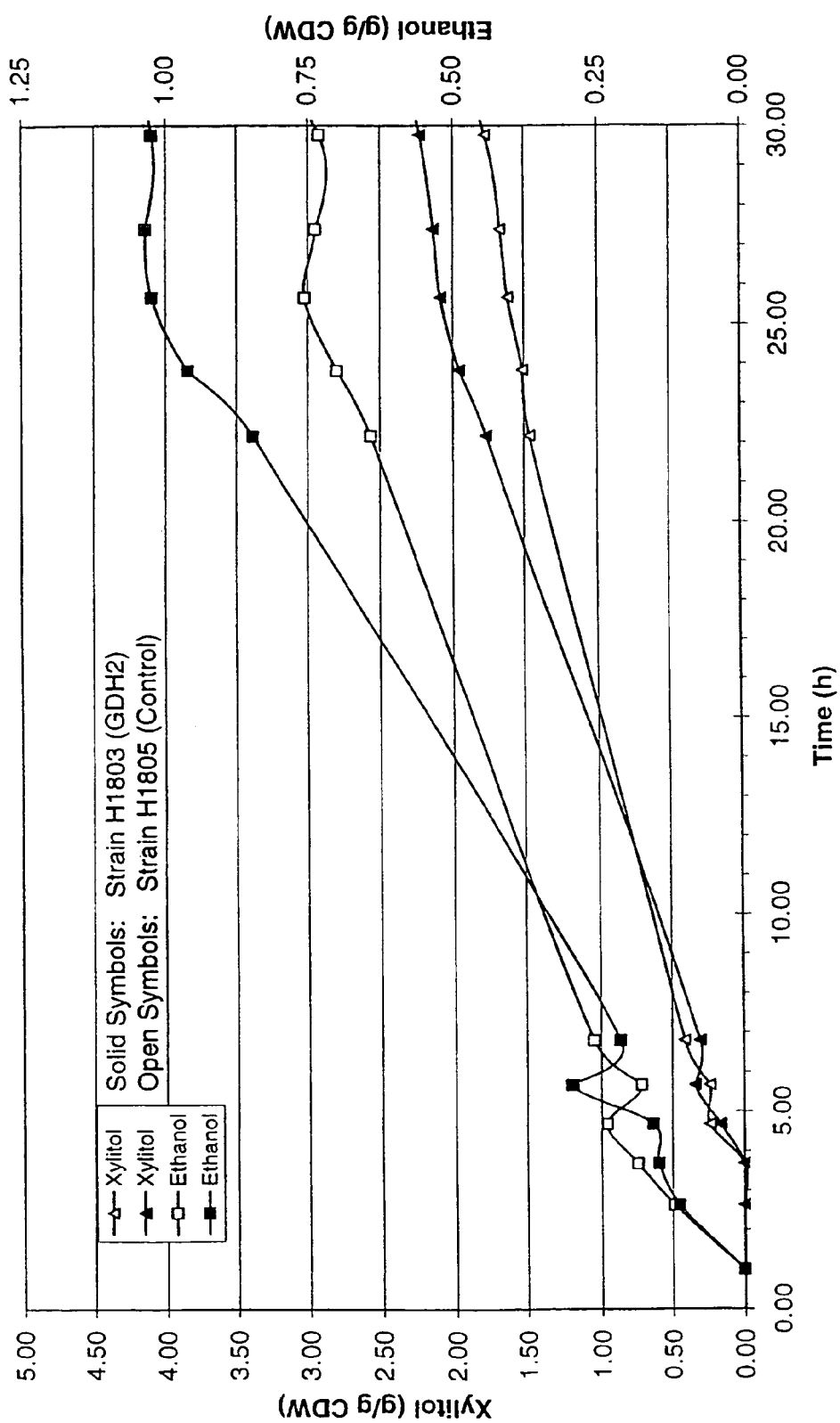
FIG. 4. Xylose fermentations with *Saccharomyces cerevisiae* recombinant strain expressing GDH2 (H1803, solid symbols) and control strain (H1805, open symbols): comparison of ethanol and xylitol production rates.

The growth and xylose consumption of strains H1803 and H1805 for the first 30 hours of cultivation are summarized in FIG. 3. Both strains can consume xylose effectively at comparable rates, however, the NAD-GDH overexpressing strain (H1803) accumulates about 6% less biomass (7.13 vs. 6.72 g/l). The most remarkable difference between the two strains is ethanol production. As illustrated in FIG. 4, by the end of the 30-hour time period the GDH2 strain accumulates about 1.02 g ethanol per g DCW compared with 0.73 for the control strain. This represents an enhancement of specific ethanol production of approximately 40% for the GDH2 strain (0.58 vs. 0.83 mmol/g-cell h). The volumetric productivity is also higher for the GDH2 strain by about 30% (3.94 vs. 5.20 mmol/l h). The corresponding yields of ethanol on xylose are 0.21 and 0.29 (mol/mol) for the control and GDH2 strains, respectively. Unexpectedly, xylitol production was also elevated for the GDH2 strain by about 25% as shown again in FIG. 4.

Figure 5:
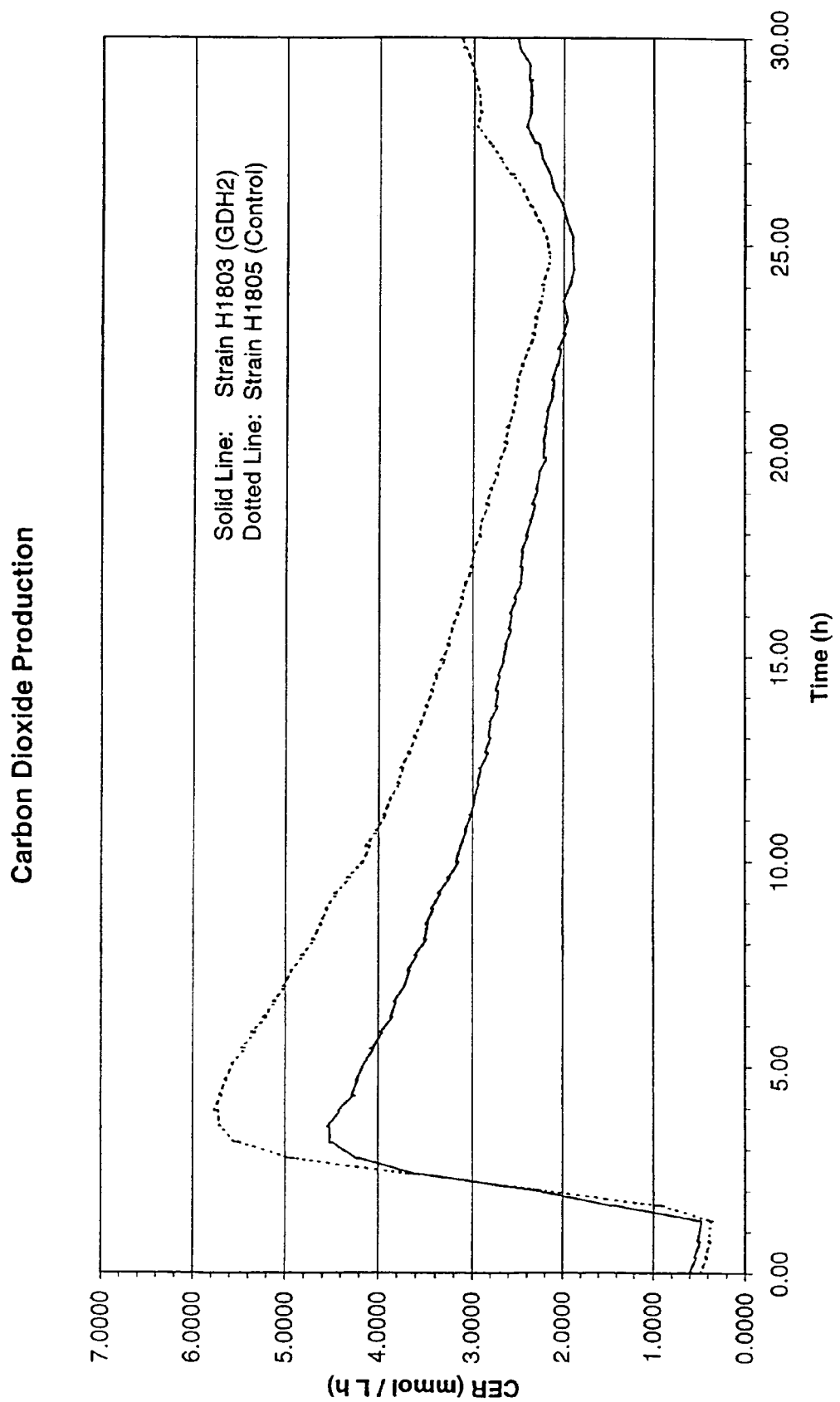
FIG. 5. Xylose fermentations with *Saccharomyces cerevisiae* recombinant strain expressing GDH2 (H1803, solid line) and control strain (H1805, dotted line): comparison of carbon dioxide evolution rates.

Yet another extraordinary divergence between the two recombinant strains is depicted in FIG. 5. This carbon dioxide data comes from the mass spectrometer measurements of the effluent gas. As shown in FIG. 5, overexpression of GDH2 significantly attenuates carbon dioxide evolution. Integrated values for $CO_2$ production from 0 to 30 hours are 100.4 and 80.7 mmol/l for the control and GDH2 strains, respectively, i.e. the GDH2 strain wastes about 20% less of the carbon source to carbon dioxide production.

Figure 6:
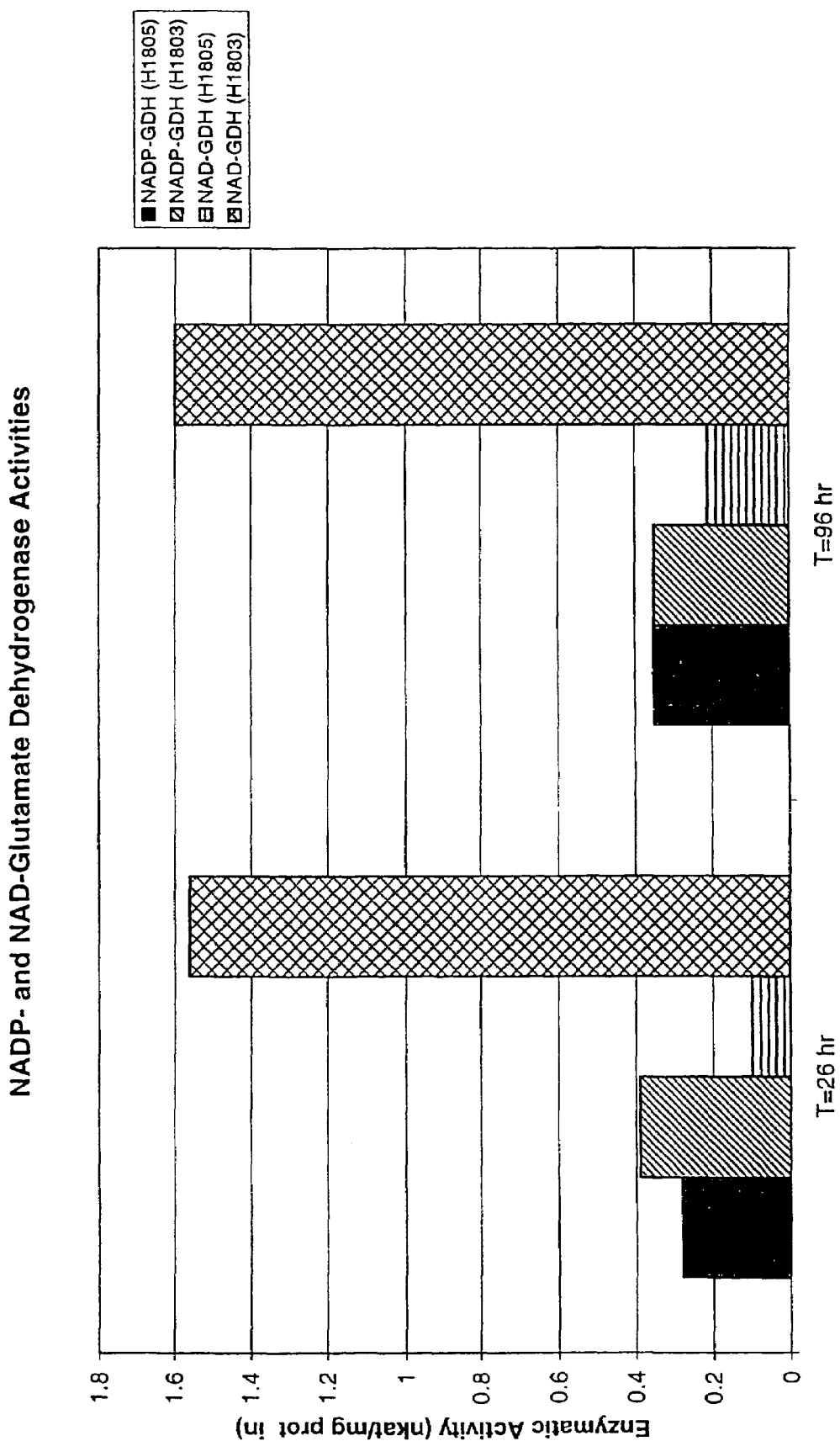
FIG. 6. Specific enzymatic activities of NADP-glutamate dehydrogenase (NADP-GDH) and NAD-glutamate dehydrogenase (NAD-GDH) for strains H1805 (control) and H1803 at time points of 26 and 96 hours.

Enzymatic assays for NADP-GDH and NAD-GDH were performed on chosen samples and results from two such sets are shown in FIG. 6. The assay mixture contained 100 mM sodium phosphate buffer at pH=7.0, 200 µM of either NADPH (NADP-GDH assay) or NADH NAD-GDH assay), and cell lysate at a final concentration of about 0.5 mg/ml. The reaction was started by addition of 20 mM α-ketoglutarate plus 40 mM $NH_4Cl$, and the NAD(P)H consumption was monitored spectrophotometrically at 340 nm. Both strains have notable NADP-GDH activities as expected, although H1803 appears to have a surprisingly higher specific activity for this enzyme (about 40% or so). On the other hand, NAD-GDH activity is essentially close to the assay detection limit for the control strain, whereas, H1803 has a fairly high specific activity for this NAD-enzyme.

These results show that the recombinant strain H1803 overexpressing the NAD-glutamate dehydrogenase has significantly enhanced capabilities for ethanol (and xylitol) production, both in terms of higher specific productivities as well as higher product yields on the carbon substrate. The recombinant strain also produces significantly less (undesired) cell mass and very substantially less (undesired) carbon dioxide, thereby not only increasing yields of desired products but also decreasing disposal and pollution loads.

EXAMPLE 9

Ethanol Production from Glucose

Glucose fermentation to ethanol was conducted in 1.8 liter Chemap CMF Fermentor (Switzerland) by genetically engineered strains of *Saccharomyces cerevisiae*, designated as H1793 and H1791, both of which are derived from *S. cerevisiae* CEN.PK2 (VW-1B) (Boles et al. [1996]). Strain H1791 is transformed with a plasmid that expresses the NAD-glutamate dehydrogenase (NAD-GDH) from *S. cerevisiae* (YEplac181+GDH2), whereas strain H1793 contains only the cloning vector (YEplac181) and serves as a control strain. Plasmid segregation can be minimized by omitting leucine (LEU) from the growth media.

The inoculum was prepared by transferring a single colony into a 250 ml Erlenmeyer flask that contained 50 ml of modified synthetic complete medium without leucine (SC-LEU)+20 g/l of glucose. The cells were grown overnight on a rotary shaker at 150 rpm and 30° C. ($OD_{600}$: 10–15). Cells from the above cultivation were harvested by a 10 minute centrifugation at 4,500 rpm and 4° C., washed with 0.1 M $PO_4^{2-}$ buffer (pH=5.5) and resuspened in the same buffer each to a final volume of 25 ml and subsequently transferred to the fermentor. The fermentation medium contained (per liter): yeast-nitrogen-base (without amino acids and without ammonia) 3.4 g, uracil 0.044 g; tryptophan 0.164 g, histidine 0.116 g, $KNO_3$ 5.055 g, glucose 40 g. The fermentor temperature was maintained at 30° C., the pH was controlled at 5.5 by addition of 2 M NaOH, and the agitation was constant at 300 rpm. The cultivation was carried out under anaerobic conditions by flashing the headspace of the fermentor with nitrogen at a constant flowrate of 0.2 vvm. The offgas was connected via a multi-port valve to a Balzers quadrupole mass spectrometer (Sweden) for online analysis. Liquid samples were withdrawn from the fermentor at time intervals to measure growth, substrate consumption, and the formation of extracellular products. Biomass, glucose, ethanol, glycerol and acetate were measured as in the previous example.

Figure 7:
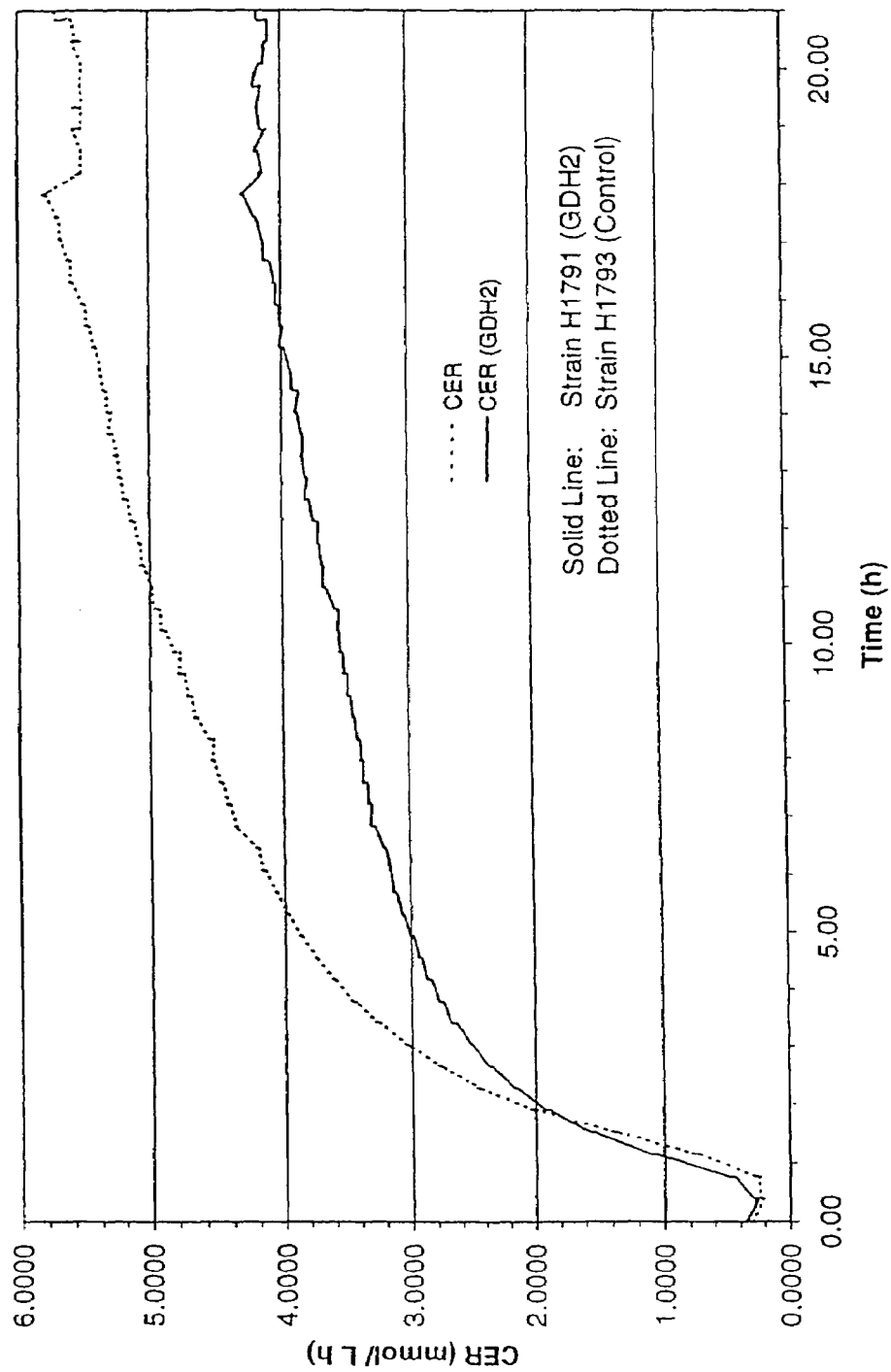
FIG. 7. Glucose fermentations with *Saccharomyces cerevisiae* recombinant strain expressing GDH2 (H1791, solid line) and control strain (H1793, dotted line): comparison of carbon dioxide evolution rates.

Table 1 summarizes the primary fermentation data for these two fermentations. The NAD-GDH overexpressing strain (H1791) accumulates on the average about 12% less biomass (0.52 vs. 0.46 g/l). during the 21 hour time period. Specific glucose consumption rates are comparable for the two strains (within 5%). However, the GDH2 strain has both a higher volumetric (11%) and a higher specific (25%) ethanol production rate. Yet another extraordinary divergence between the two recombinant strains is depicted in FIG. 7. This carbon dioxide data comes from the mass spectrometer measurements of the effluent gas. As shown in FIG. 7, overexpression of NAD-GDH significantly attenuates carbon dioxide evolution. Integrated values for $CO_2$ production from 0 to 21 hours are 93.7 and 70.6 mmol/l for the control and GDH2 strains respectively, i.e. the GDH2 strain wastes about 25% less of the carbon source to carbon dioxide. The specific $CO_2$ production rate for the GDH2 strain is also attenuated by about 15%. In addition, the yield of ethanol on glucose (mol/mol) is estimated to be approximately 19% higher for the GDH2 strain vs. the control strain.

These results show that the recombinant strain H1791 overexpressing the NAD-glutamate dehydrogenase (NAD-GDH) has significantly enhanced capabilities for ethanol production from glucose, both in terms of higher specific productivities as well as higher product yields on the carbon substrate. The recombinant strain also produces significantly less (undesired) cell mass and less (undesired) carbon dioxide, thereby not only increasing yields of desired products but also decreasing disposal and pollution loads.

TABLE 1

Glucose fermentations with *Saccharomyces cerevisiae* recombinant strain overexpressing NAD-GDH (H1791) and control strain (H1793): comparison of growth, glucose consumption, ethanol production and carbon dioxide evolution rates. The last two rows show calculated average fluxes expressed in either volumetric ($J_V$, mmol/l h) or specific ($J_S$, mmol/g-cell h) terms. Glucose and ethanol concentrations represent average values from four measurements: two with HPLC and two with enzymatic assays.

| | Biomass (g/l) | | Glucose (g/l) | | Ethanol (g/l) | | $CO_2$ (mole %) | |
|---|---|---|---|---|---|---|---|---|
| Time (h) | 1793 | 1791 | 1793 | 1791 | 1793 | 1791 | 1793 | 1791 |
| 0 | 0.315 | 0.300 | 39.27 | 37.57 | 0.01 | 0.01 | 0.000 | 0.000 |
| 6 | 0.740 | 0.670 | 37.68 | 36.48 | 0.63 | 0.72 | 1.333 | 0.619 |
| 17 | 0.790 | 0.760 | 33.00 | 32.49 | 2.39 | 2.37 | 1.552 | 0.823 |
| 19 | 0.820 | 0.690 | 32.22 | 31.04 | 2.65 | 2.78 | 1.735 | 0.701 |
| 21 | 0.800 | 0.670 | 30.98 | 29.85 | 2.98 | 3.30 | 1.818 | 0.711 |
| $J_V$ | — | — | −2.19 | −2.04 | 3.08 | 3.41 | 4.46 | 3.36 |
| $J_S$ | — | — | −4.21 | −4.43 | 5.92 | 7.40 | 8.58 | 7.31 |

EXAMPLE 10

An Alternative Cloning Strategy of the Open Reading Frame YKL029C Encoding the Malic Enzyme Homologue from *Saccharomyces Cerevisiae*

If the restriction enzyme BglII is used for the cloning of the malic enzyme homologue between the promoter and terminator of PGK1 in the yeast expression vector pMA91, a partial enzyme digestion has to be done, as there is an internal BglII site at +227 bp of the malic enzyme coding region. An alternative cloning strategy was as follows: The PCR fragment was digested with HindIII restriction enzyme and treated with Klenow enzyme to make blunt ends. The expression vector pMA91 (Mellor et al. [1983]) was digested with HindIII restriction enzyme and the 1.8 kb fragment containing the PGK1 promoter and terminator was isolated from an agarose gel. The promoter-terminator cassette was ligated into the YEplac195 vector (Gietz and Sugino [1988]) which had been linearised at its multicloning site with HindIII. The orientation of the promoter-terminator fragment in the expression vector is HindIII-PGK1 promoter-PGK1 terminator-EcoRI This expression vector was digested with BglII and treated with Klenow enzyme to obtain blunt ends for the cloning of the malic enzyme homologue between the promoter and terminator of PGK1.

The ORF YKL029C cloned by PCR was completely sequenced. Two point mutations, created during PCR amplification altering two amino acids in the enzyme were observed; leucine 341 to valine and glutamine 620 to leucine. These point mutations were neither in regions of conserved amino acids of malic enzymes (Viljoen et al. [1994]) nor did they significantly alter the apparent $K_m$ values of the PCR-amplified enzyme as compared to the native enzyme (native enzyme activity measured from the strain H1346; see Table 2 and Fuck et al. [1973]) and were thus considered neutral. The invention can be practised with this gene variant, or with a native gene encoding malic enzyme or with any other neutral variant.

TABLE 2

The apparent $K_m$ values for malate, $NAD^+$ and $NADP^+$ of the native and the PCR-amplified malic enzyme from *S. cerevisiae*

| | L-malate $K_m$ (mM) | $NAD^+$ $K_m$ (mM) | $NADP^+$ $K_m$ (mM) |
|---|---|---|---|
| Native malic enzyme | 17.1 | 0.07 | 0.06 |
| PCR-amplified malic enzyme | 15.4 | 0.14 | 0.08 |

The YEplac195 control vector, and the same vector with the malic enzyme homologue of *S. cerevisiae* under PGK1 promoter and terminator were transformed into the yeast strain CEN.PK2 (VW-1B, H1346), to obtain strains H2189 (VTT C-99316) and H2193 (VTT C-99317), respectively.

EXAMPLE 11

Integration of the Xylulokinase Gene (YGR194C) into the Integrant Strain H1469

A cassette for the integration of the xylulokinase gene was constructed with HIS3 flanking regions and the kanamycin resistance gene KMX2 for selection.

The yeast shuttle vector pRS423 (Christianson et al. [1992]) was digested with DrdI to obtain a fragment of 1.5 kb containing the HIS3 gene encoding imidazoleglycerol-P hydratase (Fink [1964]). The fragment was isolated from an agarose gel, blunt ended with T4 polymerase and ligated to the EcoRV site of Bluescript SK bacterial cloning vector (Stratagene).

The pFA6-kanMX2 plasmid (Wach et al. [1994]) was digested with PvuII and SpeI to isolate the 1.4 kb kanamycin resistance module. The KMX2 fragment was isolated from an agarose gel and blunt ended with Klenow enzyme. The Bluescript SK carrying the HIS3 DrdI fragment was digested with NheI and BclI within the HIS3 gene (removing 50 bp from its coding region), blunt ended with Klenow enzyme and treated with shrimp alkaline phosphatase, prior to ligation with the isolated KMX2 fragment.

The xylulokinase gene under the modified ADH1 promoter and ADH1 terminator in YEplac195 (see Example 2.) was isolated after a BamHI digestion from an agarose gel. The Bluescript SK carrying the HIS3 DrdI fragment with the KMX2 module was digested with BglII within the HIS3 gene (two adjacent BglII sites removing 60 bp from its coding region) and was treated with shrimp alkaline phosphatase, prior to ligation with the isolated xylulokinase fragment with ADH1 promoter and terminator.

The final integration cassette thus constructed contained 900 bp of HIS3 sequence, the xylulokinase gene (ADH1 terminator, the XK gene, modified ADH1 promoter) 50 bp HIS3 coding region, the AXE cassette (promoter, the gene, terminator) and 550 bp of HIS3 sequence. This construction was separated from Bluescript SK by BstBI and BssHI digestion, leaving about 400 bp of HIS3 sequence at either side for targetted integration.

One μg of the integration cassette isolated from an agarose gel was used to transform the H1469 strain, to obtain the strain H2217 (VTT C-99318). The screening for integrant transformants was on YPD plates with 200 μg/ml of G418. The correct integration of the XK cassette to the HIS3 locus was verified by Southern hybridisation, by PCR, and by enhanced growth on xylulose as compared to the wild type.

EXAMPLE 12

Transformation of the Integrant Strains H1469 and H2217 with the Gene Encoding Malic Enzyme on a Multicopy Expression Vector The above described plasmid YEplac195 carrying the gene MAE1 encoding the malic enzyme under the promoter and terminator of PGK1 (see example 6 or 10), and the control plasmid YEplac195 were transformed into the integrant strains H1469 and H2217. The plasmids were selected for by omitting uracil from the growth medium. Plasmid rescue from the yeast transformants verified the integrity of the control and expression plasmids. The strains obtained were named as follows; H1469 with the control plasmid as H2191 (VTT C-99319), H1469 with the malic enzyme plasmid as H2195 (VTT C-99320), H2217 with the control plasmid as H2221 (VTT C-99321) and H2217 with the malic enzyme plasmid as H2222 (VTT C-99322).

EXAMPLE 13

Effect of Malic Enzyme: Ethanol Production from Glucose

Glucose fermentation to ethanol was conducted in 1.8 liter Chemap CMF Fermentor (Switzerland) by genetically engineered strains of *Saccharomyces cerevisiae* derived from *S. cerevisiae* CEN.PK2/VW-1b (Boles et al. [1996]) designated below as H1346. More specifically, the two strains used is this example are as follows: (i) H2193: H1346 transformed with a plasmid that expresses the *S. cerevisiae* malic enzyme (MAE1, ORF YKL029c), or, (ii) H2189: H1346 transformed with the cloning vector (YEplac195) and serves as a control strain. Omitting uracil (URA) from the growth media minimizes plasmid segregation.

The inoculum was prepared by transferring a single colony into a 250 ml Erlenmeyer flask that contained 50 ml of synthetic complete medium without uracil (SC-URA)+20 µl of glucose. The cells were grown overnight on a rotary shaker at 150 rpm and 30° C. ($OD_{600}$: 10–15). Cells from the above cultivation were harvested by a 10 minute centrifugation at 4,500 rpm and 4° C., washed with 0.1 M phosphate buffer (pH=5.5) and resuspended in the same buffer each to a final volume of 25 ml and subsequently Ills transferred to the fermentor. The fermentation medium contained (per liter): yeast-nitrogen-base (without amino acids), amino acid supplements, glucose 30 g. The fermentor temperature was maintained at 30° C., the pH was controlled at 5.5 by addition of 2 M NaOH, and the agitation was constant at 300 rpm. The cultivation was carried out under anaerobic conditions by sparging the broth with nitrogen at a constant flow rate of 0.1 vvm. Liquid samples were withdrawn from the fermentor at time intervals to measure growth, substrate consumption, and the formation of extracellular products. Biomass, glucose, ethanol, glycerol and acetate were measured as in the previous example.

Table 3 summarizes the fermentation results for these two fermentations. The MAE1 overexpressing strain (H2193) utilizes approximately 20% less carbon for biomass synthesis (3.27 vs. 2.60 C-mol/g-cell h), resulting in final biomass densities that are significantly lower compared with the control (1.33 vs. 2.20 g/l). The specific glucose consumption rate is ca. 20% higher for the MAE1 strain. More importantly, the MAE1 has higher specific ethanol production rate of about 25% (18.85 vs. 23.64 C-mmol/g-cell h). Higher specific ethanol production rates are advantageous in processes that are physically constrained by the amount of biocatalyst that can be utilized, e.g. cell-immobilized fermentation systems. Furthermore, the ethanol yield on glucose for the MAE1 overexpressing strain is about 4% higher compared with the control (0.478 vs. 0.499 C-mol/C-mol).

These results disclose that the recombinant *S. cerevisiae* strain H2193 overexpressing the endogenous malic enzyme (MAE1) has significantly enhanced capabilities for ethanol production from glucose as the carbon substrate. The recombinant strain also produces significantly less (undesired) cell mass, thereby not only increasing yields of desired products but also decreasing disposal loads.

TABLE 3

Glucose fermentations with *Saccharomyces cerevisiae* recombinant strain expressing MAE1 (H2193) and control strain (H2189): average fluxes expressed in either volumetric ($J_V$, C-mmol/l h) or specific ($J_S$, C-mmol/g-cell h) terms (time interval: 3.3 to 29 hours). Glucose and ethanol concentrations represent average values from four measurements: two with HPLC and two with enzymatic assays.

|  | Biomass (g/l) | | Glucose (g/l) | | Ethanol (g/l) | |
| --- | --- | --- | --- | --- | --- | --- |
|  | H2193 | H2189 | H2193 | H2189 | H2193 | H2189 |
| $J_V$ (C-mmol/l h) | 1.68 | 3.01 | 30.61 | 36.32 | 15.27 | 17.35 |
| $J_S$ (C-mmol/g-cell h) | 2.60 | 3.27 | 47.37 | 39.47 | 23.64 | 18.85 |

The previously described experiment was repeated with the following modifications: (1) The bioreactor inoculum size was increased from ca. 0.1 g/l to ca. 2 g/l, and, (2) In addition to using a large inoculum (ca. 2 g/l), subsequent to glucose exhaustion (24 hours) a concentrated solution of glucose was added to the fermentor to give a final glucose concentration of about 45 g/l and the fermentation was allowed to proceed for an additional 24 hours (repeated batch). The primary results were as follows for the two cases: (1) Overexpression of the malic enzyme results in higher specific rates of ethanol production (+9%) and glucose consumption (+20%) with less glucose being diverted to biomass for (−16%); (2) Overexpression of the malic enzyme enhanced the specific ethanol production rates by 6 and 8% for the first and second phases respectively, while corresponding glucose uptake rates are also higher by 16 and 17% in the two phases. The initial biomass concentration of 2 g/l for both strains increased to 5.73 and 6.36 g/l for the strain overproducing malic enzyme and the control respectively during the first phase (i.e. 10% less for MAE1). Corresponding values for the second phase were 7.66 vs. 8.15 g/l (i.e. 6% less for MAE1).

To summarize, these three experiments disclose that the recombinant *S. cerevisiae* strain H2193 overexpressing the native malic enzyme (MAE1) has significantly enhanced capabilities for ethanol production from glucose as the carbon substrate (specific rates increased by up to 25%, yields increased by 4% o). The recombinant strain also produces significantly less (undesired) cell mass, thereby not only increasing yields of desired products but also decreasing disposal loads.

EXAMPLE 14

Effect of Malic Enzyme: Ethanol Production from Xylose

Xylose fermentation to ethanol was conducted in a 1.8 liter Chemap CMF Fermentor (Switzerland) by genetically engineered strains of *Saccharomyces cerevisiae* derived from *S. cerevisiae* CEN.PK2/VW-1b (Boles et al. [1996]) designated below as H1346. More specifically, the four strains used is this example are as follows: (i) H2195: H1346 carrying chromosomal integrations of genes encoding xylose reductase (XR) and xylitol dehydrogenase (XDH) (strain H1469) transformed with a plasmid that expresses the *S. cerevisiae* malic enzyme (MAE1, ORF YKL029c) (ii) H2191: H1469 transformed with the cloning vector (YEplac195) and serving as a control for strain H2195. (iii) H2222: H1346 carrying chromosomal integrations of genes encoding xylose reductase (XR), xylitol dehydrogenase (XDH), and xylulokinase (XK) (strain 2217) transformed with a plasmid that expresses the *S. cerevisiae* malic enzyme (MAE1, ORF YKL029c) (iv) H2221: H2217 transformed with the cloning vector (YEplac195) and serving as a control for strain H2222. Omitting uracil (URA) from the growth media minimizes plasmid segregation.

The inoculum was prepared by transferring a single colony into a 250 ml Erlenmeyer flask that contained 50 ml of synthetic complete medium without uracil (SC-URA)+ 0.1 M phosphate +20 g/l of glucose. Cells were grown overnight on a rotary shaker at 150 rpm, 30° C. and then the whole broth was transferred to a 2 L flask that contained 500 ml SC-URA+0.1 M phosphate +50 g/l glucose. The culture was again grown overnight as above and the cells were then harvested by a 10 minute centrifugation at 4,500 rpm and 4° C. The cells were then washed with 0.1 M phosphate buffer (pH=5.5) and resuspended in the same buffer each to a final volume of 100 ml and subsequently transferred to the fermentor.

The fermentation medium contained (per liter): yeast-nitrogen-base (without amino acids), amino acid supplements, xylose 50 g. The fermentor temperature was maintained at 30° C., the pH was controlled at 5.5 by addition of 2 M NaOH, and the agitation was constant at 300 rpm. The cultivation was carried out under anaerobic conditions by sparging the broth with nitrogen at a constant flowrate of 0.1 vvm. Liquid samples were withdrawn from the fermentor at time intervals to measure growth, substrate consumption, and the formation of extracellular products. Biomass, glucose, ethanol, glycerol and acetate were measured as in the previous example.

a) Anaerobic Xylose Fermentations with Strains H2195 and H2191

FIG. 8 shows time profiles for the biomass and turbidity for the MAE1 overexpressing strain (H2195) and the control strain (H2191). Note that *Saccharomyces cerevisiae* expressing genes encoding XR and XDH in general can utilize xylose, however, they are unable to grow on xylose anaerobically. As illustrated by FIG. 8, overexpression of the native malic enzyme has indeed a positive effect on cell viability under these conditions. Strain H2195 portrays an initial growth on xylose even under anaerobic conditions which is followed by a decline in biomass to a level after 32 hours that corresponds to that of the inoculum. On the contrary, the biomass of the control declines monotonically during this same time period from an initial value of 2.11 down to 1.47 g/l, i.e. a drop of biomass of ca. 30%.

Figure 9:
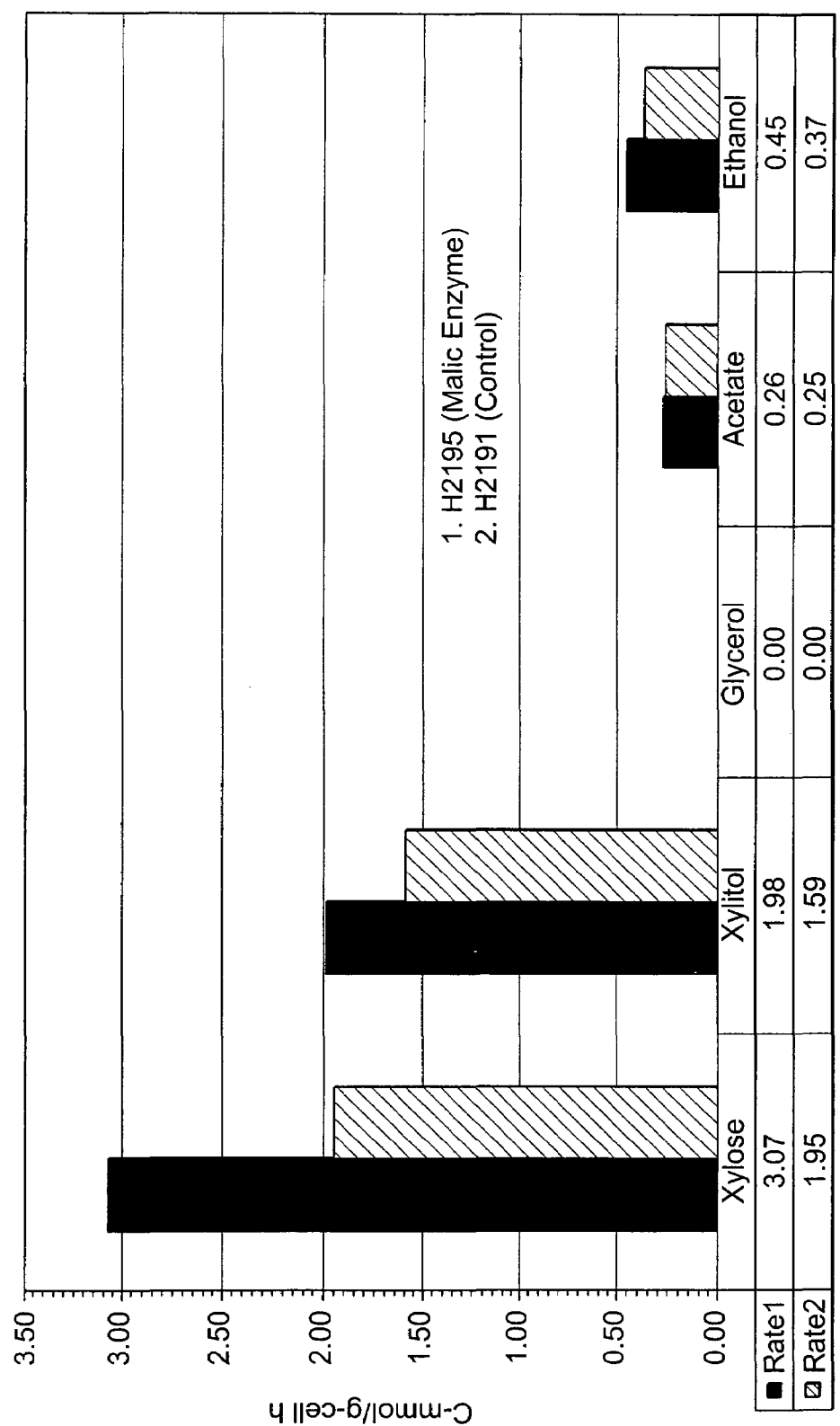
FIG. 9. Overall specific metabolic rates (C-mmol/g-cell h) from batch fermentations of *Saccharomyces cerevisiae* recombinant strain expressing MAE1 (H2195) and control strain (H2191).

FIG. 9 summarizes the overall specific metabolic rates (C-mmol/g-cell h) for these two batch fermentations. Evidently, in addition to preventing cell degradation, overexpression of the malic enzyme has also a positive effect on xylose utilization and on the production of both ethanol and xylitol. Xylose utilization is enhanced by more than 55%, and the productivities of ethanol and xylitol are increased by about 20% and 25%, respectively.

These results disclose that the recombinant *S. cerevisiae* strain H2195 overexpressing the native malic enzyme (MAE1) has significantly enhanced capabilities for xylose utilization as well as for ethanol and xylitol production from xylose. The recombinant strain can also sustain its viability for prolonged time periods.

b) Anaerobic Xylose Fermentations with Strains H2222 and H2221

This experiment was carried out as described in part (a) except that strains H2195 and H2191 were substituted with strains H2222 and H2221 that in addition to the genes encoding XR and XDH also carry a chromosomal integration of a gene encoding the native XK. Strain H2222 overexpresses the native malic enzyme.

Figure 10:
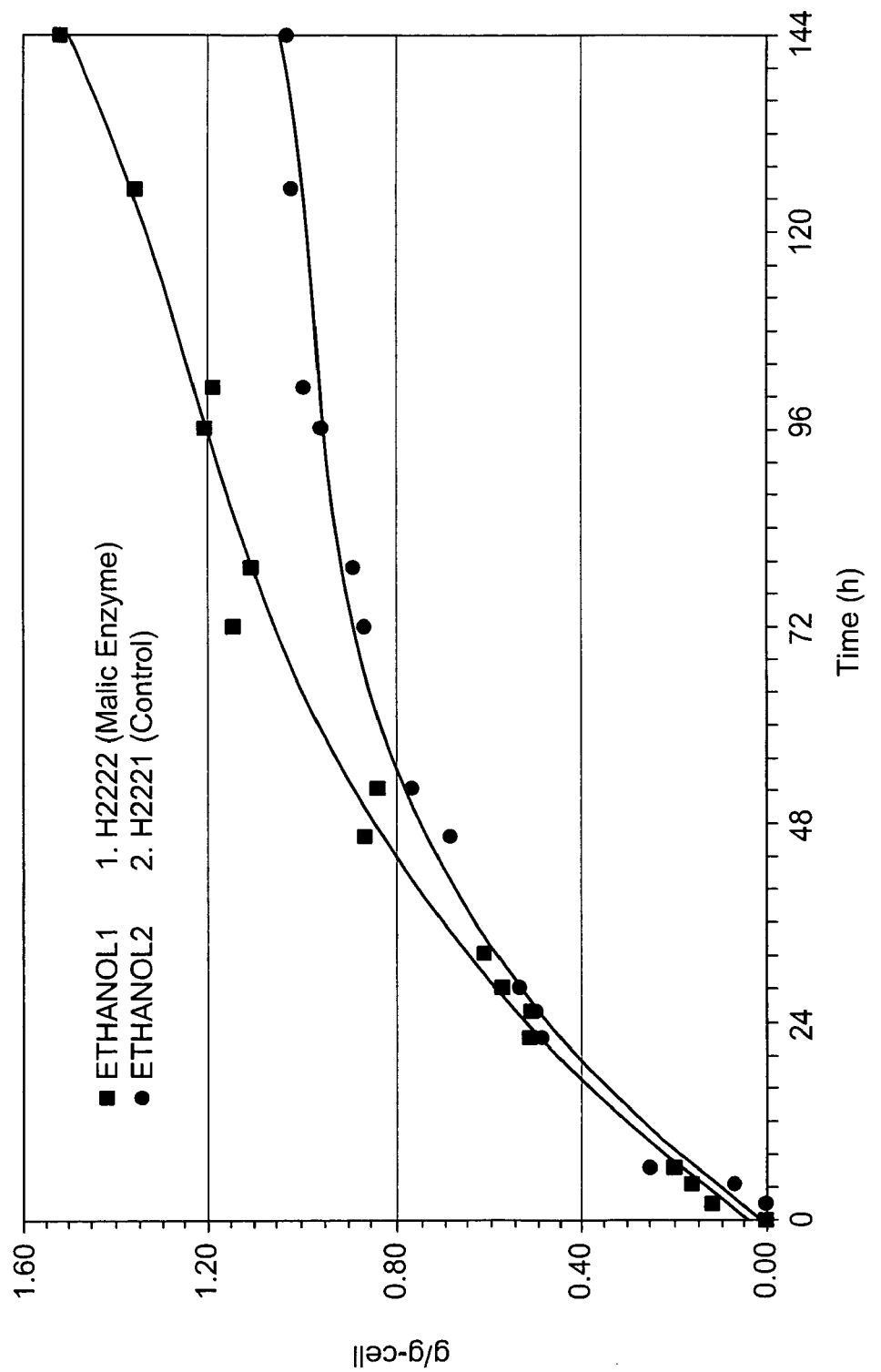
FIG. 10. Time profiles for ethanol production from xylose in batch fermentations of *Saccharomyces cerevisiae* recombinant strain expressing MAE1 (H2222) and control strain (H2221). Ethanol concentrations are normalized with corresponding biomass levels.

It is evident from FIG. 10 that overexpression of the malic enzyme has a significant enhancing effect on ethanol production from xylose, and also that this can be sustained for several days in a row.

Figure 11:
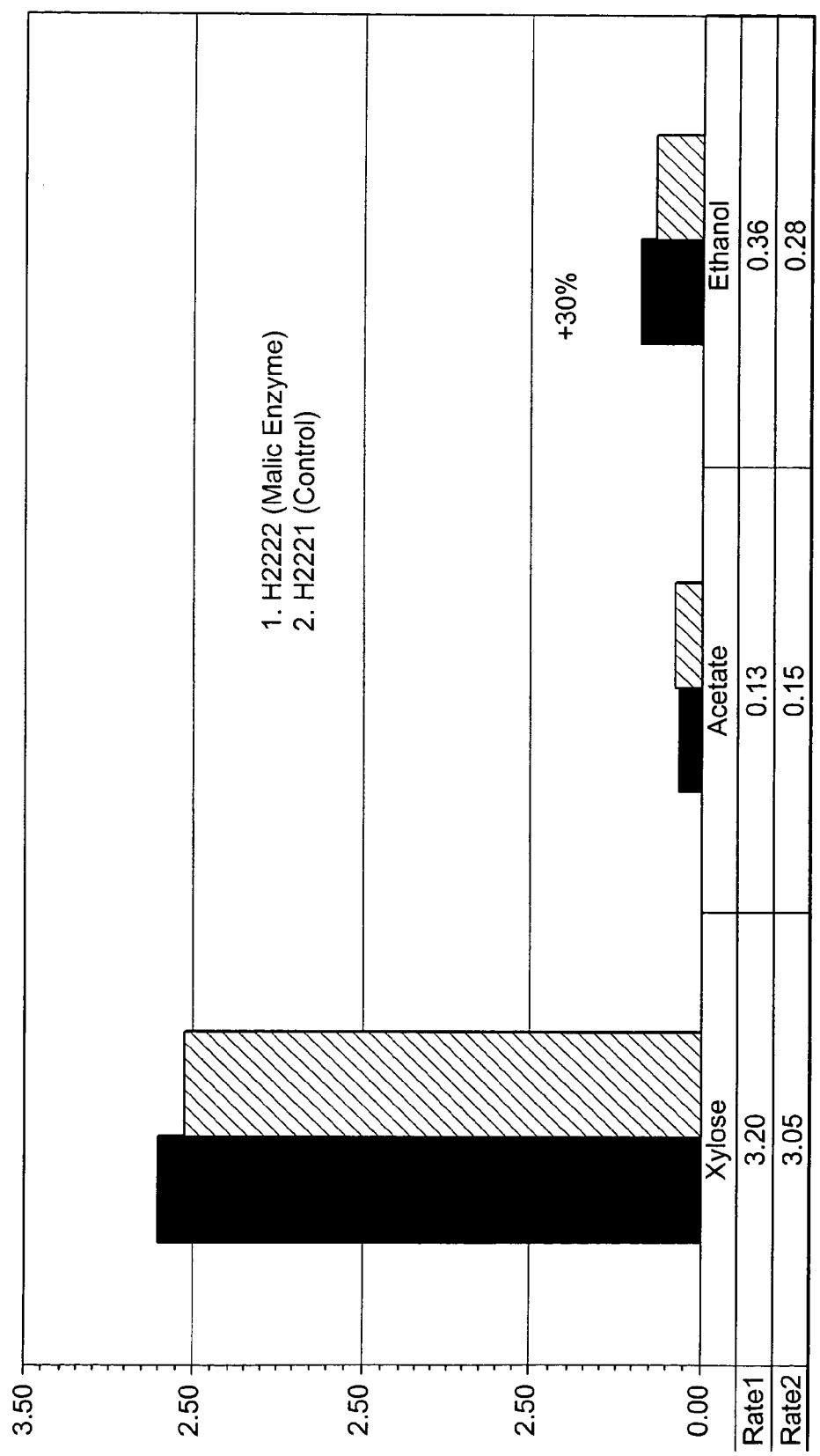
FIG. 11. Overall specific metabolic rates (C-mmol/g-cell h) from batch fermentations of *Saccharomyces cerevisiae* recombinant strain expressing MAE1 (H2222) and control train (H2221).
Figure 12:
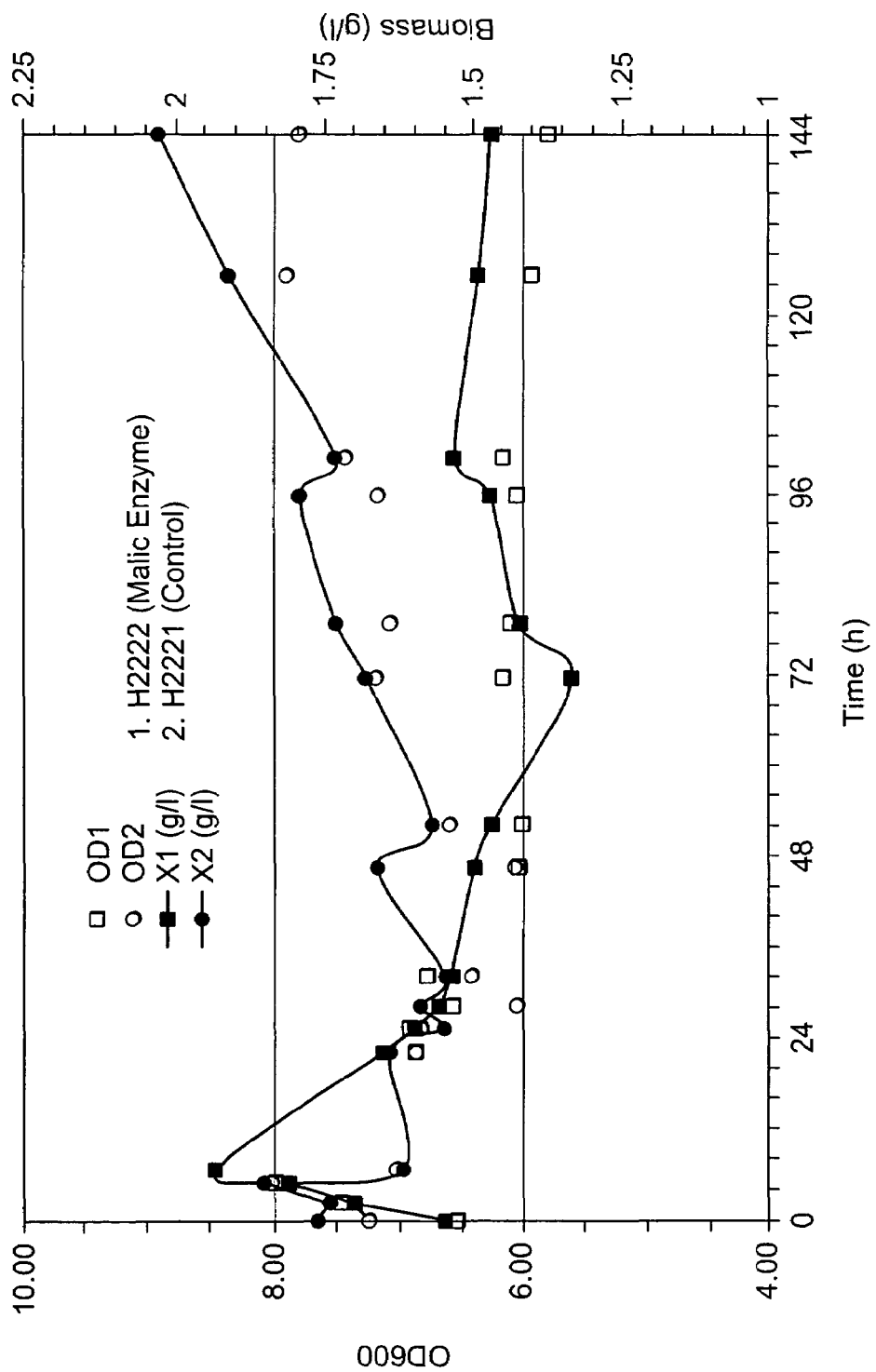
FIG. 12. Biomass time profiles for xylose batch fermentations of *Saccharomyces cerevisiae* recombinant strain expressing MAE1 (H2222) and control strain (H2221).

As indicated in FIG. 11, the enhancement of specific ethanol production rate is close to 30% compared with the control, and the specific xylose utilization is up by about 5%. Furthermore, as indicated by FIG. 12, the control strain accumulates a significantly higher amount of biomass over this 144-hr time period (2.03 vs. 1.47 g/l, i.e. ca +40%). This behavior appears to be different as compared with strains H2195 and H2191 described in part (a) above. A plausible cause for this difference can lie with XK which can play a significant role in xylose utilization (note that H2222 and H2221 carry chromosomal integrations of native XK). However, the reduction in biomass observed in part (b) is in good agreement with that observed in example 13 that deals with the effect of MAE1 on glucose conversion to ethanol. In addition, the molar yield of ethanol on xylose was about 25% higher for the strain that overexpresses the malic enzyme: 0.114 vs. 0.091 C-mol ethanol per C-mol xylose.

In summary, these experiments disclose that the recombinant *S. cerevisiae* strains H2195 and H2222 overexpressing the native malic enzyme (MAE1) in genetic backgrounds without and with XK, respectively, have significantly enhanced capabilities for xylose utilization and ethanol production from xylose as the carbon substrate (up to 30%). In addition, strain H2222 produces less (undesired) acetate (−30% o). In the background lacking XK only the microorganism transformed according to the invention (H2195) is able to survive under the process conditions. On the other hand, in the background with XK, where the non-transformed microorganism can survive, the microorganism transformed according to the invention (H2222) produces significantly less (undesired) cell mass (up to 40%), thereby not only increasing yields of desired products but also decreasing disposal loads.

EXAMPLE 15

Construction of an Integration Vector for Expression of the Gene Encoding Malic Enzyme from *S. Cerevisiae* in *Schizosaccharomyces Pombe*

The YEplac195 vector with the malic enzyme including PGK promoter and terminator from example 10 was digested with HindIII and the 3.7 kbp fragment isolated from an agarose gel. This fragment was treated with Klenow enzyme to make blunt ends. This fragment was then ligated to the SmaI site of the vector pJK210 (ATCC86957). The vector was digested with AvrII for integration by homologous recombination in the URA4 gene.

EXAMPLE 16

Construction of a Multicopy Vector for Expression of the Genes Encoding Xylose Reductase and Xylitol Dehydrogenase of *P. Stipitis* in *Schizosaccharomyces Pombe*

The SacI and NsiI fragment from Example 1, containing the gene for xylose reductase under PGK promoter and terminator and the gene for xylitol dehydrogenase under a modified ADH1 promoter and terminator was isolated from an agarose gel. It was then ligated to the vector pSP1 (ATCC77497), which contains the LEU2 gene, which was linearized by digesting with PstI and SacI.

EXAMPLE 17

Transformation of *Schizosaccharomyces Pombe*

The linerized vector from example 15 was transformed by electroporation (http://www.bio.uva.nl/pombe/handbook) to the *S. Pombe* strain ATCC201400. A control strain was made in a similar way be integrating the empty vector pJK210. The transformants were selected for URA auxotrophy. The multicopy vector from example 16 was transformed in the same way. Transformants were selected for additional LEU auxotrophy. The resulting strain is called H2369 (VTT C-99323) and the control strain without malic enzyme activity H2370 (VTT C-99324).

EXAMPLE 18

Effect of Malic Enzyme: Ethanol Production from Xylose with *Schizosaccharomyces Pombe*

Xylose fermentation to ethanol was conducted in a 1.8 liter Chemap CMF Fermentor (Switzerland) by genetically engineered strains of *Schizosaccharomyces pombe* derived from *S. pombe* strain H2153 (ATCC 201400). More specifically, the two strains used in this example are as follows: (i) H2369: H2153 carrying a chromosomal integration of the *S. cerevisiae* gene encoding malic enzyme and transformed with a multi-copy plasmid that expresses the genes encoding xylose reductase (XR) and xylitol dehydrogenase (XDH) of *Pichia stipitis*. (ii) H2370: H2153 carrying a chromosomal integration of the cloning vector pJK210 and transformed with a multi-copy plasmid that expresses genes encoding xylose reductase (XR) and xylitol dehydrogenase (XDH) of *Pichia stipitis*. Omitting uracil (URA) and leucine (LEU) from the growth media minimizes plasmid segregation.

The inoculum was prepared by transferring a single colony into a 250 ml Erlenmeyer flask that contained 20 ml of Edinburgh Minimal Medium (http://www.bio.uva.nl/pombe/handbook/sectionl/sectionl-8.html) with 225 mg/l adenine, histidine and lysine hydrochloride added (EMM2+ADE+HIS+LYS)+20 g/l glucose. Cells were grown about 50 hours on a rotary shaker at 200 rpm, 30° C. and then the whole broth was transferred to another 250 ml Erlenmeyer flask that contained 50 ml of the same medium. Cells were grown about 24 hours on a rotary shaker at 200 rpm, 30° C. and then the whole broth was transferred to a 2 L flask that contained 700 ml EMM2+ADE+HIS+LYS+50 g/l glucose. The culture was grown for about 40 hours as above and the cells were then washed with 0.1 M phosphate buffer (pH=5.5) and resuspended in the same buffer each to a final volume of 100 ml, OD 600 of the both strains were adjusted to same value with buffer and subsequently transferred to the fermentor. The fermentation medium contained EMM2+ADE (225 mg/L)+HIS (450 mg/L)+LYS (450 mg/L)+50 g/L xylose.

The fermentor temperature was maintained at 30° C., the pH was controlled at 5.5 by addition of 1 M KOH, and the agitation was constant at 300 rpm. The cultivation was carried out under microaerobic conditions by sparging the broth at a constant flowrate of 0.5 SLPM with mixture of nitrogen and air (7:1), the fraction of oxygen in the inlet thus being 2.5%. Liquid samples were withdrawn from the fermentor at time intervals to measure growth, substrate consumption, and the formation of extracellular products. Biomass was measured according to $OD_{600}$ and measuring the dry weight of samples. Xylose, ethanol, xylitol, glycerol and acetate were measured with HPLC. Ethanol was also measured by enzymatic assay with Cobas-Mira.

Figure 13:
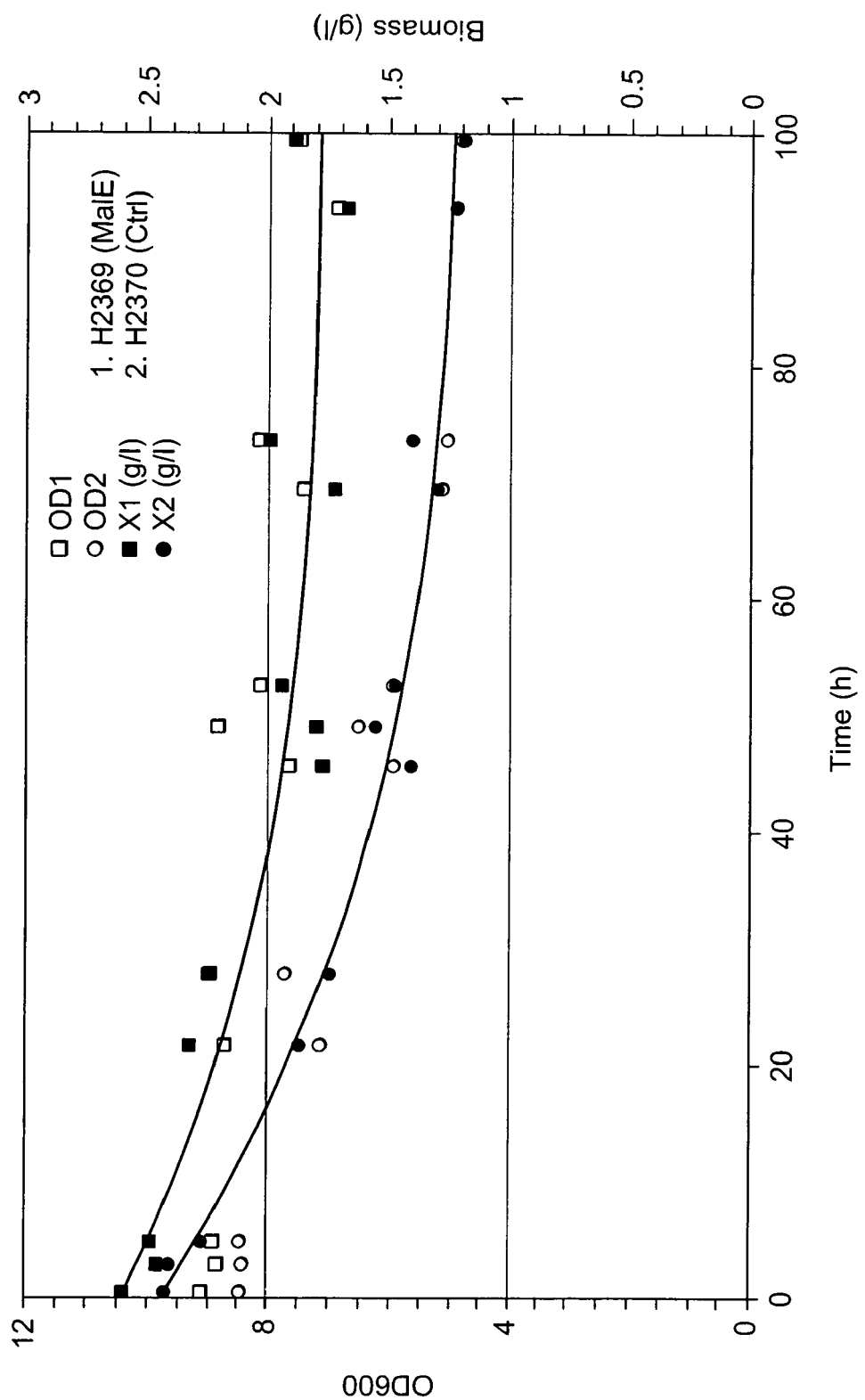
FIG. 13. Biomass profiles for xylose batch fermentations of *Schizosaccharomyces pombe* recombinant strain H2369 expressing malic enzyme, and the control strain H2370.

FIG. 13 shows time profiles for the biomass and turbidity for the strain H2369 and the control strain H2370. As illustrated by FIG. 13, expression of the malic enzyme has indeed a positive effect on cell viability under these conditions. Decline in biomass is from 2.6 to 1.9 g/l with H2369 and from 2.43 to 1.2 g/l with the control strain H2370. Starting at very similar biomass levels, the control decreases by more than 50% and the strain transformed according to the invention by less than 30%. Thus, this is another example disclosing that under conditions where control strains have a poor ability to survive and maintain their biomass and metabolic capacity, strains transformed according to the invention have an improved ability to maintain their biomass and consequently their metabolic capacity. The logarithmic averages of the biomasses during fermentation are 2.23 g/l for H2369 and 1.74 g/l for H2370.

Figure 14:
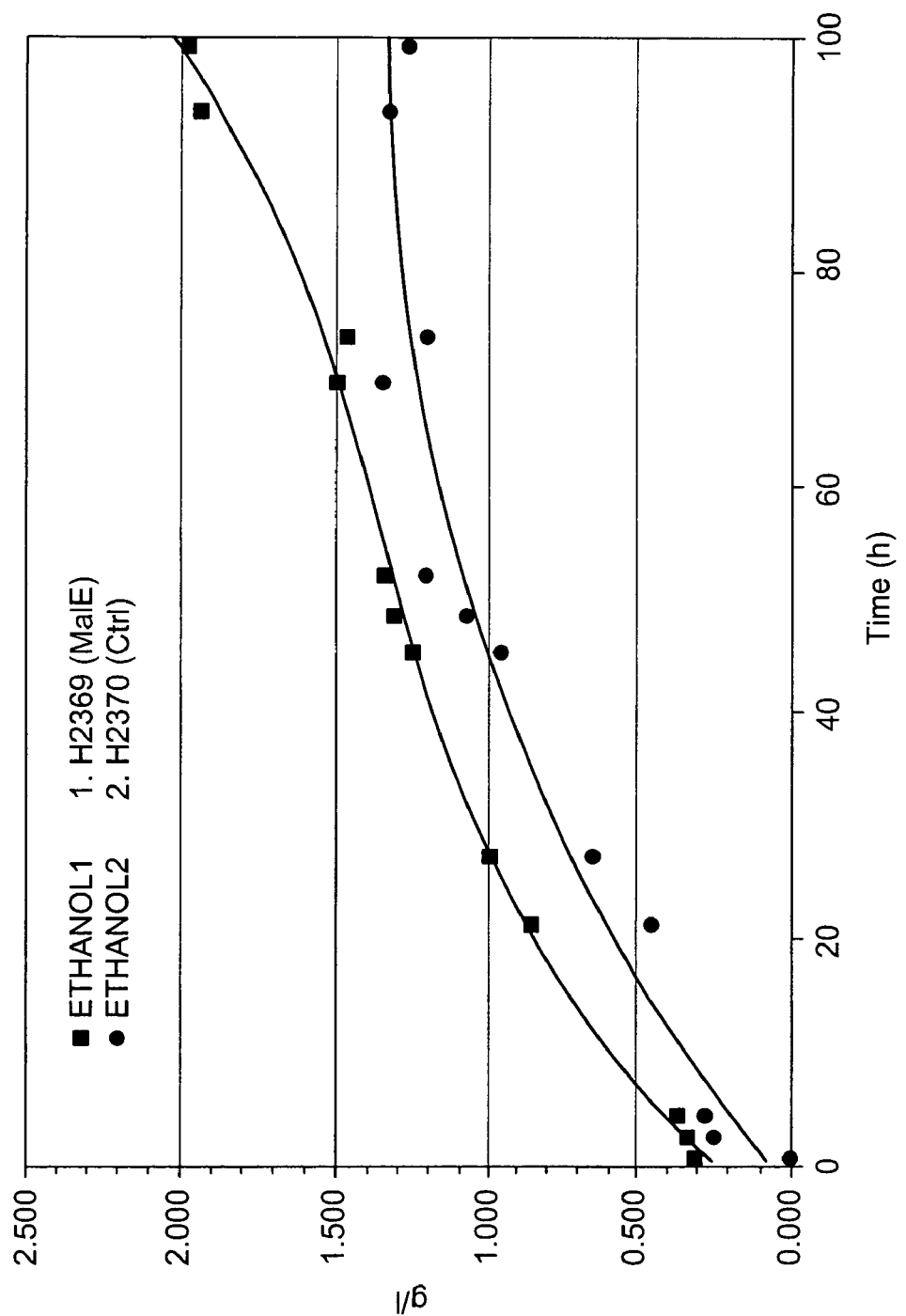
FIG. 14. Time profiles for volumetric ethanol production from xylose in *Schizosaccharomyces pombe* recombinant strain H2369 expressing malic enzyme, and the control strain H2370.

FIG. 14 shows the volumetric ethanol production rates with the strain H2369 and the control strain H2370. As illustrated by FIG. 14 the volumetric ethanol production with H2369 is significantly higher compared to the control strain H2370 (+62%). The specific ethanol production rate is higher by 26% (0.386 vs 0305 C-mmol/g-cell·h). Evidently, in addition to preventing cell degradation, expression of the malic enzyme has also a positive effect on ethanol production. Volumetric xylose utilization is enhanced by 47% (9.7 g/l vs 6.6 g/l). Also the specific rate is enhanced (by about 15%; 1.45 vs 1.26 C-mmol/g-cell·h, results not shown here), showing that the metabolic capacity of the extra biomass maintained by the transformed strain was even greater than that of the control strain.

These results disclose that the recombinant *S. pombe* strain H2369 expressing the *S. cerevisiae* malic enzyme has significantly enhanced capabilities for xylose utilization as well as for ethanol production from xylose. The recombinant strain can also sustain its viability for prolonged time periods. In addition, strain H2369 produces less (undesired) acetate (−43%). These results are comparable with fermentations by *S. cerevisiae* overexpressing native malic enzyme. With *S. cerevisiae* xylose utilization was enhanced by 55% and ethanol production by 20%.

EXAMPLE 19

Cloning the Gene for NAD-Linked Glutamate Dehydrogenase from *Peptostreptococcus Asaccharolyticus*

*Peptostreptococcus asaccharolyticus* (ATCC 14963) was grown anaerobically and genomic DNA isolated. The gene encoding NAD-linked glutamate dehydrogenase was then cloned according to the sequence published by Snedcor et al. (1991) by PCR, using the following oligonucleotides: 5'-GAG GAT CCA TAG GAG CGC ATG TTG GAC C-3' (SEQ ID NO: 13) and 5'-CAG GAT CCT CTG TTA GGG ATT TAC TCC-3' (SEQ ID NO: 14). DyNAzyme EXT polymerase (Finnzymes) was used and the resulting 2.4 kbp PCR product was ligated to the pCR 2.1 TOPO vector (Invitrogen) and transformed to TOP10F' *E. coli* cells (Invitrogen) according to the manufacturer's instructions.

EXAMPLE 20

Construction of an E. coli—Corynebacterium Glutamicum Shuttle Vector Containing the Gene Encoding the NAD-Linked Glutamate Dehydrogenase from Peptostreptococcus Asaccharolyticus The plasmid pAJ655, an E. coli—Corynebacterium glutamicum shuttle vector, was isolated from the Corynebacterium glutamicum strain ATCC 39135 and digested with BamHI. The vector was purified on an agarose gel and the ends dephosphorylated with shrimp alkaline phosphatase.

The pCR 2.1 TOPO vector with the gene coding for the NAD-linked glutamate dehydrogenase from Peptostreptococcus asaccharolyticus from Example 19 was digested with BamHI and the 2.4 kbp fragment isolated from an agarose gel. The 2.4 kbp fragment was then ligated to the linearised shuttle vector and transformed to E. coli DH5α cells.

EXAMPLE 21

Transformation of the Shuttle Vector to a Strain of Corynebacterium Glutamicum

The strains of Corynebacterium glutamicum ATCC 21799 (E-991193) and ATCC 21253 (E-991192) were transformed with the shuttle vector obtained in Example 20 by electroporation (Follettie [1989]). These strains were chosen because they have been developed to overproduce lysine.

Figure 15:
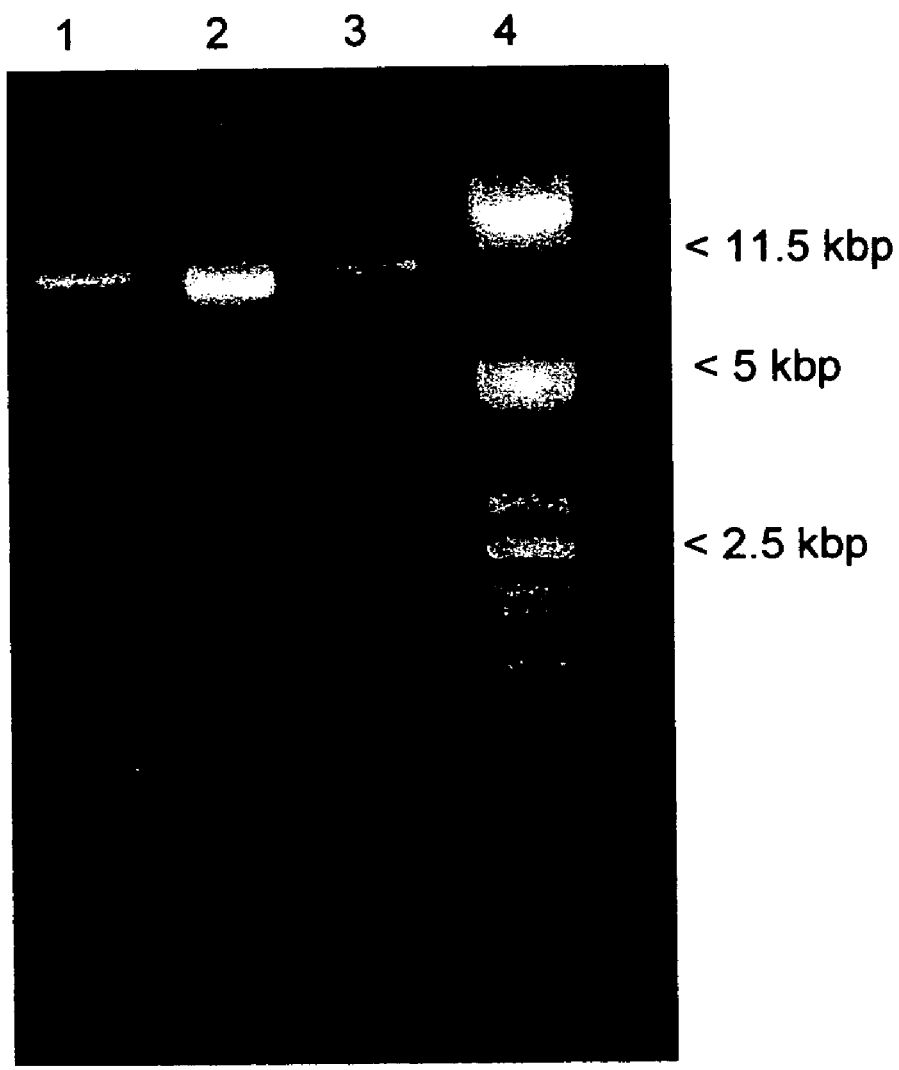
FIG. 15. Separation of BamHI digestion products of the vectors from the *Corynebacterium* transformants described in Example 21. Lane 1: digestion of the vector from ATCC 21253 transformant, Lane 2: Not relevant for this experiment, Lane 3: digestion of the vector from ATCC 21799 transformant (VTT E-992103).

The plasmid was recovered from the transformed strains, digested with BamHI and the digestion products separated on an agarose gel as shown in FIG. 15. In lane 1 is the undigested vector from a transformant of ATCC 21253 and in lane 3 is the digested vector from a transformant of ATCC 21799 which is called VTT E-991203 E 992103. The figure shows the 10 kbp vector and the 2.4 kbp insert. A second isolate of transformed ATCC 21799 was named VTT E-991204 E 992104, and the plasmid recovered from this isolate behaved in the same way as shown for VTT E-991203 in FIG. 15.

EXAMPLE 22

Measuring NAD-Linked Glutamate Dehydrogenase Activity in Cell Extracts of Corynebacterium Glutamicum Cell extracts of Corynebacterium glutamicum cells were prepared by vortexing 500 mg wet weight of cells, 500 μl 100 mM sodium phosphate buffer pH 7.0 and 500 μl glass beads for 20 minutes at 4° C. in 15 ml Eppendorf tubes. The tubes were centrifuged at 4° C. and 13000 rpm in a table top centrifuge and the supernatant analysed. The buffer for the activity assay contained 100 mM sodium phosphate pH 7.0, 20 mM ammonium chloride and 200 μM NADH. The reaction was started by adding α-ketoglutarate to a final concentration of 2 mM. The activity was calculated from the change in NADH absorbance at 340 nm. The enzyme assays were done at 30° C. The amount of extracted protein was measured with the BioRad protein assay using IgG as a standard. Enzyme activities between 0.1–0.2 nkat/mg were found for a transformant of the ATCC 21253 strain and 0.1–0.2 nkat/mg for transformants of the strain ATCC21799 which are called VTT E-991203 and VTT E-991204.

EXAMPLE 23

Lysine Production by Transformed Corynebacterium Glutamicum

Fermentation in shake flasks: The strains VTT E-991203 and VTT E-991204 were analysed in shake flask fermentations as described by Kiss (1991), except that the antibiotic used was 10 mg/l chloramphenicol instead of kanamycin. As a control the parent strain ATCC 21799 was grown in the absence of an antibiotic. 1 ml of a preculture, grown on LB, was diluted into 50 ml CGM1 medium (Kiss [1991]) and grown at 30° C. in baffled 250 ml Erlenmeyer flasks on a shaker at 250 rpm. The amino acids in the supernatants were analysed by HPLC and glucose with an enzyme assay. Results are shown in Table 4.

TABLE 4

Production of lysine by a contr 1 strain (ATCC21799) and two transformants according to the invention of Corynebacterium glutamicum.

| | Biomass (g dry wt./l) | Glucose utilized (g/l) | Threonine utilized (mg/l) | Lysine produced (g/g biomass) | Lysine produced (g/g glucose utilized) |
|---|---|---|---|---|---|
| VTT E-991203 | 0.855 | 3.3 (16.5%) | 73.6 (49%) | 0.408 | 0.105 |
| VTT E-991204 | 1.236 | 3.5 (17.5%) | 94.8 (63%) | 0.426 | 0.150 |
| ATCC 21799 | 4.93 | 13.7 (68.5%) | 144.7 (96%) | 0.484 | 0.173 |

The two transformed strains VTT E-991203 and VTT E-991204 grew more slowly than the control because (unlike the control) they contain shuttle vectors and were cultivated in the presence of chloramphenicol. When lysine production was measured, the transformants were still in phase I of the fermentation, i.e. threonine was still present, whereas the control was close to or in stationary phase and had consumed nearly all the threonine. In Corynebacteria overproduction of L-lysine starts only in phase II, after the threonine is utilized (Vallino [1991]). Remarkably, however, the transformants already produced lysine during phase I, and the amounts of lysine produced per gram biomass were only 16% and 12% less than those produced by the control in the normal lysine over-producing stage (phase II). Furthermore, the yields of lysine on glucose utilised obtained with the transformants markedly increased as the transformants grew through phase I (from 0.105 g/g when 49% of threonine was consumed to 0.15 g/g when 63% of threonine was consumed). For conventional lysine-over-producing strains of Corynebacterium glutamicum the lysine yields on glucose utilised expected at this stage of the fermentation are close to zero (Vallino [1991]). It is evident that when the transformants emerge from phase I into the normal lysine overproduction stage (when growth is complete, and glucose is no longer diverted to biomass production) the rates and yields of lysine production will exceed those of the control. It is clear to those skilled in the art that the slow growth of the transformants can be accelerated by integrating the gene for NAD-linked glutamate dehydrogenase into the transformants' genomes, thereby avoiding the handicap of supporting a plasmid and eliminating the need for chloramphenicol in the growth medium.

This example discloses that transformation of a lysine-overproducing strain of Corynebacterium glutamicum with a gene for NAD-linked glutamate dehydrogenase according to the invention enhances the production of lysine by the transformant at least during early growth stages. It is expected that substantial enhancement of lysine yields on glucose will be obtained when the fermentations with transformants are continued into phase II.

EXAMPLE 24

Coexpression of the Genes from *Alcaligenes Eutrophus* Encoding Polyhydroxybutyrate (PHB) Reductase and PHB Synthase with the Gene Encoding NAD-Dependent Glutamate Dehydrogenase or the Gene Encoding Malic Enzyme of *S. Cerevisiae*

Plasmid pRS303 (Sikorski and Hieter [1989]) was digested with SacI and XbaI and isolated from a 0.7% agarose gel. The 4.8 kbp GDH2 fragment (containing the gene with its own promoter) on a SacI/XbaI cassette (Boles et al. [1993]) was ligated into the pRS303 vector creating the plasmid pGDH2-303. The 2 micron origin of replication was cut from the plasmid pLGSD5 (Guarente et al. [1982]) with EcoRI and the ends rendered blunt with the Klenow Large Fragment Polymerase. Plasmid pRS303 was digested with XhoI and the ends rendered blunt with the Klenow Large Fragment Polymerase. The origin of replication was then ligated into pRS303 creating plasmid pTL92.

Plasmid pGDH2-303 was digested with SmaI and a doublet band of ~4.8 kbp containing both the GDH2 fragment (4.8 kbp) and the backbone vector (4.5 kbp) was isolated from an agarose gel. The recovered fragments were then digested with KpnI. This digestion cleaves the backbone vector (pRS303) into two fragments thus allowing the isolation of the 4.8 kbp band containing the GDH2 fragment. Plasmid pTL92 was linearized with SmaI and isolated from an agarose gel. The linearized vector was dephosphorylated with CIAP (calf intestinal alkaline phosphatase) at 37° C. for one hour and then purified on an agarose gel. The blunt GDH2 fragment and blunt vector pTL92 were ligated creating p2-GDH2.

The plasmid p2-GDH2 can be transformed into *S. cerevisiae* strain D603 (MATa/MATα, ura3-52, lys2-801, met, his3, ade2-101, reg1-501; Srienc et al. [1986]) expressing the heterologous genes from *Alcaligenes eutrophus* encoding PHB reductase and PHB synthase on a multicopy plasmid p2DPF with a bidirectional, inducible galactose promoter (Carlson 1999]). Shake flask and bioreactor cultivations with appropriate controls can be performed in enriched SD media (DaSilva [1988]) containing 10 g/l of each glucose and galactose. The PHB content of control cells and cells transformed according to the invention are determined by GC analysis of dichloroethane extracts of dried cell material subjected to propanolysis (Riis and Mai [1988], Leaf et al. [1996]). Sugar consumption and gas exchanges are measured by standard methods. In this way the advantages expected from the invention, such as increased yield of PHB on glucose, increased productivity, decreased $CO_2$ production and decreased oxygen requirement can be demonstrated.

It is clear that the 3.8 kbp fragment with the MAE1 gene between the promoter and terminator of PGK1 (see example 10) can be cloned and expressed in the yeast D603 with a similar strategy as used for the GDH2 gene.

Similar strategies can be used to introduce genes for dehydrogenases according to the invention into other microorganisms producing PHB and other PHAs, including bacteria already used in the industrial production of PHAs, such as *Alcaligenes eutrophus*. Advantageous enzymes include the NAD-linked glutamate dehydrogenase from *Peptostreptococcus asaccharolyticus* used in Example 21 to transform another bacterium, *Corynebacterium glutamicum*.

Deposited microorganisms

The following microorganisms were deposited under the rules of the Budapest Treaty at the DSMZ-Deutsche Sammlung von Mikroorganismen und Zellkulturen GmbH, Mascheroder Weg 1b, D-38124 Braunschweig, Germany

| Microorganism | Accession number | Date of deposit |
|---|---|---|
| *Saccharomyces cerevisiae* | | |
| H1791 (VTT C-98298) | DSM 12213 | 4 Jun. 1998 |
| H1795 (VTT C-98300) | DSM 12214 | 4 Jun. 1998 |
| H1803 (VTT C-98302) | DSM 12215 | 4 Jun. 1998 |
| H2193 (VTT C-99317) | DSM 12722 | 5 Mar. 1999 |
| H2195 (VTT C-99320) | DSM 12723 | 5 Mar. 1999 |
| H2222 (VTT C-99322) | DSM 12724 | 5 Mar. 1999 |
| *Schizosaccharomyces pombe* | | |
| H2369 (VTT C-99323) | DSM 12725 | 5 Mar. 1999 |
| H2370 (VTT C-99324) | DSM 12726 | 5 Mar. 1999 |
| *Corynebacterium* | | |
| VTT E-991203 | DSM 12728 | 12 Mar. 1999 |
| VTT E-991204 | DSM 12729 | 11 Mar. 1999 |

REFERENCES

Amore R, Wilhelm M and Hollenberg CP (1989) The fermentation of xylose—an analysis of the expression of *Bacillus* and *Actinoplanes* xylose isomerase genes in yeast. Appl. Microbiol. Biotechnol. 30: 351–357

Anderson A J and Dawes E A (1990). Occurrence, metabolism, metabolic role, and industrial uses of bacterial polyhydroxyalkanoates. Microbiol. Reviews 54: 450–472.

Avendaño A, Deluna A, Olivera H, Valenzuela L and Gonzales A (1997). GDH3 encodes a glutamate dehydrogenase isozyme, a previously unrecognized route for glutamate biosynthesis in *Saccharomyces cerevisiae*. J. Bacteriol. 179: 5594–5597.

Beier D R and Young E r (1982). Characterization of a regulatory region upstream of the ADR2 locus of *S. cerevisiae*. Nature 300: 724–728.

Bergmeyer (1974). Methods of Enzymatic Analysis; Academic Press.

Björkqvist S, Ansell R, Adler L and Lidén G (1997) Physiological response to anaerobicity of glycerol-3-phosphate dehydrogenase mutants of *Saccharomyces cerevisiae*. Appl. Environ. Microbiol. 63: 128–132.

Boeke J D, LaCroute F and Fink G R (1984). A positive selection for mutants lacking orotidine-5'-phosphate decarboxylase activity in yeast: 5-fluoro-orotic acid resistance. Mol. Gen. Genet. 197: 345–346.

Boles E, Lehnert W and Zimmermann F K (1993). The role of the NAD-dependent glutamate dehydrogenase in restoring growth on glucose of a *Saccharomyces cerevisiae* phosphoglucose isomerase mutant. Eur. J. Biochem. 217: 469–477.

Boles E, Göhlmann H W H and Zimmermann F K (1996). Cloning of a second gene encoding 6-phosphofructo-2- kinase in yeast, and characterization of mutant strains without fructose-2,6-bisphosphate. Mol. Microbiol. 20: 65–76.

Bruinenberg P M, de Bot P H M, van Dijken J P and Scheffers W A (1983). The role of redox balances in the anaerobic fermentation of xylose by yeasts. Eur. J. Appl. Microbiol. Biotechnol. 18: 287–292.

Bruinenberg P M (1986) The NADP(H) redox couple in yeast metabolism. Antonie van Leeuwenhoek 52: 411–429.

Carlson R P (1999). Utilizing the bi-directional GAL1-10 promoter to co-express two genes in *Saccharomyces cerevisiae*. Masters Thesis. University of Minnesota, USA.

Chen Z, Tsigelny I, Lee W R, Baker M E and Chang S H (1994). Adding a positive charge at residue 46 of *Drosophila* alcohol dehydrogenase increases cofactor specificity for NADP$^+$. FEBS Lett. 356: 81–85.

Chen R, Greef A F and Dean A M (1997). Structural constraints in protein engineering. The coenzyme specificity of *Escherichia coli* isocitrate dehydrogenase. Eur. J. Biochem. 250: 578–582.

Christianson T W, Sikorski R S, Dante M, Shero J H and Hieter P (1992). Multifunctional yeast high-copy-number shuttle vectors. Gene 110: 119–122.

Coschigano P W, Miller S M and Magasanik B (1991) Physiological and genetic analysis of the carbon regulation of the NAD-dependent glutamate dehydrogenase of *Saccharomyces cerevisiae*. Mol. Cell. Biol. 11: 4455–465.

Courchesne W E and Magasanik B (1988) Regulation of nitrogen assimilation in *Saccharomyces cerevisiae*: roles of URE2 and GLK3 genes. J. Bacteriol. 170: 708–713.

Dang V-D, Bohn C, Bolotin-Fukuhara M and Daignan-Formier B (1996). The CCAAT box-binding factor stimulates ammonium assimilation in *Saccharomyces cerevisiae*, defining a new cross-pathway regulation between nitrogen and carbon metabolisms. J. Bacteriol. 178: 1842–1849.

DaSilva N A (1988). Host-plasmid interactions and regulation of cloned gene expression in recombinant cells. PhD Thesis. California Institute of Technology, Pasadena, Calif., USA.

Fink G (1964). Gene-enzyme relations in histidine biosynthesis in yeast. Science 146: 525-.

Follettie M T (1989) DNA Technology for *Corynebacterium glutamicum*: Isolation and characterization of amino acid biosynthetic genes. Ph.D. thesis, Massachusetts Institute of Technology, Cambridge, Mass.

Follettie M T, Archer J, Peoples O P and Sinskey A J (1991). Metabolic engineering of Corynebacteria. In Societe Microbiologique Francaise. Edited by H. Heslot, J. Davies, J. Florent, L Bobichon, G. Durand & L Penasse. Paris.

Follettie M T and Sinskey A J (1986). Recombinant DNA technology for *Corynebacterium glutamicum*. Food Technology 40: 88-.

Fuck E, Stärk G and Radler F (1973). Äpfelsäurestoffwechsel bei *Saccharomyces*. II. Anreicherung und Eigenschaften eines Malatenzyms. Arch. Microbiol. 89: 223–231.

Gietz R D and Sugino A (1988). New yeast—*Escherichia coli* shuttle vectors constructed with in vitro mutagenized yeast genes lacking six-base pair restriction sites. Gene 74: 527–534.

Gietz D, St. Jean A, Woods R A and Schiestl (1992). Improved method for high efficiency transformation of intact yeast cells. Nucleic Acids Res. 20: 1425.

Guarente L, Yocum R R and Gifford P (1982). A GAL10-CYC1 hybrid yeast promoter identifies the GAL4 regulatory region as an upstream site. Proc. Natl. Acad. Sci. USA 79: 7410–7414.

Hill J, Donald KAIG and Griffiths. DE (1991). DMSO—enhanced whole cell yeast transformation. Nucleic Acids Res. 19: 5791.

Hirose (1986). Biochemical Effects of Oxygen Supply and Carbon Dioxide Removal in Biotechnology of Amino Acid Production, ed. K. Aida, I. Chibata, K. Nakayama, K. Takinami & H. Yamada. Tokyo: Kodansha-Elsevier. 24: 67–80.

Ho N W Y, Stevis P, Rosenfeld S, Huang J J and Tsao G T (1983) Expression of the *E. coli* xylose isomerase gene by a yeast promoter. Biotechnol. Bioeng. Symp. 13: 245–250.

Ho N W Y and Tsao G T. WO 95/13362.

Jetten M S M, Follettie M T and Sinskey A 1 (1994). Metabolic engineering of *Corynebacterium glutamicum*. In Recombinant DNA Technology II, pp. 12–29. Edited by R. Bajpai & A. Prokop. New York: Annals New York Academy of Science.

Jetten M S and Sinskey A J (1995). Recent advances in the physiology and genetics of amino acid-producing bacteria. Critical Reviews in Biotechnology 15: 73–103.

Kaplan (1960). page 150 in The Enzymes, 2nd edition, ed. Boyer, Lardy, Myrbäack; Academic Press.

Kiss R D (1989). Metabolic activity control of the L-lysine fermentation by restrained growth fed-batch strategies. Ph.D. thesis, Massachusetts Institute of Technology, Cambridge, Mass.

Kötter P and Ciriacy M (1993). Xylose fermentation by *Saccharomyces cerevisiae*. Appl. Microbiol. Biotechnol. 38: 776–783.

Leaf T, Peterson M, Stoup S, Somers D and Srienc F (1996). *Saccharomyces cerevisiae* expressing bacterial polyhydroxybutyrate synthase produces poly-3-hydroxybutyrate. Microbiol. 142: 1169–1180.

Marx A, Bernhard J E, Sahm H, de Graaf A A and Eggeling L. (1999). Response of the Central Metabolism in *Corynebacterium glutamicum* to the use of an NADH-Dependent Glutamate Dehydrogenase. Metabolic Engineering 1: 35–48

McAlister-Henn L, Steffan I S, Minard K I and Anderson S L (1995). Expression and function of a mislocalized form of peroxisomal malate dehydrogenase (MDH3) in yeast. J. Biol. Chem. 270: 21220–21225.

Mellor J, Dobson M I, Roberts, N A, Tuite M F, Emtage J S, White S, Lowe P A, Patel T, Kingsman A J and Kingsman S M (1983). Efficient synthesis of enzymatically active calf chymosin in *Saccharomyces cerevisiae*. Gene 24: 1–14.

Metzger M H and Hollenberg C P (1995). Amino acid substitutions in the yeast *Pichia stipitis* xylitol dehydrogenase coenzyme-binding domain affects the coenzyme specificity. Eur. J. Biochem. 228: 50–54.

Metzler (1977). page 466 in Biochemistry: the chemical reactions of the living cell; Academic Press Miller S M and Magasanik B (1991) Role of the complex upstream region of the GDH2 gene in nitrogen regulation of the NAD-linked glutamate dehydrogenase in *Saccharomyces cerevisiae*. Mol. Cell. Biol. II: 6229–6247.

Minard K I and McAlister-Henn L (1992). Glucose-induced degradation of the MDH2 isozyme of malate dehydrogenase in yeast. J. Biol. Chem. 267: 17458–17464.

Minard K I, Jennings G T, Loftus T M, Xuan, D and McAlister-Henn L. (1998). Sources of NADPH and expression of mammalian NADP+-specific isocitrate dehydrogenases in *Saccharomyces cerevisiae*. J. Biol. Chem 273: 31486–31493.

Neidhardt F C, Ingraham J L and Schaechter M (1990). Physiology of the Bacterial Cell: a Molecular Approach. Sunderland, Mass.: Sinauer Associates, Inc.

Oura E (1972) The effect of aeration on the growth energetics and biochemical composition of baker's yeast. Doctoral Dissertation, University of Helsinki. p. 30

Oura E (1977) Reaction products of yeast fermentations. Process Biochem. 12: 19–21, 35.

Poirier Y, Nawrath C and Somerville C (1995). Production of polyhydroxyalkanoates, a family of biodegradable plastics and elastomers, in bacteria and plants. BIO/Technology 13: 142–150.

Riis V and Mai W (1988). Gas chromatographic determination of poly-β-hydroxybutyric acid in microbial biomass after hydrochloric acid propanolysis. J. Chromatogr. 445: 285–289.

Rose M, Grisafi P and Botstein D (1984). Structure and function of the yeast URA3 gene: expression in *Escherichia coli*. Gene 29: 113–124.

Ruohonen L, Aalto M and Keränen S (1995). Modifications to the ADH1 promoter of *Saccharomyces cerevisiae* for efficient production of heterologous proteins. J. Biotechnol. 39: 193–203.

Sáez M J and Lagunas R (1976) Determination of intermediary metabolites in yeast. Critical examination of the effect of sampling conditions and recommendations for obtaining true levels. Mol. Cell. Biochem. 13: 73–78.

Sarthy A V, McConaughy B L, Lobo Z, Sundström J A, Furlonf C L and Hall B D (1987) Expression of the *E. coli* xylose isomerase gene in *Saccharomyces cerevisiae*. Appl. Environ. Microbiol. 53: 1996–2000.

ter Schure E G, SilljéH H W, Verkleij A J, Boonstra J and Verrips C T (1995). The concentration of ammonia regulates nitrogen metabolism in *Saccharomyces cerevisiae*. J. Bacteriol. 177: 6672–6675.

Sherman F, Fink G R and Hicks J B (1983). Methods in Yeast Genetics. A Laboratory Manual. Cold Spring Harbor Laboratory. Cold Spring Harbor, N.Y.

Sikorski R S and Hieter P. (1989). A system of shuttle vectors and yeast host strains designed for efficient manipulation of DNA in *Saccharomyces cerevisiae*. Genetics, 122: 19–27.

Snedcor B, Chu H and Chen E (1991). Selection, Expression, and Nucleotide Sequencing of the Glutamate Dehydrogenase Gene of *Peptostreptococcus asaccharolyticus* J. Bacteriol. 173: 6162–6167.

Srienc F, Campbell J and Bailey J (1986). Flow cytometry analysis of recombinant *Saccharomyces cerevisiae* populations. Cytometry 7: 132–141.

Tantirungkij M, Izuishi T, Seki T and Yoshida T (1994). Fed-batch fermentation of xylose by a fast-growing mutant of xylose-assimilating recombinant *Saccharomyces cerevisiae*. Appl. Microbiol. Biotechnol. 41: 8–12.

Toikkanen J, Söderlund H. and Keränen S. (1998). Genetic interactions between the early and late secretory pathway in *Saccharomyces cerevisiae*. Manuscript in preparation.

Vallino J J (1991). Ph.D. thesis, Massachusetts Institute of Technology, Cambridge, Mass.

Verduyn C, van Kleef R, Frank J, Schreuder H, van Dijken J P and Scheffers W A (1985). Properties of the NAD(P)H-dependent xylose reductase from the xylose fermenting yeast *Pichia stipitis*. Biochem. J. 226: 669–677.

Viljoen M, Subden R E, Krizus A and van Vuuren H J J (1994). Molecular analysis of the malic enzyme gene (mae2) of *Schizosaccharomyces pombe*. Yeast 10: 613–624.

Wach A, Brachat A, Pöhlmann R and Philippsen P (1994). New heterologous modules for classical or PCR-based gene disruptions in *Saccharomyces cerevisiae*. Yeast 10: 1793–1808.

Walfridsson M, Bao X, Anderlund M, Lilius G, Bülow L and Hahn-Häigerdal B (1996) Ethanolic fermentation of xylose with *Saccharomyces cerevisiae* harboring the *Thermus thermophilus* xyLA gene, which expresses an active xylose (glucose) isomerase. Appl. Environ. Microbiol. 62: 4648–4651.

Walfridsson M, Hallborn J, Penttilä M, Keränen S and Hahn-Hägerdal B (1995) Xylose-metabolizing *Saccharomyces cerevisiae* strains overexpressing the TKL1 and TAL1 genes encoding the pentose phosphate pathway enzymes transketolase and transaldolase. Appl. Environ. Microbiol. 61: 4184–4190.

---

The invention claimed is:

1. *Saccharomyces cerevisiae* strains selected from the group consisting of H1791 (VTT C-98298, DSM 12213), H1795 (VTT C-98300, DSM 12214), H1803 (VTT C-98302, DSM 12215), H2193 (VTT C-99317, DSM 12722), H2195 (VTT C-99320, DSM 12723) and H2222 (VTT C-99322, DSM 12724).

2. *Schizosaccharomyces pombe* strains selected from the group consisting of H2369 (VTT C-99323, DSM 12725) and H2370 (VTT C-99324, DSM 12726).

3. A method for increasing yield of ethanol produced during a microbial production process comprising the steps of:
(a) transforming a host microorganism selected from the group consisting of *Saccharomyces* spp. and *Schizosaccharomyces* spp. with one or more polynucleotides encoding an enzyme to produce a transformed microorganism, wherein said enzyme is selected from the group consisting of NAD-dependent glutamate dehydrogenase, and malic enzyme, wherein the host microorganism carries the genes for xylose reductase and xylitol dehydrogenase enzymes and
(b) culturing the transformed microorganism to produce ethanol,
thereby increasing the yield of ethanol when compared to the yield of ethanol when produced in a microorganism that has not been transformed according to step (a).

4. The method of claim 3, wherein ethanol is produced in an amount that is at least 5% higher than the amount produced in a microorganism that has not been transformed according to step (a).

5. The method of claim 3, wherein the ethanol is produced from carbohydrate.

6. The method of claim 5, wherein said carbohydrate is at least one selected from the group consisting of glucose and xylose.

7. The method of claim 3, wherein the host microorganism is *Saccharomyces cerevisiae*.

8. The method of claim 3, wherein the host microorganism is *Schizosaccharomyces pombe*.

9. The method of claim 3, wherein the host microorganism carries, in addition, the gene for xylulose kinase.

* * * * *